(12) United States Patent
Zetterberg

(10) Patent No.: US 11,046,725 B2
(45) Date of Patent: Jun. 29, 2021

(54) GALACTOSIDE INHIBITOR OF GALECTINS

(71) Applicant: GALECTO BIOTECH AB, Copenhagen (DK)

(72) Inventor: Fredrik Zetterberg, Askim (SE)

(73) Assignee: GALECTO BIOTECH AB, Copenhagen (DK)

( * ) Notice: Subject to any disclaimer, the term of this patent is extended or adjusted under 35 U.S.C. 154(b) by 0 days.

(21) Appl. No.: 16/960,996

(22) PCT Filed: Jan. 9, 2019

(86) PCT No.: PCT/EP2019/050467
§ 371 (c)(1),
(2) Date: Jul. 9, 2020

(87) PCT Pub. No.: WO2019/137971
PCT Pub. Date: Jul. 18, 2019

(65) Prior Publication Data
US 2020/0347089 A1    Nov. 5, 2020

(30) Foreign Application Priority Data
Jan. 10, 2018 (EP) .................................... 18150959

(51) Int. Cl.
*C07H 19/056* (2006.01)

(52) U.S. Cl.
CPC .................................. *C07H 19/056* (2013.01)

(58) Field of Classification Search
None
See application file for complete search history.

(56) References Cited

U.S. PATENT DOCUMENTS

| | | |
|---|---|---|
| 7,638,623 B2 | 12/2009 | Nilsson et al. |
| 2007/0185041 A1 | 8/2007 | Leffler et al. |
| 2014/0099319 A1 | 4/2014 | Traber |

FOREIGN PATENT DOCUMENTS

| | | | |
|---|---|---|---|
| EP | 1 256 586 A1 | 11/2002 | |
| WO | 2005/113568 A1 | 12/2005 | |
| WO | 2005/113569 A1 | 12/2005 | |
| WO | 2010/126435 A1 | 11/2010 | |
| WO | 2014/067986 A1 | 5/2014 | |
| WO | 2016/120403 A1 | 8/2016 | |
| WO | WO-2016120403 A1 * | 8/2016 | ............... A61P 35/00 |
| WO | 2018/011093 A1 | 1/2018 | |

OTHER PUBLICATIONS

International Search Report and Written Opinion of the International Searching Authority dated Mar. 22, 2019, in corresponding International Application No. PCT/EP2019/050467; 13 pages.

Leffler et al., "Introduction to galectins", in Glycoconjugate Journal 19, 2004, p. 433-440; 8 pages.
Adriana Lepur et al., "Ligand Induced Galectin-3 Protein Self-association", Journal of Biological Chemistry vol. 287, No. 26, pp. 21751-21756, Jun. 22, 2012; 7 pgs.
Ada G. Blidner et al., "Re-wiring regulatory cell networks in immunity by galectin-glycan interactions", FEBS Letters 589 (2015) 3407-3418; 12 pgs.
Ali Hasan Ebrahim et al., "Galectins in cancer: carcinogenesis, diagnosis and therapy", Ann Transl Med 2014;2(9):88, 7 pgs.
Douglas N.W. Cooper et al., "Endogenous Muscle Lectin Inhibits Myoblast Adhesion to Laminin", The Journal of Cell Biology, vol. 115, No. 5, Dec. 1991 1437-1448; 12 pgs.
Connie M. Arthur, et al., "Evolving Mechanistic Insights into Galectin Functions", Methods Mol Biol. 2015 ; 1207: 1-35; 37 pgs.
Maria T. Elola et al., "Assembly, organization and regulation of cell-surface receptors by lectin-glycan complexes" Biochem. J. (2015) 469, 1-16; 16 pgs.
Sonja Aits et al., "Sensitive detection of lysosomal membrane permeabilization by lysosomal galectin puncta assay", Autophagy 11:8, 1408-1424, Published online:Aug. 14, 2015; 18 pgs.
Helen Blanchard et al., "Galectin-1 inhibitors and their potential therapeutic applications: a patent review", Expert Opinion on Therapeutic Patents, vol. 26, 2016—Issue 5; 18 pgs.
Nancy L. Perillo et al., "Apoptosis of T cells mediated by galectin-1", Nature, vol. 378, Dec. 14, 1995; 4 pgs.
Toscano et al., "Differential glycosylation of TH1, TH2 and TH-17 effector cells selectively regulates susceptibility to cell death", in Nature Immunology, vol. 8, No. 8, Aug. 2007, p. 825-834; 10 pages.
Pablo F. Hockl et al., "Glyco-nano-oncology: Novel therapeutic opportunities by combining small and sweet", Pharmacological Research 109 (2016) 45-54, 10 pgs.
MacKinnon et al., "Regulation of Alternative Macrophage Activation by Galectin-3", in The Journal of Immunology, vol. 180, 2008, p. 2650-2658; 9 pages.
MacKinnon et al., "Regulation of Transforming Growth Factor-β1-driven Lung Fibrosis by Galectin-3", in Am. J. Resp. Crit. Care Med., vol. 185, 2012, p. 1-11; 11 pages.
Partridge et al., "Regulation of Cytokine Receptors by Golgi N-Glycan Processing and Endocytosis", in Science, vol. 306, Oct. 1, 2004, p. 120-124; 6 pages.
Jaymin J Kathiriya et al., "Galectin-1 inhibition attenuates profibrotic signaling in hypoxia-induced pulmonary fibrosis", Cell Death Discovery (2017) 3, 17010; 13 pgs.
Frederic van den Brule et al., "Expression of galectins in cancer: A critical review", Glycoconjugate Journal 19, 537-542, 2004; 6 pgs.
Bidon-Wagner et al., "Human galectin-8 isoforms and cancer", in Glycoconjugate Journal 19, 2004, p. 557-563; 7 pages.
Ruvolo, "Galectin 3 as a guardian of the tumor microenvironment", in Biochimica et Biophysica Acta, 2015; http://dx.doi.org/10.1016/j.bbamcr.2015.08.008; 11 pages.
Demotte et al., "A Galectin-3 Ligand Corrects the Impaired Function of Human CD4 and CD8 Tumor-Infiltrating Lymphocytes and Favors Tumor Rejection in Mice", in Cancer Research, vol. 70, 2010, p. 7476-7488; 14 pages.

(Continued)

*Primary Examiner* — Traviss C McIntosh, III
(74) *Attorney, Agent, or Firm* — Maier & Maier, PLLC

(57) ABSTRACT

An α-D-galactopyranose compound of the general formula (1). The α-D-galactopyranose compound of formula (1) is suitable for use in a method for treating a disorder relating to the binding of a galectin, such as galectin-1 to a ligand in a mammal, such as a human. Furthermore, a method for treatment of a disorder relating to the binding of a galectin, such as galectin-1 to a ligand in a mammal, such as a human.

7 Claims, No Drawings

(56) References Cited

OTHER PUBLICATIONS

Kouo et al., "Galectin-3 Shapes Antitumor Immune Responses by Suppressing CD8 T Cells via LAG-3 and Inhibiting Expansion of Plasmacytoid Dendritic Cells", in Cancer Immunology Research, vol. 3, No. 4, Apr. 2015, p. 412-423; 13 pages.

Melero et al., "Evolving synergistic combinations of targeted immunotherapies to combat cancer", in Nature Reviews, vol. 15, Aug. 2015, p. 457-472; 16 pages.

John et al., "Truncated Galectin-3 Inhibits Tumor Growth and Metastasis in Orthotopic Nude Mouse Model of Human Breast Cancer", in Clinical Cancer Research, vol. 9, Jun. 2003, p. 2374-2383; 10 pages.

Lin et al., "Galectin-3 Targeted Therapy with a Small Molecule Inhibitor Activates Apoptosis and Enhances Both Chemosensitivity and Radiosensitivity in Papillary Thyroid Cancer", in Mol. Cancer Res., vol. 7, No. 10, Oct. 2009, p. 1655-1662; 8 pages.

Glinsky et al., "Synthetic Galectin-3 Inhibitor Increases Metastatic Cancer Cell Sensitivity to Taxol-Induced Apoptosis In Vitro and In Vivo", in Neoplasia, vol. 11, No. 9, Sep. 2009, p. 901-909; 9 pages.

Huflejt et al., "Galectin-4 in normal tissues and cancer", in Glycoconjugate Journal 20, 2004, p. 247-255; 9 pages.

Rabinovich et al., "Shedding light on the immunomodulatory properties of galectins: Novel regulators of innate and adaptive immune responses", in Glycoconjugate Journal 19, 2004, p. 565-573; 9 pages.

Pace et al., "Insect galectins: Roles in immunity and development", in Glycoconjugate Journal 19, 2004, p. 607-614; 8 pages.

Françoise Poirier, "Roles of galectins in vivo", Biochem. Soc. Symp. 69, 95-103, 9 pgs.

Watt et al., "The involvement of galectin-1 in skeletal muscle determination, differentiation and regeneration", in Glycoconjugate Journal 19, 2004, p. 615-619; 5 pages.

Leffler, "Galectins Structure and Function—A Synopsis", in Results and Problems in Cell Differentiation, vol. 33, 2001, p. 57-83; 27 pages.

Johan Tejler et al., "Fragment-based development of triazole-substituted O-galactosyl aldoximes with fragment-induced affinity and selectivity for galectin-3", Organic & Biomolecular Chemistry, 2009, 7, 3982-3990; 9 pgs.

Hilde van Hattum et al., "Tuning the Preference of Thiodigalactoside- and Lactosamine-Based Ligands to Galectin-3 over Galectin-1", Journal of Medicinal Chemistry 2013, 56, 1350-1354; 5 pgs.

Leffler et al., "Specificity of Binding of Three Soluble Rat Lung Lectins to Substituted and Unsubstituted Mammalian β-Galactosides", in The Journal of Biological Chemistry, vol. 261, No. 22, Aug. 5, 1986, p. 10119-10126; 8 pages.

Tamara Delaine et al., "Galectin-3-Binding Glycomimetics that Strongly Reduce Bleomycin-Induced Lung Fibrosis and Modulate Intracellular Glycan Recognition", ChemBioChem 2016, 17, 1759-1770; 12 pgs.

Glinsky et al., "Inhibition of Human Breast Cancer Metastasis in Nude Mice by Synthetic Glycoamines", in Cancer Research, vol. 56, Dec. 1, 1996, p. 5319-5324; 6 pages.

David Platt et al., "Modulation of the Lung Colonization of B16-F1 Melanoma Cells by Citrus Pectin", Journal of the National Cancer Institute, vol. 84, No. 6, Mar. 18, 1992; 5 pgs.

Pienta et al., "Inhibition of Spontaneous Metastasis in a Rat Prostate Cancer Model by Oral Administration of Modified Citrus Pectin", in J. Natl. Cancer Inst., vol. 87, No. 5, Mar. 1, 1995, p. 348-353; 6 pages.

Ioannis Vrasidas et al., "Rigidified multivalent lactose molecules and their interactions with mammalian galectins: a route to selective inhibitors", Organic & Biomolecular Chemistry, 2003, 1, 803-810; 8 pgs.

Sabine André et al., "Persubstituted Cyclodextrin-Based Glycoclusters as Inhibitors of Protein-Carbohydrate Recognition Using Purified Plant and Mammalian Lectins and Wild-Type and Lectin-Gene-Transfected Tumor Cells as Targets", Bioconjugate Chem. 2004, 15, 87-98, 12 pgs.

Sabine André et al., "Lactose-containing starburst dendrimers: influence of dendrimer generation and binding-site orientation of receptors (plant/animal lectins and immunoglobulins) on binding properties", Glycobiology, vol. 9, No. 11, pp. 1253-1261, 1999; 10 pgs.

Nicola L. Pohl et al., "Scope of Multivalent Ligand Function: Lactose-Bearing Neoglycopolymers by Ring-Opening Metathesis Polymerization", Synthesis 1999, No. SI, 1515-1519; 5 pgs.

A. David et al., "Design of a multivalent galactoside ligand for selective targeting of HPMA copolymer-doxorubicin conjugates to human colon cancer cells", European Journal of Cancer 40 (2004) 148-157; 10 pgs.

Johan Tejler et al., "Synthesis of multivalent lactose derivatives by 1,3-dipolar cycloadditions: selective galectin-1 inhibition", Carbohydrate Research 341 (2006) 1353-1362; 10 pgs.

Cumpstey et al., "C2-Symmetrical Thiodigalactoside Bis-Benzamido Derivatives as High-Affinity Inhibitors of Galectin-3: Efficient Lectin Inhibition through Double Arginine-Arene Interactions", in Angew. Chem. Int., Ed. 44, 2005, p. 5110-5112; 3 pages.

Cumpstey et al., "Double Affinity Amplification of Galectin-Ligand Interactions through Arginine-Arene Interactions: Synthetic, Thermodynamic, and Computational Studies with Aromatic Diamido Thiodigalactosides", in Chem. Eur. J., vol. 14, 2008, p. 4233-4245; 13 pages.

Pratima Nangia-Makker et al., "Inhibition of Human Cancer Cell Growth and Metastasis in Nude Mice by Oral Intake of Modified Citrus Pectin", Journal of the National Cancer Institute, vol. 94, No. 24, Dec. 18, 2002; 9 pgs.

Salameh et al., "1H-1,2,3-Triazol-1-yl thiodigalactoside derivatives as high affinity galectin-3 inhibitors", in Bioorg Med Chem, vol. 18, 2010, p. 5367-5378; 13 pages.

Giguère et al., "Inhibitory potential of chemical substitutions at bioinspired sites of β-D-galactopyranose on neoglycoprotein/cell surface binding of two classes of medically relevant lectins", Bioorganic & Medicinal Chemistry, Mar. 9, 2011, vol. 19, No. 10, p. 3280-3287; 8 pages.

Giguère et al., "Carbohydrate triazoles and isoxazoles as inhibitors of galectine-1 and -3", in Chem. Commun., 2006, p. 2379-2381; 3 pages.

Salomonsson et al., "Monovalent interactions of galectin-1", in Biochemistry, vol. 49, 2010, p. 9518-9532; 15 pages.

Denis Giguère et al., "Synthesis of stable and selective inhibitors of human galectins-1 and -3", Bioorganic & Medicinal Chemistry 16 (2008) 7811-7823; 13 pgs.

Pernilla Sörme et al., "Fluorescence polarization as an analytical tool to evaluate galectin-ligand interactions.", Analytical Biochemistry 334 (2004) 36-47; 12 pgs.

Ruud P. M. Dings et al., "Antitumor Agent Calixarene 0118 Targets Human Galectin-1 as an Allosteric Inhibitor of Carbohydrate Binding", Journal of Medicinal Chemistry 2012, 55, 5121-5129; 9 pgs.

Pernilla Sörme et al., "Structural and Thermodynamic Studies on Cation-II Interactions in Lectin-Ligand Complexes: High-Affinity Galectin-3 Inhibitors through Fine-Tuning of an Arginine-Arene Interaction", J. Am. Chem. Soc. 2005, 127, 1737-1743; 7 pgs.

Sörme et al., "Low micromolar inhibitors of galectin-3 based on 3'-derivatization of N-Acetyllactosamine", in ChemBioChem, vol. 3, 2002, p. 183-189; 7 pages.

Sörme et al., "Design and synthesis of galectin inhibitors", in Meth. Enzymol., vol. 363, 2003b, p. 157-169; 13 pages.

Cumpstey et al., "Synthesis of a phenyl thio-β-D-galactopyranoside library from 1,5-difluoro-2,4-dinitrobenzene: discovery of efficient and selective monosaccharide inhibitors of galectin-7", in Org. Biomol. Chem., vol. 3, 2005, p. 1922-1932; 11 pages.

* cited by examiner

GALACTOSIDE INHIBITOR OF GALECTINS

FIELD

The present invention relates to novel compounds, the use of said compounds as medicament and for the manufacture of a medicament for the treatment of cancers; fibrosis; scarring; keloid formation; aberrant scar formation; surgical adhesions; pathological angiogenesis; eye diseases; HIV-1 diseases; inflammation or transplant rejection in mammals. The invention also relates to pharmaceutical compositions comprising said novel compounds.

BACKGROUND

Galectins are proteins with a characteristic carbohydrate recognition domain (CRD) (Leffler et al., 2004). This is a tightly folded β-sandwich of about 130 amino acids (about 15 kDa) with the two defining features 1) a β-galactose binding site and 2) sufficient similarity in a sequence motif of about seven amino acids, most of which (about six residues) make up the β-galactose binding site. However, sites adjacent to the R-galactose site are required for tight binding of natural saccharides and different preferences of these give galectins different fine specificity for natural saccharides.

The recent completion of the human, mouse and rat genome sequences reveal about 15 galectins and galectin-like proteins in one mammalian genome with slight variation between species (Leffler et al., 2004).

Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Lepur et al., 2012). These were the first discovered galectins and are abundant in many tissues.

There are now over 5700 publications on galectins in PubMed, with most, as mentioned above, about galectins-1 (>1400) and -3 (>2800). Strong evidence suggests roles for galectins in e.g. inflammation and cancer, and development (Blidner et al., 2015, Ebrahim et al., 2014).

Galectins are synthesized as cytosolic proteins, without a signal peptide on free ribosomes. Their N-terminus is acetylated, a typical modification of cytosolic proteins, and they reside in the cytosol for a long time (not typical of secreted proteins). From there they can be targeted to the nucleus, specific cytososlic sites, or secreted (induced or constitutively) by a non-classical (non-ER-Golgi) pathway (as first shown for galectin-1 (Cooper and Barondes, 1991)), with as yet unknown mechanism, but possibly similar to the export of e.g. IL-1 (Leffler et al., 2004; Arthur et al., 2015). Galectins can also function in all these compartments; for galectin-1, solid evidence published in well respected journals support roles in RNA splicing in the nucleus, activation of H-RAS in the cytosol, accumulation around disrupted vesicles, and a variety of extracellular effects on cell signaling and adhesion (Elola et al. 2015, Aits et al., 2015, Blanchard et al., 2016). Other galectins also may act in the cytosol by enhancing apoptosis and regulating the cell cycle and differentiation in certain cells. Most galectins act also extracellularly by cross-linking glycoproteins (e.g. laminin, integrins, and IgE receptors) possibly forming supramolecular ordered arrays (Elola et al., 2015) and may thereby modulate cell adhesion and induce intracellular signals. Related to this, recent years have seen the emergence of a molecular mechanism of these galectin functions involving a formation of microdomains (lattices) within membranes, (Elola et al., 2015) which in turn affects intracellular trafficking and cell surface presentation of glycoprotein receptors. This has been documented in cell culture, in null mutant mice, and animals treated with galectin or galectin inhibitors.

Galectin-1, the first discovered and second most studied galectin, is expressed in all tissues with a certain preference but not exclusive for cells of mesenchymal orgin like fibroblasts and lymphocytes. It is involved in the regulation of cell growth, adhesion, signaling, differentiation, development, immune system and host-pathogen interactions (Blanchard et al., 2016). Expression profiles of galectin-1 in the various stages of cancer progression and its role in the tumor microenvironment have been thoroughly reviewed.

Galectin-1 has been implicated in diverse phenomena and, hence, inhibitors may have multiple uses. It is easy to perceive this as a lack of specificity or lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Galectin-1 in Immunity and Inflammation

Galectin-1 has been found mainly to have an immunosuppressive and anti-inflammatory role (Elola et al., 2015), although in some cases it may also be proinflammatory. Galectin-1 binds specific glycosylation pattern on T-helper cells to selectively induce apoptosis in activated Th1 and Th17 cells. (Perillo et. al., 1995) (Toscano, M. A. et al., 2007). The immunosuppressive effect of galectin-1 has suggested that galectin-1 itself, might be a potential treatment for autoimmune and other inflammatory conditions. Conversely, inhibiting its immunosuppressive effect in e.g. cancer has also been proposed as a treatment, as described below.

Galectin-1 in Angiogenesis.

Like galectin-3, galectin-1 has been shown promote angiogenesis under certain circumstances (Hockl et al., 2016) in a way involving its carbohydrate bining-activity. Particularly interesting is the observation that it might promote tumor angiogenesis by a pathway parallel to VEGF. Hence, inhibiting galectin-1 may be anti-angiogenic when inhibition based on anti-VEGF fails. The discovery that the anti-angiogenic peptide Anginex (and related compounds) binds to galectin-1 suggested another mechanism for galectin-1 in angiogensis, but the details remain unclear; Anginex is described as inhibiting galectin-1 activity in some reports, but as enhancing its carbohydrate binding-activities in another.

Galectin-1 in Fibrosis-Related Conditions

The idea of a possible role of galectin-3 in fibrosis comes from cell and ex vivo studies on macrophage differentiation (Mackinnon et al., 2008), as well as from in vivo studies on macrophage differentiation and myofibroblast activation (Mackinnon et al., 2012). Briefly, the hypothesis is as follows: Galectin-3 has been shown to prolong cell surface residence and thus enhance responsiveness of the TGF-β receptor (Partridge et al., 2004), which in turn regulates alternative macrophage differentiation into M2 macrophages and myofibroblast activation. Galectin-1 has also been suggested to a play a role in fibrosis, including by TGF-β related mechanism, but the evidence is less clear than for galectin-3.

Hence, also galectin-1 is a good candidate for being an endogenous enhancer of TGF-β signaling and myofibroblast activation (Kathiriya et al), and galectin-1 inhibitors may be also be useful in treating fibrosis and adverse tissue remodeling.

Galectin-1 in Cancer.

A large number of immunohistochemical studies show changed expression of certain galectins in cancer (van den Brule et. al. and Bidon et al. in Leffler (editor), 2004b) and for example galectin-3 is now an established histochemical marker of thyroid cancer. The direct evidence for a role of galectin-3 in cancer comes from mouse models, mainly by Raz et al, but also others (in Leffler (editor), 2004b). In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. Further, recent evidence have shown that galectin-3 plays a critical role in the tumor microenvironment— reviewed in (Ruvolo, 2015). Galectin-3 is also believed to regulate the interaction between the tumor cells and immune cells, such as T-lymphocytes (T-cells), and inhibition of galectin-3 has been shown to restore T-cell activity (Demotte et al. 2010, Kouo et al. 2015, Melero et al. 2015). From the above it is clear that inhibitors of galectin-3 might have valuable anti-cancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003). More recently, inhibition of galectin-3 with small molecules have been demonstrated to indeed greatly enhance tumor cell sensitivity towards radiation and standard pro-apoptotic drugs in cell assays and ex vivo (Lin et al., 2009), as well as in vivo (Glinsky et al., 2009).

Also galectin-1 is frequently over-expressed in low differentiated cancer cells, and galectin-9 or its relatives galectin-4 and galectin-8 may be induced in specific cancer types (Huflejt and Leffler, 2004; Leffler (editor), 2004b). Galectin-1 induces apoptosis in activated T-cells and has a remarkable immunosuppressive effect on autoimmune disease in vivo (Rabinovich et al; and Pace et al. in Leffler (editor), 2004b). Therefore, the over-expression of these galectins in cancers might help the tumor to defend itself against the T-cell response raised by the host.

Null mutant mice for galectins-1 and -3 have been established many years ago (Poirier, 2002). These are healthy and reproduce apparently normally in animal house conditions. However, recent studies have revealed subtle phenotypes in function of neutrophils and macrophages (as described above) and in bone formation for galectin-3 null mutants, and in nerve and muscle cell regeneration/differentiation for the galectin-1 null mutants (Leffler et al., 2004; Poirier, 2002; Watt in Leffler (editor), 2004b). Recently galectin-7 and galectin-9 null mutant mice have been generated and are also grossly healthy in animal house conditions, but have not yet been analyzed in detail. The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null mutant mice may make galectin inhibitors more favorable as drugs. If galectin activity contributes to pathological conditions as suggested above but less to normal conditions, then inhibition of them will have less unwanted side effects.

Thus drugs targeting galectin-1 activities in cancer such as suppressingimmunity or enhancing angiogenesis may become useful anti-cancer treatments.

Known Inhibitors

Natural Ligands

Solid phase binding assays and inhibition assays have identified a number of saccharides and glycoconjugates with the ability to bind galectins (reviewed by Leffler, 2001, Leffler et al., 2004). All galectins bind lactose with a $K_d$ of about 0.1-1 mM. The affinity of D-galactose is 50-100 times lower. N-Acetyllactosamine and related disaccharides bind about as well as lactose, but for certain galectins, they can bind either worse or up to 10 times better. Galactose (10 mM) (Tejler et. al. 2009) and Lactose (190 μM) (van Hattum, 2013) both have low affinity to Galectin-1.

The above-described natural saccharides that have been identified as galectin-1 ligands are not suitable for use as active components in pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.

Galectin Specificity

The studies of galectin specificity using inhibition by small natural saccharides mentioned above indicated that all galectins bound lactose, LacNAc and related disaccharides, but that galectin-3 bound certain longer saccharides much better (Leffler and Barondes, 1986). These longer saccharides were characterized by having an additional sugar residue added to the C-3 position of galactose (in e.g. lactose or LacNAc) that bound an extended binding groove. The shape of this groove varies between galectins, suggesting that the same extensions would not be bound equally by the different galectins.

Synthetic Inhibitors

A patent review covering galectin-1 inhibitors and their potential as therapeutics were recently published. (Blanchard 2016). The small molecule monosacharides covered in this review have been reported as having galectin-1 affinity which is at best similar to lactose. Disaccharides on the other hand, in particular thiodigalactosides (TDG), has been reported to have high affinity towards galectin-1. (T. Delaine, 2016, ChemBioChem 10.1002/cbic.201600285)

Saccharides coupled to amino acids with anti-cancer activity were first identified as natural compounds in serum, but subsequently, synthetic analogues have been made (Glinsky et al., 1996). Among them, those with lactose or galactose coupled to the amino acid inhibit galectins, but only with about the same potency as the corresponding underivatized sugar. Chlorinconjugated lactose have been reported to have high affinity (0.54 μM) as measured in an Elisa assay. (Pandey et. al. 2002, in EP1256586 (A1)). A chemically modified form of citrus pectin (Platt and Raz, 1992) that inhibits galectin-3 shows anti-tumor activity in vivo (Pienta et al., 1995; Nangia-Makker et al., 2002). Cluster molecules having up to four lactose moieties showed a strong multivalency effect when binding to galectin-3, but not to galectin-1 and galectin-5 (Vrasidas et al., 2003).

Cyclodextrin-based glycoclusters with seven galactose, lactose, or N-acetyllactosamine residues also showed a strong multivalency effect against galectin-3, but less so against galectins-1 and -7 (André et al., 2004). Starburst dendrimers (Andre et al., 1999) and glycopolymers (Pohl et al., 1999; David et al., 2004), made polyvalent in lactose-residues, have been described as galectin-3 inhibitors with marginally improved potency as compared to lactose. Multivalent lactose derivatives have been shown to have a pronounced cluster effect towards galectin-1 (Tejler et. al., 2006). In addition, these compounds were selective over other galectins. Peptide based compounds such as Anginex and non-peptidic topomimetics (Dings et. al. 2012) have been reported to be allosteric galectin-1 inhibitors. The aforementioned synthetic compounds that have been identified as galectin-1 ligands are not suitable for use as active components in pharmaceutical compositions, because they are hydrophilic in nature and are not readily absorbed from the gastrointestinal tract following oral administration. In addition the aforementioned compounds have moderate affinity and selectivity.

Natural oligosaccharides, glycoclusters, glycodendrimers, peptides, non-peptidic topomimetics and glycopolymers described above are too polar and too large to be absorbed and in some cases are large enough to produce immune responses in patients. Furthermore, they are susceptible to acidic hydrolysis in the stomach and to enzymatic hydrolysis. Thus, there is a need for small synthetic molecules.

Thiodigalactoside is known to be a synthetic and hydrolytically stable, yet polar inhibitor, approximately as efficient as N-acetyllactosamine (Leffler and Barondes, 1986). N-Acetyllactosamine derivatives carrying aromatic amides or substituted benzyl ethers at C-3' have been demonstrated to be highly efficient inhibitors of galectin-3, with unprecedented $IC_{50}$ values as low as 4.8 µM, which is a 20-fold improvement in comparison with the natural N-acetyllactosamine disaccharide (Sörme et al., 2002; Sörme et al., 2003b, 2005). These derivatives are less polar overall, due to the presence of the aromatic amido moieties and are thus more suitable as agents for the inhibition of galectins in vivo. Furthermore, C3-triazolyl galactosides have been demonstrated to be as potent inhibitors as the corresponding C3-amides of some galectins. Hence, any properly structured galactose C3-substituent may confer enhanced galectin affinity.

However, the C3-amido- and C3-triazolyl-derivatised compounds are still susceptible to hydrolytic degradation in vivo, due to the presence of a glycosidic bond in the galactose and N-acetyllactosamine saccharide moiety and, although they are potent small molecule inhibitors of galectin-3, even further improved affinity and stability is desirable. Accordingly, inhibitors based on 3,3'-diamido- or 3,3'-ditriazolyl-derivatization of thiodigalactoside have been developed, (Cumpstey et al., 2005b; Cumpstey et al., 2008; Salameh et al., 2010; WO/2005/113569 and US2007185041; WO/2005/113568, U.S. Pat. No. 7,638,623 B2; T. Delaine, 2016, ChemBioChem 10.1002/cbic.201600285) which lack O-glycosidic hydrolytically and enzymatically labile linkages. These inhibitors also displayed superior affinity for several galectins (down to Kd in the low nM range). Nevertheless, although displaying high affinity for galectins, the 3,3'-derivatized thiodigalactosides still comprise a disadvantage in their multistep synthesis involving double inversion reaction to reach at 3-N-derivatized galactose building blocks. Furthermore, cyclohexane replacement of one galactose ring in thiodigalactoside has been evidenced to mimic the galactose ring and hence to provide galectin-1 and -3 inhibitors with efficiency approaching those of the diamido- and ditriazolyl-thiodigalactoside derivatives (WO/2010/126435). Replacement of a D-galactopyranose unit with a substituted cyclohexane decreases polarity and most likely also metabolic susceptibility, thus improving drug-like properties.

Some earlier described compounds have the following general formulas

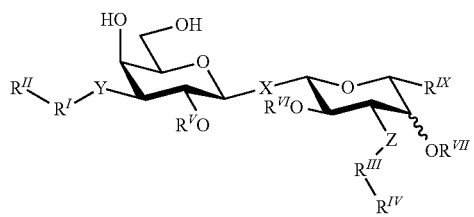

as described in WO/2005/113568,
and

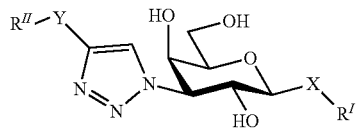

as described in WO/2005/113569, in which $R^I$ can be a D-galactose.

In recently published (T. Delaine, 2016, ChemBioChem 10.1002/cbic.201600285) is disclosed a

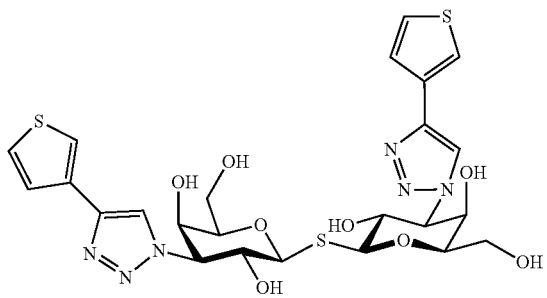

TDG substituted with a thiophene triazole substituent in the C3 and C3' positions with high affinity (<10 nM) to Galectin-1.

In recently published US20140099319, WO2014067986 and T. Delaine, 2016, ChemBioChem 10.1002/cbic.201600285, is disclosed a compound

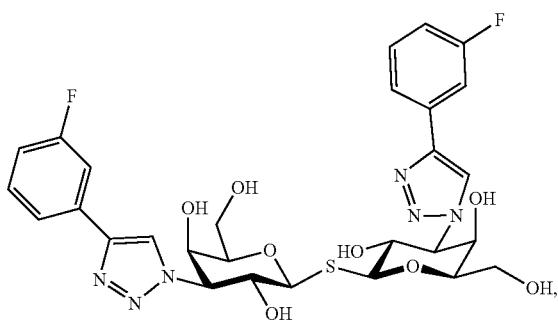

having fluorine (F) in the meta position on both the phenyl rings in relation to the triazole rings. This compound has been shown to be a promising drug candidate for lung fibrosis, and in particular is very selective on galectin-3 with high affinity.

A series of small C1 or C1 and C3-substituted galactopyranosides have been disclosed showing affinity towards galectin-3 and 1. The beta-D-galactopyranosides were reported as having affinity in the same range or less than lactose, which has a Kd of about 91 μM towards galectin 3 and 190 μM towards galectin 1. (Giguere, D et. al. 2011, 2008, 2006).

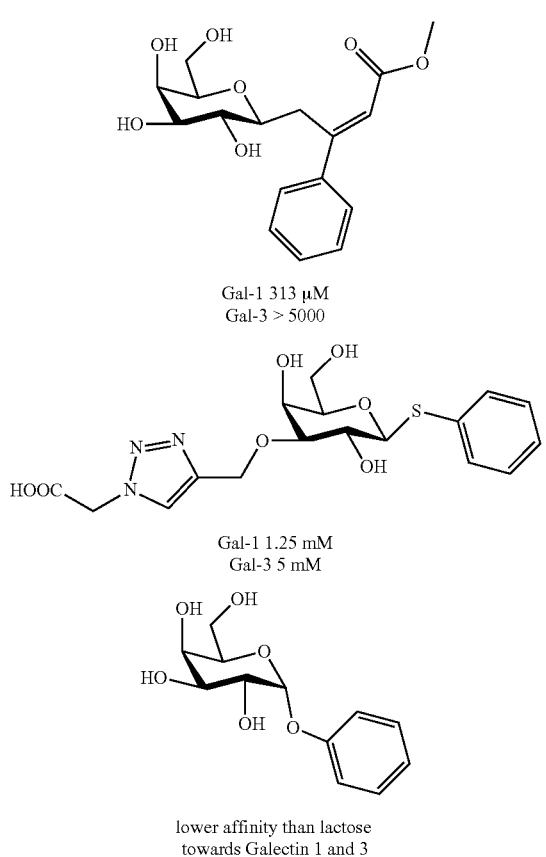

Gal-1 313 μM
Gal-3 > 5000

Gal-1 1.25 mM
Gal-3 5 mM lower affinity than lactose
towards Galectin 1 and 3

There is no disclosure or mentioning of corresponding alpha-anomers having affinity towards galectin-1 or galectin-3 better than lactose.

SUMMARY

The compounds of the present invention are novel α-D-galactopyranose compounds that unexpectedly have shown high affinity for galectin-1, and some have also high affinity to gaslectin-3, and are considered novel potent drug candidates. Some of the compounds have high affinity to galectin-1 and are also specific to galectin-1.

In broad aspect the present invention concerns a D-galactopyranose compound of formula (1)

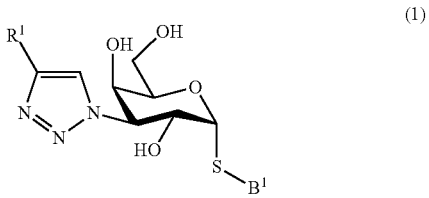

(1)

wherein the pyranose ring is α-D-galactopyranose,
R$^1$ is selected from the group consisting of

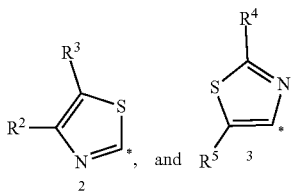

wherein the asterix * indicates the carbon atom of the heteroaromatic ring that is covalently attached to the triazole group of formula (1);

wherein R$^2$ is selected from the group consisting of OH and halogen, preferably F, Cl and Br;

R$^3$ is selected from the group consisting of hydrogen, C$_{1-6}$ alkyl and halogen;

R$^4$ is selected from the group consisting of OH and halogen, preferably F, Cl, and Br;

R$^5$ is selected from the group consisting of hydrogen, C$_{1-6}$ alkyl and halogen;

B$^1$ is selected from a) an aryl, such as phenyl or naphthyl, optionally substituted with a group selected from a halogen; CN; —COOH; —CONR$^{29}$R$^{30}$, wherein R$^{29}$ and R$^{30}$ are independently selected from H, C$_{1-3}$ alkyl, cyclopropyl, and iso-propyl; C$_{1-3}$ alkyl, optionally substituted with a F; cyclopropyl, optionally substituted with a F; isopropyl, optionally substituted with a F; OC$_{1-3}$ alkyl, optionally substituted with a F; SC$_{1-3}$ alkyl, optionally substituted with a F; O-cyclopropyl, optionally substituted with a F; O-isopropyl, optionally substituted with a F; NR$^{31}$R$^{32}$, wherein R$^{31}$ and R$^{32}$ are independently selected from H, C$_{1-3}$ alkyl and isopropyl; OH; and R$^{33}$—CONH—, wherein R$^{33}$ is selected from C$_{1-3}$ alkyl and cyclopropyl; b) a heterocycle, such as heteroaryl or heterocycloalkyl, optionally substituted with a group selected from a halogen; CN; —COOH; —CONR$^{35}$R$^{36}$, wherein R$^{35}$ and R$^{36}$ are independently selected from H, C$_{1-3}$ alkyl, cyclopropyl, and iso-propyl; C$_{1-3}$ alkyl, optionally substituted with a F; cyclopropyl, optionally substituted with a F; isopropyl, optionally substituted with a F; OC$_{1-3}$ alkyl, optionally substituted with a F; SC$_{1-3}$ alkyl, optionally substituted with a F; O-cyclopropyl, optionally substituted with a F; O-isopropyl, optionally substituted with a F; $NR^{37}R^{38}$, wherein $R^{37}$ and $R^{38}$ are independently selected from H, $C_{1-3}$ alkyl and isopropyl; OH; and $R^{39}$—CONH— wherein $R^{39}$ is selected from $C_{1-3}$ alkyl and cyclopropyl; or a pharmaceutically acceptable salt or solvate thereof.

In an embodiment $R^1$ is selected from formula 2 wherein $R^2$ is selected from the group consisting of OH and halogen; and $R^3$ is selected from the group consisting of hydrogen, $C_{1-6}$ alkyl and halogen. In a preferred embodiment $R^2$ is OH, and $R^3$ is H. Depending on conditions such as acidic or basic the OH group maybe on the oxo tautomer form. In another preferred embodiment $R^2$ is halogen, and $R^3$ is selected from the group consisting of hydrogen and halogen.

In a still further embodiment $R^1$ is selected from formula 3 wherein $R^4$ is selected from the group consisting of OH and halogen; and $R^5$ is selected from the group consisting of hydrogen, $C_{1-6}$ alkyl and halogen. In a preferred embodiment $R^4$ is OH and $R^5$ is selected from the group consisting of hydrogen, $C_{1-6}$ alkyl and halogen. In another preferred embodiment $R^4$ is halogen and $R^5$ is selected from the group consisting of hydrogen, $C_{1-6}$ alkyl and halogen.

In a further embodiment $B^1$ is selected from a pyridinyl substituted with one, or two substituents selected from Cl, Br, isopropyl, COOH, $CONH_2$, CN and $CF_3$. In a further embodiment $B^1$ is selected from phenyl optionally substituted with a group selected from halogen, $SC_{1-3}$ alkyl, optionally substituted with a F; $C_{1-6}$ alkyl and CN.

In a still further embodiment $B^1$ is selected from a phenyl substituted with one, two or three substituents selected from Cl, F, Br, $CF_3$, $SCF_3$, $CH_3$ and CN.

In a further embodiment $B^1$ is selected from a phenyl substituted with one, two or three substituents selected from Cl, F, Br, $CF_3$, $SCF_3$, $CH_3$, $CON(CH_3)_2$ and CN.

In a still further embodiment $B^1$ is selected from a pyridinyl, optionally substituted with a group selected from a halogen; —COOH; —$CONR^{35}R^{36}$, wherein $R^{35}$ and $R^{36}$ are independently selected from H, $C_{1-3}$ alkyl, cyclopropyl, and iso-propyl; isopropyl, optionally substituted with a F; CN; and a methyl optionally substituted with a F.

In a further embodiment $B^1$ is selected from a pyridinyl substituted with one, or two substituents selected from Cl, Br, isopropyl, COOH, $CONH_2$, CN and $CF_3$.

In a further embodiment $B^1$ is selected from a pyridinyl substituted with one, or two substituents selected from the group consisting of Cl, Br, isopropyl, COOH, $CONH_2$, CN, $CON(CH_3)_2$ and $CF_3$.

In a further embodiment the compound of formula (1) is selected from any one of:

5-Bromo-6-trifluoromethyl-pyridine-3-yl 3-[4-(4-chlorothiazol-2-yl)-1H-1,2,3-triazol-1-yl]-3-deoxy-1-thio-α-D-galactopyranoside, 5-Bromo-6-trifluoromethyl-pyridine-3-yl 3-[4-(4-bromothiazol-2-yl)-1H-1,2,3-triazol-1-yl]-3-deoxy-1-thio-α-D-galactopyranoside, 5-Chloro-6-cyano-pyridine-3-yl 3-[4-(4-chlorothiazol-2-yl)-1H-1,2,3-triazol-1-yl]-3-deoxy-1-thio-α-D-galactopyranoside, 5-Bromo-2-cyano-pyridine-3-yl 3-[4-(4-chlorothiazol-2-yl)-1H-1,2,3-triazol-1-yl]-3-deoxy-1-thio-α-D-galactopyranoside, 5-Chloro-2-cyano-pyridine-3-yl 3-[4-(4-chlorothiazol-2-yl)-1H-1,2,3-triazol-1-yl]-3-deoxy-1-thio-α-D-galactopyranoside, 5-Bromo-6-cyano-3-pyridyl 3-[4-(4-chlorothiazol-2-yl)-1H-1,2,3-triazol-1-yl]-3-deoxy-1-thio-α-D-galactopyranoside, 3,4-Dichlorophenyl 3-[4-(2-chlorothiazol-4-yl)-1H-1,2,3-triazol-1-yl]-3-deoxy-1-thio-α-D-galactopyranoside, 3,4-Dichlorophenyl 3-deoxy-3-[4-(2-fluorothiazol-4-yl)-1H-1,2,3-triazol-1-yl]-1-thio-α-D-galactopyranoside, 3,4-Dichlorophenyl 3-deoxy-3-[4-(4-fluorothiazol-2-yl)-1H-1,2,3-triazol-1-yl]-1-thio-α-D-galactopyranoside, 3,4-Dichlorophenyl 3-deoxy-3-[4-(4,5-difluorothiazol-2-yl)-1H-1,2,3-triazol-1-yl]-1-thio-α-D-galactopyranoside, 3,4-Dichlorophenyl 3-deoxy-3-[4-(4-hydroxythiazol-2-yl)-1H-1,2,3-triazol-1-yl]-1-thio-α-D-galactopyranoside, 3,4-Dichlorophenyl 3-deoxy-3-[4-(2-hydroxythiazol-4-yl)-1H-1,2,3-triazol-1-yl]-1-thio-α-D-galactopyranoside, 5-Chloro-6-cyano-pyridine-3-yl 3-deoxy-3-[4-(2-hydroxythiazol-4-yl)-1H-1,2,3-triazol-1-yl]-1-thio-α-D-galactopyranoside, 5-Bromo-2-cyano-pyridine-3-yl 3-deoxy-3-[4-(2-hydroxythiazol-4-yl)-1H-1,2,3-triazol-1-yl]-1-thio-α-D-galactopyranoside, 5-Bromo-6-cyano-3-pyridyl 3-deoxy-3-[4-(2-hydroxythiazol-4-yl)-1H-1,2,3-triazol-1-yl]-1-thio-α-D-galactopyranoside, 5-Chloro-2-cyano-3-pyridyl 3-deoxy-3-[4-(2-hydroxythiazol-4-yl)-1H-1,2,3-triazol-1-yl]-1-thio-α-D-galactopyranoside, 5-Chloro-6-trifluoromethyl-pyridin-3-yl 3-deoxy-3-[4-(2-hydroxythiazol-4-yl)-1H-1,2,3-triazol-1-yl]-1-thio-α-D-galactopyranoside, 3,5-dichloro-4-fluoro-phenyl 3-deoxy-3-[4-(2-hydroxythiazol-4-yl)-1H-1,2,3-triazol-1-yl]-1-thio-α-D-galactopyranoside, 3-Chloro-4-fluoro-phenyl 3-deoxy-3-[4-(2-hydroxythiazol-4-yl)-1H-1,2,3-triazol-1-yl]-1-thio-α-D-galactopyranoside, 3,4,5-trichlorophenyl 3-deoxy-3-[4-(2-hydroxythiazol-4-yl)-1H-1,2,3-triazol-1-yl]-1-thio-α-D-galactopyranoside, 3,5-dibromo-4-fluorophenyl 3-deoxy-3-[4-(2-hydroxythiazol-4-yl)-1H-1,2,3-triazol-1-yl]-1-thio-α-D-galactopyranoside, 3-Bromo-4-cyanophenyl 3-deoxy-3-[4-(2-hydroxythiazol-4-yl)-1H-1,2,3-triazol-1-yl]-1-thio-α-D-galactopyranoside, 5-Bromo-6-trifluoromethyl-3-pyridyl 3-deoxy-3-[4-(2-hydroxythiazol-4-yl)-1H-1,2,3-triazol-1-yl]-1-thio-α-D-galactopyranoside, 3-Chloro-4-trifluoromethylphenyl 3-deoxy-3-[4-(2-hydroxythiazol-4-yl)-1H-1,2,3-triazol-1-yl]-1-thio-α-D-galactopyranoside, 3-Chloro-4-trifluoromethylthiophenol 3-deoxy-3-[4-(2-hydroxythiazol-4-yl)-1H-1,2,3-triazol-1-yl]-1-thio-α-D-galactopyranoside, 3-Chloro-4-methylphenyl 3-deoxy-3-[4-(2-hydroxythiazol-4-yl)-1H-1,2,3-triazol-1-yl]-1-thio-α-D-galactopyranoside, 5-Chloro-picolinamide-3-yl 3-[4-(4-chlorothiazol-2-yl)-1H-1,2,3-triazol-1-yl]-3-deoxy-1-thio-α-D-galactopyranoside, 2-Carboxy-5-chloropyridyl 3-deoxy-3-[4-(2-hydroxythiazol-4-yl)-1H-1,2,3-triazol-1-yl]-1-thio-α-D-galactopyranoside, 5-Bromo-6-trifluoromethyl-pyridine-3-yl 3-deoxy-3-[4-(4,5-dichlorothiazol-2-yl)-1H-1,2,3-triazol-1-yl]-1-thio-α-D-galactopyranoside, 5-Bromo-2-isopropyl-pyridine-3-yl 3-[4-(4-chlorothiazol-2-yl)-1H-1,2,3-triazol-1-yl]-3-deoxy-1-thio-α-D-galactopyranoside, 3,4-Dichloro-6-fluoro-phenyl 3-deoxy-3-[4-(2-hydroxythiazol-4-yl)-1H-1,2,3-triazol-1-yl]-1-thio-α-D-galactopyranoside, 4-Chloro-N,N'-dimethylbenzamide-2-yl 3-deoxy-3-[4-(2-hydroxythiazol-4-yl)-1H-1,2,3-triazol-1-yl]-1-thio-α-D-galactopyranoside, 5-Chloro-N,N'-dimethyl-picolinamide-3-yl 3-deoxy-3-[4-(2-hydroxythiazol-4-yl)-1H-1,2,3-triazol-1-yl]-1-thio-α-D-galactopyranoside; or a pharmaceutically acceptable salt or solvate thereof.

In a further aspect the present invention relates to a compound of formula (1) for use as a medicine.

In a still further aspect the present invention relates to a pharmaceutical composition comprising the compound of any one of the previous claims and optionally a pharmaceutically acceptable additive, such as a carrier and/or excipient.

In a further aspect the present invention relates to a compound of formula (1) of the present invention for use in a method for treating a disorder relating to the binding of a galectin-1 to a ligand in a mammal, such as a human. In a further embodiment the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; scleroderma; sclerosis; surgical adhesions; septic shock; cancer, such as carcinomas, sarcomas, leukemias and lymphomas, such as T-cell lymphomas; metastasising cancers; neovascularization related to cancer; autoimmune diseases, such as psoriasis, rheumatoid arthritis, Crohn's disease, ulcerative colitis, ankylosing spondylitis, systemic lupus erythematosus; transplant rejection; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; obesity; asthma and other interstitial lung diseases, including Hermansky-Pudlak syndrome, mesothelioma; liver disorders, such as non-alcoholic steatohepatitis.

In a still further aspect the present invention relates to a method for treatment of a disorder relating to the binding of a galectin-1 to a ligand in a mammal, such as a human, wherein a therapeutically effective amount of at least one compound of formula (1) of the present invention is administered to a mammal in need of said treatment. In a further embodiment the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; scleroderma; sclerosis; surgical adhesions; septic shock; cancer, such as carcinomas, sarcomas, leukemias and lymphomas, such as T-cell lymphomas; metastasising cancers; neovascularization related to cancer; autoimmune diseases, such as psoriasis, rheumatoid arthritis, Crohn's disease, ulcerative colitis, ankylosing spondylitis, systemic lupus erythematosus; transplant rejection; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; obesity; asthma and other interstitial lung diseases, including Hermansky-Pudlak syndrome, mesothelioma; liver disorders, such as non-alcoholic steatohepatitis.

Another aspect of the present invention concerns combination therapy involving administering a compound of formula (1) of the present invention together with a therapeutically active compound different from the compound of formula (1) (interchangeable with "a different therapeutically active compound"). In one embodiment, the present invention relates to a combination of a compound of formula (1) and a different therapeutically active compound for use in treatment of a disorder relating to the binding of a galectin-1 to a ligand in a mammal. Such disorders are disclosed below.

In an embodiment of the present invention, a therapeutically effective amount of at least one compound of formula (1) of the present invention is administered to a mammal in need thereof in combination with a different therapeutically active compound. In a further embodiment, said combination of a compound of formula (1) together with a different therapeutically active compound is administered to a mammal suffering from a disorder selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; scleroderma; sclerosis; surgical adhesions; septic shock; cancer, such as carcinomas, sarcomas, leukemias and lymphomas, such as T-cell lymphomas; metastasising cancers; neovascularization related to cancer; autoimmune diseases, such as psoriasis, rheumatoid arthritis, Crohn's disease, ulcerative colitis, ankylosing spondylitis, systemic lupus erythematosus; transplant rejection; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; obesity; asthma and other interstitial lung diseases, including Hermansky-Pudlak syndrome, mesothelioma; liver disorders, such as non-alcoholic steatohepatitis.

A non-limiting group of cancers given as examples of cancers that may be treated, managed and/or prevented by administration of a compound of formula (1) in combination with a different therapeutically active compound is selected from: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, cholangiocarcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In some aspects of the present invention, the administration of at least one compound of formula (1) of the present invention and at least one additional therapeutic agent demonstrates therapeutic synergy. In some aspects of the methods of the present invention, a measurement of response to treatment observed after administering both at least one compound of formula (1) of the present invention and the additional therapeutic agent is improved over the same measurement of response to treatment observed after administering either the at least one compound of formula (1) of the present invention or the additional therapeutic agent alone.

A further aspect of the present invention concerns combination therapy involving administering a compound of formula (1) of the present invention together with an anti-fibrotic compound different form the compound of formula (1) to a mammal in need thereof. In a further embodiment, such anti-fibrotic compound may be selected from the following non-limiting group of anti-fibrotic compounds: pirfenidone, nintedanib, simtuzumab (GS-6624, AB0024), BG00011 (STX100), PRM-151, PRM-167, PEG-FGF21, BMS-986020, FG-3019, MN-001, IW001, SAR156597, GSK2126458, and PBI-4050.

A still further aspect of the present invention concerns combination therapy involving administering a compound of formula (1) in combination with a further conventional cancer treatment such as chemotherapy or radiotherapy, or treatment with immunostimulating substances, gene therapy, treatment with antibodies, vaccines and cellular therapies including e.g. dendritic cells, haematopoetic stem cells and adoptive T cell transfer, to a mammal in need thereof.

In an embodiment, the compound of formula (1) is administered together with at least one additional therapeutic agent selected from an antineoplastic chemotherapy agent. In a further embodiment, the antineoplastic chemotherapeutic agent is selected from: all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine. In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

In a further embodiment of the present invention, the further conventional cancer treatment includes radiation therapy. In some embodiments, radiation therapy includes localized radiation therapy delivered to the tumor. In some embodiments, radiation therapy includes total body irradiation.

In other embodiments of the present invention the further cancer treatment is selected from the group of immunostimulating substances e.g. cytokines and antibodies. Such cytokines may be selected from the group consisting of, but not limited to: GM-CSF, type I IFN, interleukin 21, interleukin 2, interleukin 12 and interleukin 15. The antibody is preferably an immunostimulating antibody such as anti-CD40 or anti-CTLA-4 antibodies. The immunostimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

In some embodiments of the present invention the compound of formula (1) is administered together with at least one additional therapeutic agent selected from the class of immune checkpoint inhibitors*. In some embodiments of the invention, the checkpoint inhibitor is acting on one or more of the following, non-limiting group of targets: CEACAM1, galectin-9, TIM3, CD80, CTLA4, PD-1, PD-L1, HVEM, BTLA, CD160, VISTA, B7-H4, B7-2, CD155, CD226, TIGIT, CD96, LAG3, GITF, OX40, CD137, CD40, IDO, and TDO. These are known targets and some of these targets are described in Melero et al., Nature Reviews Cancer (2015).

In some embodiments of the present invention the compound of formula (1) is administered together with at least one additional therapeutic agent selected from an inhibitor of indoleamine-2,3-dioxygenase (IDO).

In some embodiments of the present invention the compound of formula (1) is administered together with at least one additional therapeutic agent selected from one or more inhibitors of the CTLA4 pathway. In some embodiments, the inhibitor of the CTLA4 pathway is selected from one or more antibodies against CTLA4.

In some embodiments of the present invention the compound of formula (1) is administered together with at least one additional therapeutic agent selected from one or more inhibitors of the PD-1/PD-L pathway. In some embodiments, the one or more inhibitors of the PD-1/PD-L pathway are selected from one or more antibodies against PD-1, PD-L1, and/or PD-L2.

In a still further aspect the present invention relates to a process of preparing a compound of formula III or a pharmaceutically acceptable salt or solvate thereof comprising the step a1 where B1 and $R^1$ are defined as above under formula 1;

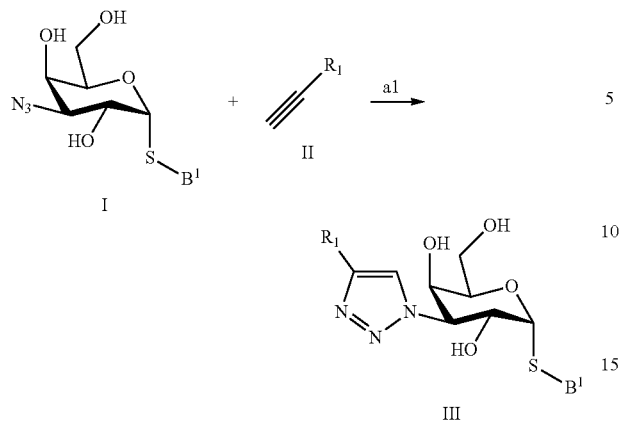

a1) Reacting the compound of formula I with a compound of formula II in an inert solvent, such as DMF or acetonitrile, using a base, such as diisopropylethylamine, catalyzed by CuI to provide the compound of the formula III.

In a still further aspect the present invention relates to a process of preparing a compound of formula V or a pharmaceutically acceptable salt or solvate thereof comprising the step a1 where X, B1 and $R^5$ are defined as above under formula 1;

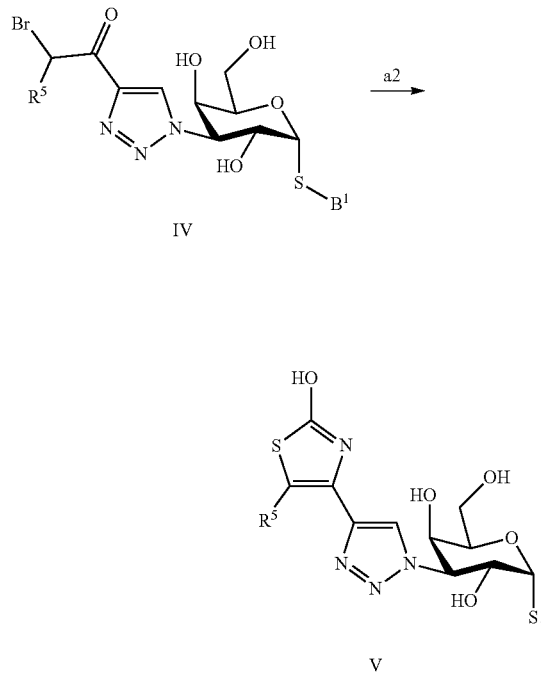

a2) Reacting a compound of formula IV with a compound of the formula HOC(=S)NH$_2$ in the presence of silver trifluoromethanesulfonate in an inert solvent such as ethyl acetate to provide a compound of the formula V.

In a still further aspect the present invention relates to a process of preparing a compound of formula IX where $B^1$ is defined as above under formula 1 or a pharmaceutically acceptable salt or solvate thereof comprising the steps a3 and a4;

a3) Reacting a compound VI with a chlorinating reagent such as dichloromethylmethylether or PCl$_5$ in the presence of a lewis acid such as BF$_3$ Et$_2$O in an inert solvent such as dichloromethane or chloroform to give a compound of formula VII.

a4) Reacting a compound of the formula VII with a nucleophile like VIII in the presence of a base like sodium hydride in an inert solvent such as DMF to give a compound of formula IX.

In a still further aspect the present invention relates to a process of preparing a compound of formula XII wherein X is defined as sulfur and $B^1$ defined as formula 1 or a pharmaceutically acceptable salt or solvate thereof comprising the steps a5 and a6;

a5) Reacting a compound of formula X with a sulfurus nucleophile such as potassium thioacetate to give compound XI in an inert solvent such as DMF.

a6) Reacting a compound of the formula XI with a compound of the formula $B^1$-L, wherein L is defined as a leaving group such as Fluorine, Chlorine or Bromine, in an inert solvent as DMF using a base such as dimethylamine to give a compound of the formula XII.

In a still further aspect the present invention relates to a process of preparing a compound of the formula VIII comprising step a7-a8, wherein $B^1$ is defined as above under formula (1);

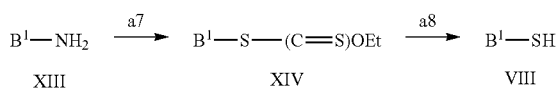

a7) A compound of the formula XIII could upon treatment with sodium nitrite form the corresponding diazocompound. This compound could be further reacted with a sulfurus source such as potassium ethyl xantogenate to form a compound of the formula XIV.

a8) Reacting a compound of formula XIV with a base such as potassium hydroxide to give a compound of formula VIII.

In a still further aspect the present invention relates to a process of preparing a compound of the formula VIII comprising step a9, wherein $B^1$ is defined as above under formula (1);

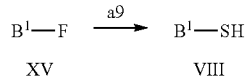

a9) Reacting a compound of the formula XV with $Na_2S.10H_2O$ in the presence of a base such as NaOH in an inert solvent such as DMF to give a compound of formula VIII.

In a still further aspect the present invention relates to a process of preparing a compound of the formula XI comprising step a10-a12, wherein $B^1$ is defined as above under formula (1);

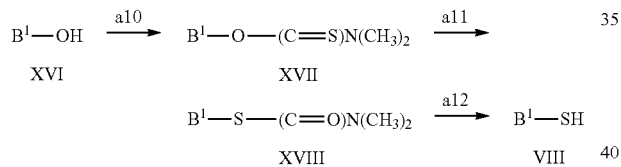

a10) Reacting a compound of the formula XVI with an activated thioamide such as dimethylcarbamoyl chloride using a base such as sodium hydride in an inert solvent such as DMF to give a compound of formula XVII.

a11) Heating a compound of the formula XVII at elevated temperatures to form compound XVIII.

a12) Reacting a compound of formula XVIII with a base such as potassium hydroxide to give a compound of the formula VIII.

In a still further aspect the present invention relates to a process of preparing a compound of formula II comprising the step a13 wherein $R^1$ is defined as above under formula (1):

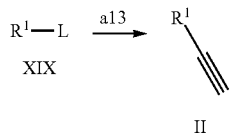

a12) Reacting a compound of formula XIX wherein L is defined as a leaving group such as chlorine or bromine with trimethylsilane-acetylene using a palladium catalyst such as bis(triphenylphosphine)palladium-(II)-chloride, copper iodide and a base like diisopropylethylamine in an inert solvent, such as tetrahydrofuran (THF), to give a compound of formula II.

In a still further aspect the present invention relates to a process of preparing a compound of the formula IV comprising step a14-a16, wherein $B^1$ and $R^4$ are defined as above under formula (1);

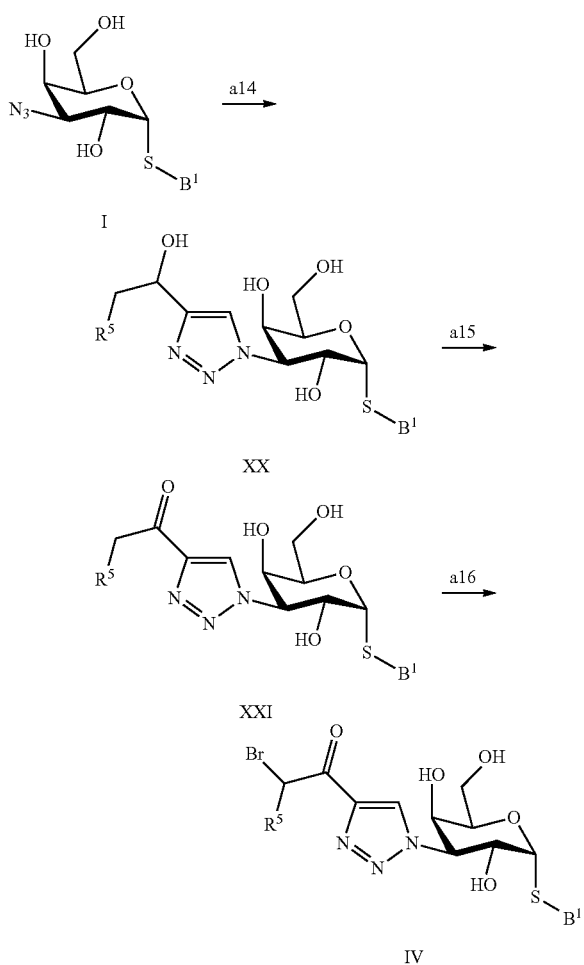

a14) Reacting a compound of formula I with a compound of formula $R^4$—$CH_2CHOH$—CC—H to give a compound of formula XX, using CuI in an inert solvent such as DMF or acetonitrile, using a base, such as diisopropylethylamine.

a15) Reacting a compound of formula XX with an oxidizing reagent such as Dess-Martin periodinane in an inert solvent such as DCM to give a compound of formula XXI.

a16) Introduction of bromine by reacting a compound of the formula XXI first with TBSOTf in the presence of a base such as TEA in an inert solvent such as DCM, to give an intermediate which is further reacted with NBS in an inert solvent such as THF to give a compound of formula IV.

In a still further aspect the present invention relates to a process of preparing a compound of the formula XXIII comprising step a17;

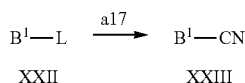

a17) Reacting a compound of the formula XXII, wherein B¹ is defined as above and L is a leaving group such as Bromine, with CuCN in an inert solvent such as dimethylformamide, optionally at elevated temperatures, to give a compound of formula XXIII.

In a still further aspect the present invention relates to a process of preparing a compound of the formula XXV comprising step a18;

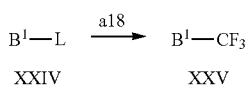

a18) Reacting a compound of the formula XXIV, wherein B¹ is defined as above and L is a leaving group such as Iodine, with KF and CuI, optionally at elevated temperatures to give an intermediate which is further reacted with trimethyl (trifluoromethyl)silane to give an intermediate which is dissolved in an inert solvent such as 1-Methyl-2-pyrrolidinone (NMP) and added 3,5-dichloro-2-iodopyridine to give a compound of formula XXV.

In a still further aspect the present invention relates to a process of preparing a compound of the formula XXVII comprising step a19;

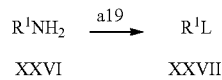

a20) Reacting a compound of the formula XXVI wherein R¹ is defined as above with isoamylnitrite followed by reaction with CuL, wherein L is defined as a halogen like chlorine or bromine to give a compound for formula XXVII.

In a still further aspect the present invention relates to a process of preparing a compound of the formula XXXII comprising step a20;

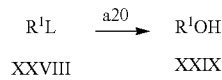

a20) Reacting a compound of the formula XXVIII with water or a protected hydroxygroup such as bensyloxy to give a compound of the formula XXIX in the presencence of a base such as Sodium Hydride.

In a still further aspect the present invention relates to a process of preparing a compound of the formula XXXIV comprising step a21;

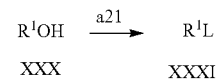

a21) Reacting a compound of the formula XXXIII wherein R¹ is defined as above with a halogenating compound such as of the formula POL₃, wherein L is defined as a halogen like fluorine, chlorine or bromine (e.g. POCl₃) to give a compound for formula XXXI.

In a still further aspect the present invention relates to a process of preparing a compound of the formula XXXIV comprising step a22-a23;

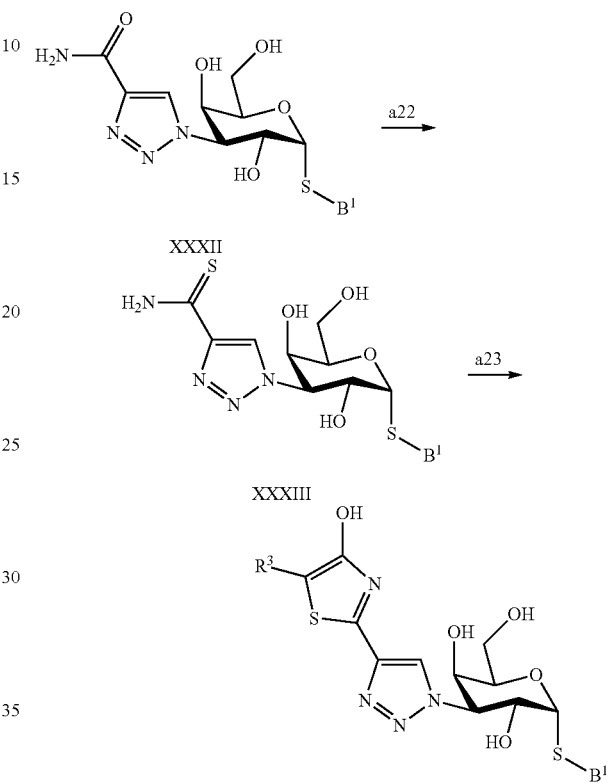

a22) Reacting a compound of the formula XXXII with a reagent such a Lawessons reagent to give a compound of formula XXXIII.

a23) Reacting a compound of formula XXXIII with a reagent such as R³CHClC(=O)Cl in the presence of a base such as sodium bicarbonate in an inert solvent such as DCM to give a compound of the formula XXXIV.

In a further aspect the present invention relates to a process of preparing a compound of the formula XXXV wherein X¹ is a halogen such as Cl, Br, F and B¹ and R⁵ are as defined under formula 1 above, comprising step a24;

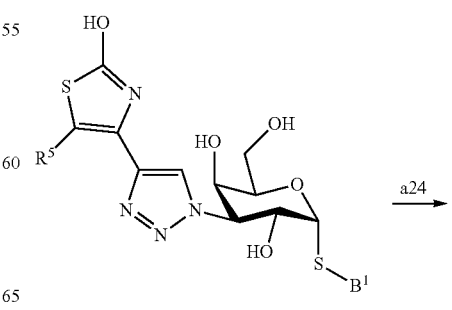

-continued

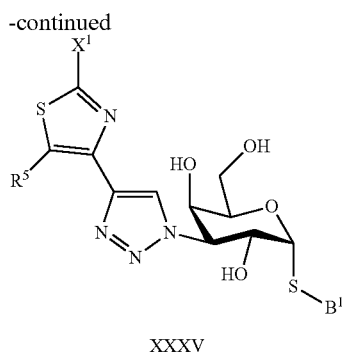

XXXV a24) Reacting a compound of formula V with a halogenating compound such as $POCl_3$, $POBr_3$, Yarovenkos reagent or DAST to give a compound of formula XXXV.

In a still further aspect the present invention relates to a process of preparing a compound of the formula XXXVII wherein $X^2$ is as a halogen such as Cl, Br, F and $B^1$ and $R^3$ are as defined under formula 1 above, comprising step a25;

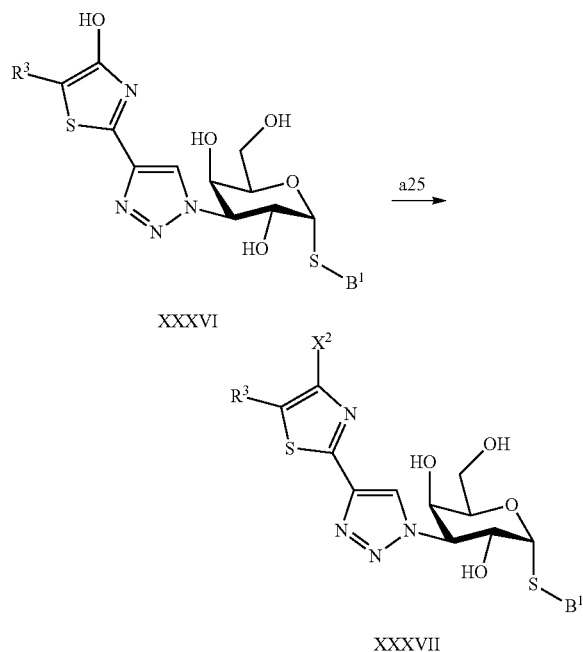

a25) Reacting a compound of formula XXXVI with a halogenating compound such as $POCl_3$, $POBr_3$, Yarovenkos reagent or DAST to give a compound of formula XXXVII.

DETAILED DESCRIPTION OF THE INVENTION

The present compounds of formula (1) differ from prior art compounds particularly in that the pyranose ring is α-D-galactopyranose. It is important to emphasize that alpha and beta anomers are very different isomers and it is by no means considered to be obvious to the skilled person to expect same or similar activity of both anomers. Consequently, alpha and beta anomers do not in general posses the same activity, and this is common knowledge to the skilled person. The compounds of the present invention are novel α-D-galactopyranose compounds that unexpectedly have shown very high affinity and specificity for galectin-1, and are considered novel potent drug candidates. Some of the novel α-D-galactopyranose compounds have both galectin-1 and galectin-3 affinity and, as such have a broader disease treatment profile compared to selective galectin-1 inhibitors.

In a broad aspect, the present invention concerns a compound of the above formula (1) wherein $R^1$ and $B^1$ are as defined. Below are described further embodiments.

In an embodiment $R^1$ is

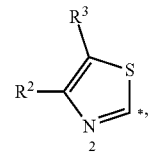

wherein the asterix * indicates the carbon atom of the heteroaromatic ring that is covalently attached to the triazole group of formula (1);

wherein $R^2$ is selected from the group consisting of OH and halogen; and $R^3$ is selected from the group consisting of hydrogen (H), $C_{1-6}$ alkyl and halogen.

In an embodiment $R^2$ is selected from the group consisting of OH, chloro, bromo and fluoro. In a preferred embodiment $R^2$ is OH. In another preferred embodiment $R^2$ is Cl. In a further preferred embodiment $R^2$ is Br. In a still further preferred embodiment $R^2$ is F.

In a further embodiment $R^3$ is selected from the group consisting of hydrogen, $C_{1-6}$ alkyl and halogen.

In another embodiment $R^2$ is OH, and $R^3$ is selected from the group consisting of hydrogen, $C_{1-6}$ alkyl and halogen. When $R^2$ is OH and $R^3$ is H then depending on conditions such as acidic or basic the OH group maybe on the oxo tautomer form.

In a further embodiment $R^2$ is halogen, and $R^3$ is selected from the group consisting of hydrogen and halogen. Typically, $R^2$ is halogen, and $R^3$ is H. In a further embodiment both $R^2$ and $R^3$ are halogen, such as Cl or F.

The above compounds wherein $R^1$ is formula 2 have high affinity to both galectin-1 and galectin-3.

In a further embodiment $R^1$ is

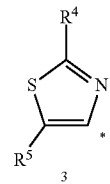

wherein the asterix * indicates the carbon atom of the heteroaromatic ring that is covalently attached to the triazole group of formula (1);

wherein $R^4$ is selected from the group consisting of OH and halogen, preferably F, Cl, and Br; and $R^5$ is selected from the group consisting of hydrogen, $C_{1-6}$ alkyl and halogen. In a preferred embodiment $R^4$ is OH.

In an embodiment $R^4$ is OH and $R^5$ is selected from the group consisting of hydrogen, $C_{1-6}$ alkyl and halogen. When $R^4$ is OH in the present compounds of formula (1) wherein $R^1$ is 3, data have shown that such compounds have galectin 1 selectivity, and in particular when $R^4$ is OH and $R^5$ is H, then such compounds are highly selective galectin-1 inhibitors.

In a further embodiment $R^4$ is halogen and $R^5$ is selected from the group consisting of hydrogen, C1-6 alkyl and halogen. Typically, $R^4$ is selected from Cl and F. In a further embodiment $R^4$ is selected from Cl and F and $R^5$ is H.

In a further embodiment $B^1$ is selected from phenyl optionally substituted with a group selected from halogen, $SC_{1-3}$ alkyl, optionally substituted with a F; $C_{1-6}$ alkyl and CN.

In a still further embodiment $B^1$ is selected from a phenyl substituted with one, two or three substituents selected from Cl, F, Br, $CF_3$, $SCF_3$, $CH_3$, and CN. Typically, the phenyl is substituted with at least 2 Cl, such as 3 Cl or 2 Cl and one F. In another embodiment the phenyl is substituted with one Cl and one F. In a further embodiment the phenyl is substituted with at least one Br, such as two Br and one F, or one Br and one CN. In a still further embodiment phenyl is substituted with one halogen, such as Cl, and one substituent selected from $CF_3$, $SCF_3$, and $CH_3$.

In a further embodiment $B^1$ is selected from phenyl optionally substituted with a group selected from halogen and —$CONR^{35}R^{36}$, wherein $R^{35}$ and $R^{36}$ are independently selected from H, $C_{1-3}$ alkyl, cyclopropyl, and iso-propyl. In one embodiment $B^1$ is selected from phenyl substituted with a group selected from halogen, such as 1, 2 or 3 halogens, for instance Cl and F, such as 2 Cl and one F or 1 Cl and 2 F. In another embodiment $B^1$ is selected from phenyl substituted with a group selected from halogen, such as Cl, and —$CONR^{35}R^{36}$, wherein $R^{35}$ and $R^{36}$ are independently selected from H and $C_{1-3}$ alkyl, such as methyl. Thus, in one example B1 is selected from phenyl substituted with one halogen, such as Cl, and one —$CONR^{35}R^{36}$, wherein $R^{35}$ and $R^{36}$ are both methyl.

In a further embodiment $B^1$ is selected from a pyridinyl, optionally substituted with a group selected from a halogen; —COOH; —$CONR^{35}R^{36}$, wherein $R^{35}$ and $R^{36}$ are independently selected from H, $C_{1-3}$ alkyl, cyclopropyl, and iso-propyl; isopropyl, optionally substituted with a F; CN; and a methyl optionally substituted with a F.

In a still further embodiment $B^1$ is selected from a pyridinyl substituted with two substituents selected from Cl, Br, COOH, $CONH_2$, isopropyl, CN and $CF_3$. Typically, in individual embodiments the substituents are Br and $CF_3$, or Br and CN, or Cl and CN, or Cl and $CF_3$. In other individual embodiments the substituents are Cl and $CONH_2$, Cl and COOH, Br and isopropyl.

In a further embodiment $B^1$ is selected from a pyridinyl substituted with a group selected from halogen, such as Cl, and —$CONR^{35}R^{36}$, wherein $R^{35}$ and $R^{36}$ are independently selected from H and $C_{1-3}$ alkyl, such as methyl. Thus, in one example $B^1$ is selected from pyridinyl substituted with one halogen, such as Cl, and one —$CONR^{35}R^{36}$, wherein $R^{35}$ and $R^{36}$ are both methyl.

In a further embodiment the compound of formula (1) is selected from any one of:

5-Bromo-6-trifluoromethyl-pyridine-3-yl 3-[4-(4-chlorothiazol-2-yl)-1H-1,2,3-triazol-1-yl]-3-deoxy-1-thio-α-D-galactopyranoside, 5-Bromo-6-trifluoromethyl-pyridine-3-yl 3-[4-(4-bromothiazol-2-yl)-1H-1,2,3-triazol-1-yl]-3-deoxy-1-thio-α-D-galactopyranoside, 5-Chloro-6-cyano-pyridine-3-yl 3-[4-(4-chlorothiazol-2-yl)-1H-1,2,3-triazol-1-yl]-3-deoxy-1-thio-α-D-galactopyranoside, 5-Bromo-2-cyano-pyridine-3-yl 3-[4-(4-chlorothiazol-2-yl)-1H-1,2,3-triazol-1-yl]-3-deoxy-1-thio-α-D-galactopyranoside, 5-Chloro-2-cyano-pyridine-3-yl 3-[4-(4-chlorothiazol-2-yl)-1H-1,2,3-triazol-1-yl]-3-deoxy-1-thio-α-D-galactopyranoside, 5-Bromo-6-cyano-3-pyridyl 3-[4-(4-chlorothiazol-2-yl)-1H-1,2,3-triazol-1-yl]-3-deoxy-1-thio-α-D-galactopyranoside, 3,4-Dichlorophenyl 3-[4-(2-chlorothiazol-4-yl)-1H-1,2,3-triazol-1-yl]-3-deoxy-1-thio-α-D-galactopyranoside, 3,4-Dichlorophenyl 3-deoxy-3-[4-(2-fluorothiazol-4-yl)-1H-1,2,3-triazol-1-yl]-1-thio-α-D-galactopyranoside, 3,4-Dichlorophenyl 3-deoxy-3-[4-(4-fluorothiazol-2-yl)-1H-1,2,3-triazol-1-yl]-1-thio-α-D-galactopyranoside, 3,4-Dichlorophenyl 3-deoxy-3-[4-(4,5-difluorothiazol-2-yl)-1H-1,2,3-triazol-1-yl]-1-thio-α-D-galactopyranoside, 3,4-Dichlorophenyl 3-deoxy-3-[4-(4-hydroxythiazol-2-yl)-1H-1,2,3-triazol-1-yl]-1-thio-α-D-galactopyranoside, 3,4-Dichlorophenyl 3-deoxy-3-[4-(2-hydroxythiazol-4-yl)-1H-1,2,3-triazol-1-yl]-1-thio-α-D-galactopyranoside, 5-Chloro-6-cyano-pyridine-3-yl 3-deoxy-3-[4-(2-hydroxythiazol-4-yl)-1H-1,2,3-triazol-1-yl]-1-thio-α-D-galactopyranoside, 5-Bromo-2-cyano-pyridine-3-yl 3-deoxy-3-[4-(2-hydroxythiazol-4-yl)-1H-1,2,3-triazol-1-yl]-1-thio-α-D-galactopyranoside, 5-Bromo-6-cyano-3-pyridyl 3-deoxy-3-[4-(2-hydroxythiazol-4-yl)-1H-1,2,3-triazol-1-yl]-1-thio-α-D-galactopyranoside, 5-Chloro-2-cyano-3-pyridyl 3-deoxy-3-[4-(2-hydroxythiazol-4-yl)-1H-1,2,3-triazol-1-yl]-1-thio-α-D-galactopyranoside, 5-Chloro-6-trifluoromethyl-pyridin-3-yl 3-deoxy-3-[4-(2-hydroxythiazol-4-yl)-1H-1,2,3-triazol-1-yl]-1-thio-α-D-galactopyranoside, 3,5-dichloro-4-fluoro-phenyl 3-deoxy-3-[4-(2-hydroxythiazol-4-yl)-1H-1,2,3-triazol-1-yl]-1-thio-α-D-galactopyranoside, 3-Chloro-4-fluoro-phenyl 3-deoxy-3-[4-(2-hydroxythiazol-4-yl)-1H-1,2,3-triazol-1-yl]-1-thio-α-D-galactopyranoside, 3,4,5-trichlorophenyl 3-deoxy-3-[4-(2-hydroxythiazol-4-yl)-1H-1,2,3-triazol-1-yl]-1-thio-α-D-galactopyranoside, 3,5-dibromo-4-fluorophenyl 3-deoxy-3-[4-(2-hydroxythiazol-4-yl)-1H-1,2,3-triazol-1-yl]-1-thio-α-D-galactopyranoside, 3-Bromo-4-cyanophenyl 3-deoxy-3-[4-(2-hydroxythiazol-4-yl)-1H-1,2,3-triazol-1-yl]-1-thio-α-D-galactopyranoside, 5-Bromo-6-trifluoromethyl-3-pyridyl 3-deoxy-3-[4-(2-hydroxythiazol-4-yl)-1H-1,2,3-triazol-1-yl]-1-thio-α-D-galactopyranoside, 3-Chloro-4-trifluoromethylphenyl 3-deoxy-3-[4-(2-hydroxythiazol-4-yl)-1H-1,2,3-triazol-1-yl]-1-thio-α-D-galactopyranoside, 3-Chloro-4-trifluoromethylthiophenyl 3-deoxy-3-[4-(2-hydroxythiazol-4-yl)-1H-1,2,3-triazol-1-yl]-1-thio-α-D-galactopyranoside, 3-Chloro-4-methylphenyl 3-deoxy-3-[4-(2-hydroxythiazol-4-yl)-1H-1,2,3-triazol-1-yl]-1-thio-α-D-galactopyranoside, 5-Chloro-picolinamide-3-yl 3-[4-(4-chlorothiazol-2-yl)-1H-1,2,3-triazol-1-yl]-3-deoxy-1-thio-α-D-galactopyranoside, 2-Carboxy-5-chloropyridyl 3-deoxy-3-[4-(2-hydroxythiazol-4-yl)-1H-1,2,3-triazol-1-yl]-1-thio-α-D-galactopyranoside, 5-Bromo-6-trifluoromethyl-pyridine-3-yl 3-deoxy-3-[4-(4,5-dichlorothiazol-2-yl)-1H-1,2,3-triazol-1-yl]-1-thio-α-D-galactopyranoside, 5-Bromo-2-isopropyl-pyridine-3-yl 3-[4-(4-chlorothiazol-2-yl)-1H-1,2,3-triazol-1-yl]-3-deoxy-1-thio-α-D-galactopyranoside.

In a still further embodiment the compound of formula (1) is selected from any one of:

3,4-Dichloro-6-fluoro-phenyl 3-deoxy-3-[4-(2-hydroxythiazol-4-yl)-1H-1,2,3-triazol-1-yl]-1-thio-α-D-galactopyranoside, 4-Chloro-N,N'-dimethylbenzamide-2-yl 3-deoxy-3-[4-(2-hydroxythiazol-4-yl)-1H-1,2,3-triazol-1-yl]-1-thio-α-D-galactopyranoside, 5-Chloro-N,N'-dimethyl-picolinamide-3-yl 3-deoxy-3-[4-(2-hydroxythiazol-4-yl)-1H-1,2,3-triazol-1-yl]-1-thio-α-D-galactopyranoside.

The skilled person will understand that it may be necessary to adjust or change the order of steps in the processes a1 to a23, and such change of order is encompassed by the aspects of the process as described above in the reaction schemes and accompanying description of the process steps.

Furthermore, the skilled person will understand that the processes described above and hereinafter the functional groups of intermediate compounds may need to be protected by protecting groups.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g. t-butyldimethylsilyl, t-butyldipheylsilyl or trimethylsilyl), AcO(acetoxy), TBS(t-butyldimethylsilyl), TMS(trimethylsilyl), PMB (p-methoxybenzyl), and tetrahydropyranyl. Suitable protecting groups for carboxylic acid include $(C_{1-6})$-alkyl or benzyl esters. Suitable protecting groups for amino include t-butyloxycarbonyl, benzyloxycarbonyl, 2-(trimethylsilyl)-ethoxy-methyl or 2-trimethylsilylethoxycarbonyl (Teoc). Suitable protecting groups for S include S—C(=N)NH$_2$, TIPS.

The protection and deprotection of functional groups may take place before or after any reaction in the above-mentioned processes.

Furthermore the skilled person will appreciate, that, in order to obtain compounds of the invention in an alternative, and on some occasions more convenient manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

In a still further embodiment the compound (1) is on free form. "On free form" as used herein means a compound of formula (1), either an acid form or base form, or as a neutral compound, depending on the substitutents. The free form does not have any acid salt or base salt in addition. In one embodiment the free form is an anhydrate. In another embodiment the free form is a solvate, such as a hydrate.

In a further embodiment the compound of formula (1) is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

The term "$C_{1-x}$ alkyl" as used herein means an alkyl group containing 1-x carbon atoms, e.g. $C_{1-5}$ or $C_{1-6}$, such as methyl, ethyl, propyl, butyl, pentyl or hexyl.

The term "branched $C_{3-6}$ alkyl" as used herein means a branched alkyl group containing 3-6 carbon atoms, such as isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl.

The term "$C_{3-7}$ cycloalkyl" as used herein means a cyclic alkyl group containing 3-7 carbon atoms, such as cyclopropyl, cyclobutyl, cyclopentyl, cyclohexyl, cycloheptyl, and 1-methylcyclopropyl.

The term "$C_{5-7}$ cycloalkyl" as used herein means a cyclic alkyl group containing 5-7 carbon atoms, such as cyclopentyl, cyclohexyl, or cycloheptyl.

The term "Oxo" as used herein means an oxygen atom with double bonds, also indicated as =O.

The term "CN" as used herein means a nitril.

The term "a five or six membered heteroaromatic ring" as used herein means one five membered heteroaromatic ring or one six membered heteroaromatic ring. The five membered heteroaromatic ring contains 5 ring atoms of which one to four are heteroatoms selected from N, O, and S. The six membered heteroaromatic ring contains 6 ring atoms of which one to five are heteroatoms selected from N, O and S. Examples include thiophene, furan, pyran, pyrrole, imidazole, pyrazole, isothiazole, isooxazole, pyridine, pyrazine, pyrimidine and pyridazine. When such heteroaromatic rings are substituents they are termed thiophenyl, furanyl, pyranyl, pyrrolyl, imidazolyl, pyrazolyl, isothiazolyl, isooxazolyl, pyridinyl, pyrazinyl, pyrimidinyl and pyridazinyl. Also included are oxazoyl, thiazoyl, thiadiazoly, oxadiazoyl, and pyridonyl.

The term "a heterocycle, such as heteroaryl or heterocycloalkyl" as used herein means a heterocycle consisting of one or more 3-7 membered ring systems containing one or more heteroatoms and wherein such ring systems may optionally be aromatic. The term "a heteroaryl" as used herein means a mono or bicyclic aromatic ringsystem containing one or more heteroatoms, such as 1-10, e.g. 1-6, selected from O, S, and N, including but not limited to oxazolyl, oxadiazolyl, thiophenyl, thiadiazolyl, thiazolyl, pyridyl, pyrimidinyl, pyridonyl, pyrimidonyl, quinolinyl, azaquionolyl, isoquinolinyl, azaisoquinolyl, quinazolinyl, azaquinazolinyl, bensozazoyl, azabensoxazoyl, bensothiazoyl, or azabensothiazoyl. The term "a heterocycloalkyl" as used herein means a mono or bicyclic 3-7 membered alifatic heterocycle containing one or more heteroatoms, such as 1-7, e.g. 1-5, selected from O, S, and N, including but not limited to piperidinyl, tetrahydropyranyl, tetrahydrothipyranyl, or piperidonyl.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular, a human being, but it may also include animals, such as dogs, cats, cows, sheep and pigs.

The term "a therapeutically effective amount" of a compound of formula (1) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (1) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person skilled within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99% by weight of said at least one pharmaceutically acceptable adjuvant, diluent, excipient and/or carrier and from 1 to 99% by weight of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compounds as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context). This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention indiverse forms thereof.

Experimental Procedures (Evaluation of Kd Values)

The affinity of Example 1-33 for galectins were determined by a fluorescence anisotropy assay where the compound was used as an inhibitor of the interaction between galectin and a fluorescein tagged saccharide probe as described Sörme, P., Kahl-Knutsson, B., Huflejt, M., Nilsson, U. J., and Leffler H. (2004) Fluorescence polarization as an analytical tool to evaluate galectin-ligand interactions. Anal. Biochem. 334: 36-47, (Sörme et al., 2004) and Monovalent interactions of Galectin-1 By Salomonsson, Emma; Larumbe, Amaia; Tejler, Johan; Tullberg, Erik; Rydberg, Hanna; Sundin, Anders; Khabut, Areej; Frejd, Torbjorn; Lobsanov, Yuri D.; Rini, James M.; et al, From Biochemistry (2010), 49(44), 9518-9532, (Salomonsson et al., 2010).

| Example | Name | Structure | Galectin-1 Kd (μM) | Galectin-3 Kd (μM) |
|---|---|---|---|---|
| 1 | 5-Bromo-6-trifluoromethyl-pyridine-3-yl 3-[4-(4-chlorothiazol-2-yl)-1H-1,2,3-triazol-1-yl]-3-deoxy-1-thio-α-D-galactopyranoside | 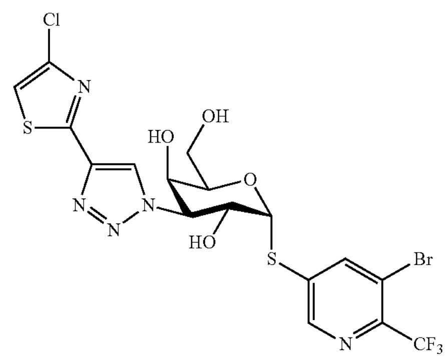 | 0.11 | 0.25 |
| 2 | 5-Bromo-6-trifluoromethyl-pyridine-3-yl 3-[4-(4-bromothiazol-2-yl)-1H-1,2,3-triazol-1-yl]-3-deoxy-1-thio-α-D-galactopyranoside | 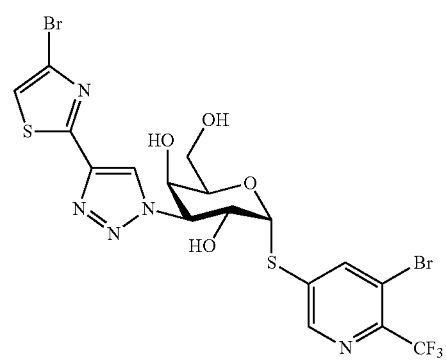 | 0.16 | 0.58 |
| 3 | 5-Chloro-6-cyano-pyridine-3-yl 3-[4-(4-chlorothiazol-2-yl)-1H-1,2,3-triazol-1-yl]-3-deoxy-1-thio-α-D-galactopyranoside | 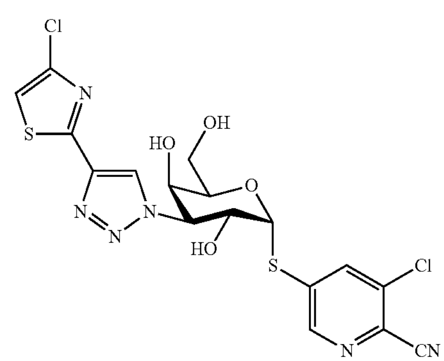 | 0.095 | 0.42 |

-continued

| Example | Name | Structure | Galectin-1 Kd (μM) | Galectin-3 Kd (μM) |
|---|---|---|---|---|
| 4 | 5-Bromo-2-cyano-pyridine-3-yl 3-[4-(4-chlorothiazol-2-yl)-1H-1,2,3-triazol-1-yl]-3-deoxy-1-thio-α-D-galactopyranoside | 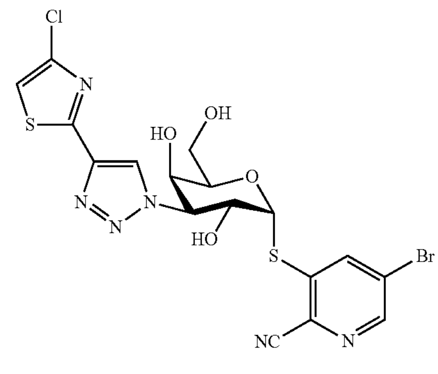 | 0.085 | 0.2 |
| 5 | 5-Chloro-2-cyano-pyridine-3-yl 3-[4-(4-chlorothiazol-2-yl)-1H-1,2,3-triazol-1-yl]-3-deoxy-1-thio-α-D-galactopyranoside | 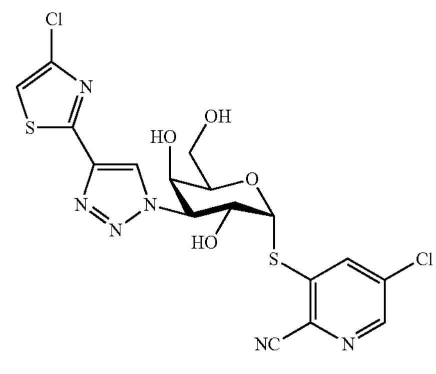 | 0.095 | 0.22 |
| 6 | 5-Bromo-6-cyano-3-pyridyl 3-[4-(4-chlorothiazol-2-yl)-1H-1,2,3-triazol-1-yl]-3-deoxy-1-thio-α-D-galactopyranoside | 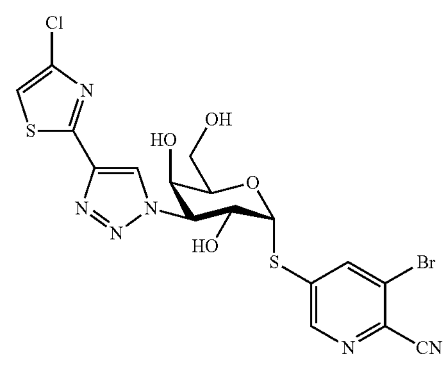 | 0.068 | 0.25 |
| 7 | 3,4-Dichlorophenyl 3-[4-(2-chlorothiazol-4-yl)-1H-1,2,3-triazol-1-yl]-3-deoxy-1-thio-α-D-galactopyranoside | 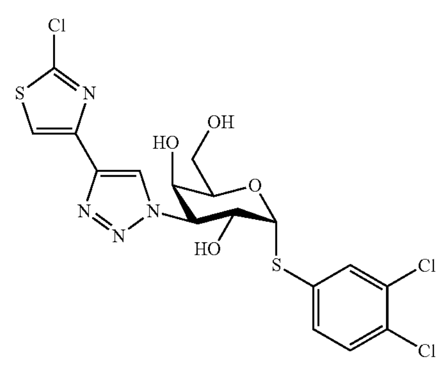 | 0.49 | 1.4 |

| Example | Name | Structure | Galectin-1 Kd (μM) | Galectin-3 Kd (μM) |
|---|---|---|---|---|
| 8 | 3,4-Dichlorophenyl 3-deoxy-3-[4-(2-fluorothiazol-4-yl)-1H-1,2,3-triazol-1-yl]-1-thio-α-D-galactopyranoside | 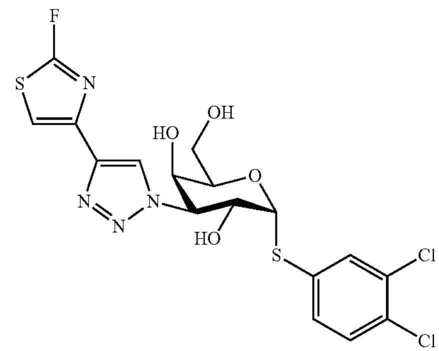 | | |
| 9 | 3,4-Dichlorophenyl 3-deoxy-3-[4-(4-fluorothiazol-2-yl)-1H-1,2,3-triazol-1-yl]-1-thio-α-D-galactopyranoside | 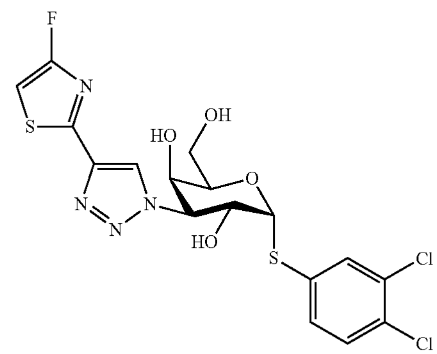 | | |
| 10 | 3,4-Dichlorophenyl 3-deoxy-3-[4-(4,5-difluorothiazol-2-yl)-1H-1,2,3-triazol-1-yl]-1-thio-α-D-galactopyranoside | 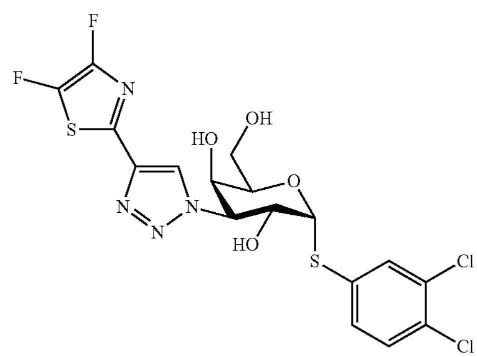 | | |
| 11 | 3,4-Dichlorophenyl 3-deoxy-3-[4-(4-hydroxythiazol-2-yl)-1H-1,2,3-triazol-1-yl]-1-thio-α-D-galactopyranoside | 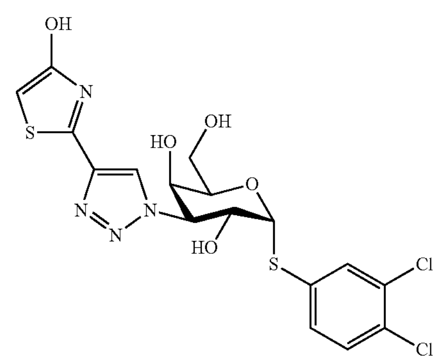 | 0.65 | 1.7 |

-continued

| Example | Name | Structure | Galectin-1 Kd (μM) | Galectin-3 Kd (μM) |
|---|---|---|---|---|
| 12 | 3,4-Dichlorophenyl 3-deoxy-3-[4-(2-hydroxythiazol-4-yl)-1H-1,2,3-triazol-1-yl]-1-thio-α-D-galactopyranoside | 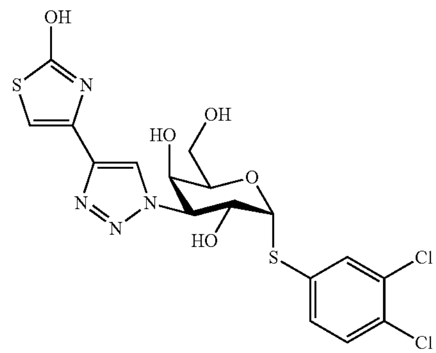 | 0.058 | 8.6 |
| 13 | 5-Chloro-6-cyano-pyridine-3-yl 3-deoxy-3-[4-(2-hydroxythiazol-4-yl)-1H-1,2,3-triazol-1-yl]-1-thio-α-D-galactopyranoside | 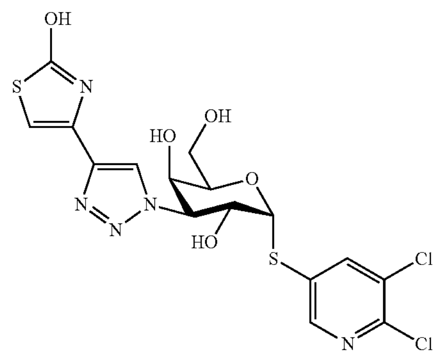 | 0.038 | 8 |
| 14 | 5-Bromo-2-cyano-pyridine-3-yl 3-deoxy-3-[4-(2-hydroxythiazol-4-yl)-1H-1,2,3-triazol-1-yl]-1-thio-α-D-galactopyranoside | 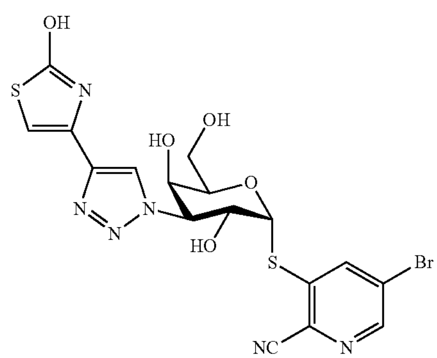 | 0.033 | 2.6 |
| 15 | 5-Bromo-6-cyano-3-pyridyl 3-deoxy-3-[4-(2-hydroxythiazol-4-yl)-1H-1,2,3-triazol-1-yl]-1-thio-α-D-galactopyranoside | 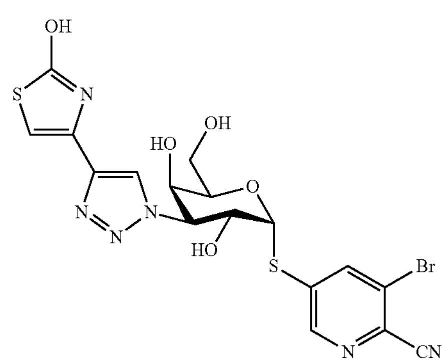 | 0.019 | 2.8 |

-continued

| Example | Name | Structure | Galectin-1 Kd (μM) | Galectin-3 Kd (μM) |
|---|---|---|---|---|
| 16 | 5-Chloro-2-cyano-3-pyridyl 3-deoxy-3-[4-(2-hydroxythiazol-4-yl)-1H-1,2,3-triazol-1-yl]-1-thio-α-D-galactopyranoside | 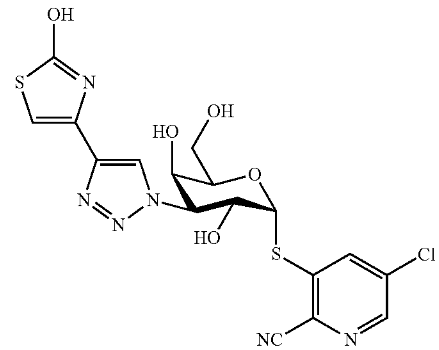 | 0.006 | 2.2 |
| 17 | 5-Chloro-6-trifluoromethyl-pyridin-3-yl 3-deoxy-3-[4-(2-hydroxythiazol-4-yl)-1H-1,2,3-triazol-1-yl]-1-thio-α-D-galactopyranoside | 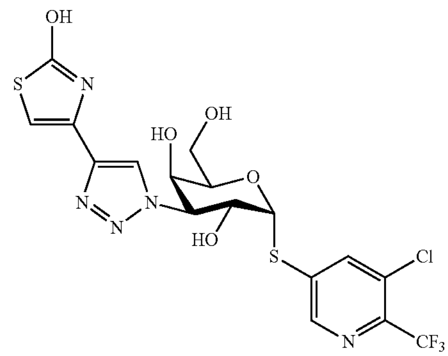 | 0.028 | 2.8 |
| 18 | 3,5-dichloro-4-fluoro-phenyl 3-deoxy-3-[4-(2-hydroxythiazol-4-yl)-1H-1,2,3-triazol-1-yl]-1-thio-α-D-galactopyranoside | 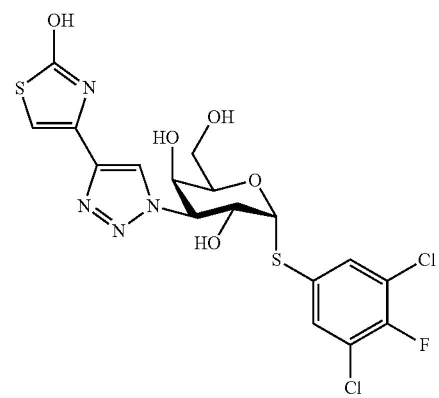 | 0.027 | 9.7 |
| 19 | 3-Chloro-4-fluoro-phenyl 3-deoxy-3-[4-(2-hydroxythiazol-4-yl)-1H-1,2,3-triazol-1-yl]-1-thio-α-D-galactopyranoside | 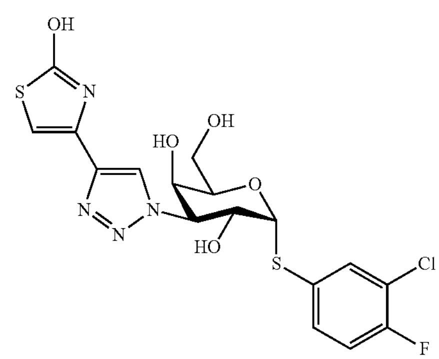 | | |

-continued

| Example | Name | Structure | Galectin-1 Kd (μM) | Galectin-3 Kd (μM) |
|---|---|---|---|---|
| 20 | 3,4,5-trichlorophenyl 3-deoxy-3-[4-(2-hydroxythiazol-4-yl)-1H-1,2,3-triazol-1-yl]-1-thio-α-D-galactopyranoside | 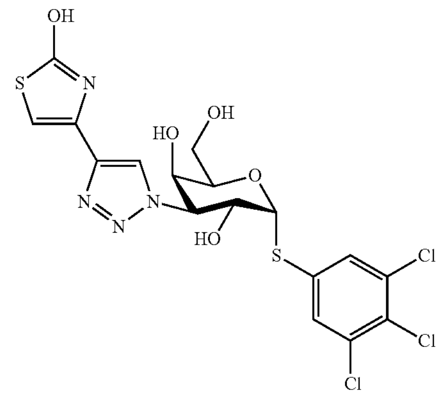 | 0.056 | 6 |
| 21 | 3,5-dibromo-4-fluorophenyl 3-deoxy-3-[4-(2-hydroxythiazol-4-yl)-1H-1,2,3-triazol-1-yl]-1-thio-α-D-galactopyranoside | 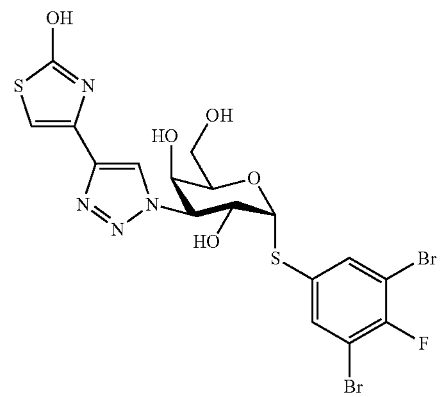 | 0.050 | 4.6 |
| 22 | 3-Bromo-4-cyanophenyl 3-deoxy-3-[4-(2-hydroxythiazol-4-yl)-1H-1,2,3-triazol-1-yl]-1-thio-α-D-galactopyranoside | 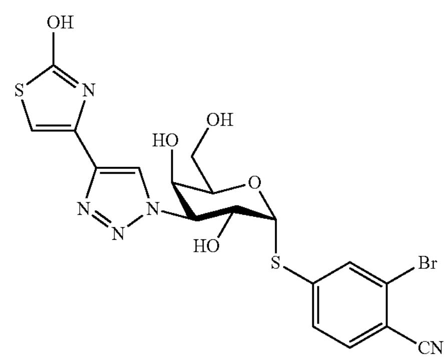 | 0.063 | 6 |
| 23 | 5-Bromo-6-trifluoromethyl-3-pyridyl 3-deoxy-3-[4-(2-hydroxythiazol-4-yl)-1H-1,2,3-triazol-1-yl]-1-thio-α-D-galactopyranoside | 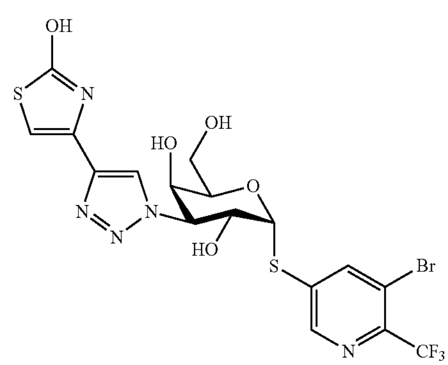 | 0.032 | 3.1 |

-continued

| Example | Name | Structure | Galectin-1 Kd (µM) | Galectin-3 Kd (µM) |
|---|---|---|---|---|
| 24 | 3-Chloro-4-trifluoromethylphenyl 3-deoxy-3-[4-(2-hydroxythiazol-4-yl)-1H-1,2,3-triazol-1-yl]-1-thio-α-D-galactopyranoside | 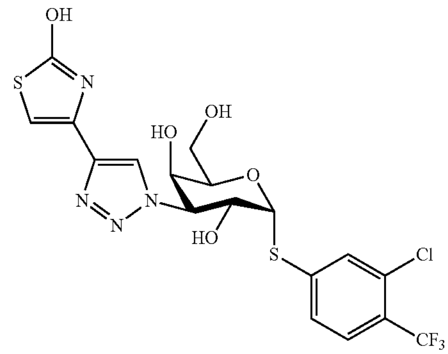 | 0.071 | 6.5 |
| 25 | 3-Chloro-4-trifluoromethylthiophenyl 3-deoxy-3-[4-(2-hydroxythiazol-4-yl)-1H-1,2,3-triazol-1-yl]-1-thio-α-D-galactopyranoside | 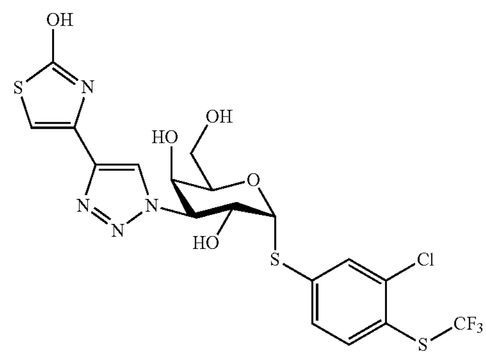 | | |
| 26 | 3-Chloro-4-methylphenyl 3-deoxy-3-[4-(2-hydroxythiazol-4-yl)-1H-1,2,3-triazol-1-yl]-1-thio-α-D-galactopyranoside | 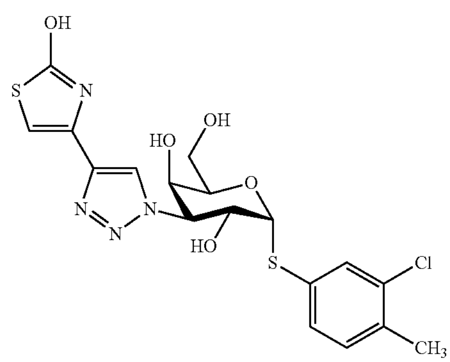 | 0.082 | 6.6 |
| 27 | 5-Chloro-picolinamide-3-yl 3-[4-(4-chlorothiazol-2-yl)-1H-1,2,3-triazol-1-yl]-3-deoxy-1-thio-α-D-galactopyranoside | 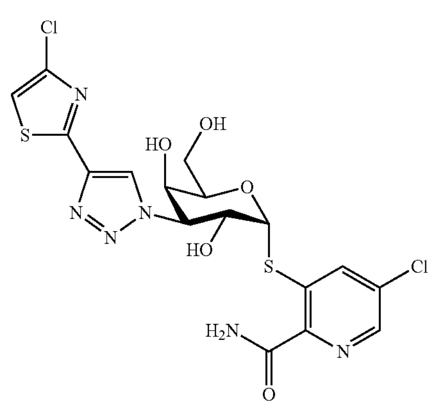 | | |

-continued

| Example | Name | Structure | Galectin-1 Kd (μM) | Galectin-3 Kd (μM) |
|---|---|---|---|---|
| 28 | 2-Carboxy-5-chloropyridyl 3-deoxy-3-[4-(2-hydroxythiazol-4-yl)-1H-1,2,3-triazol-1-yl]-1-thio-α-D-galactopyranoside | 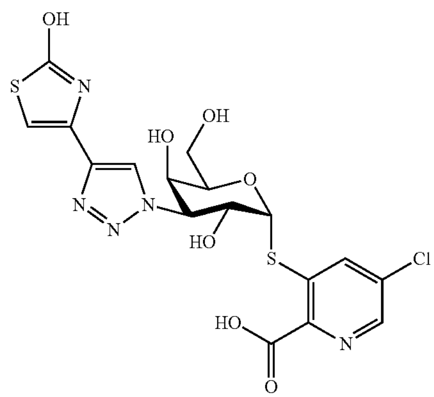 | 0.046 | 5.7 |
| 29 | 5-Bromo-6-trifluoromethyl-pyridine-3-yl 3-deoxy-3-[4-(4,5-dichlorothiazol-2-yl)-1H-1,2,3-triazol-1-yl]-1-thio-α-D-galactopyranoside | 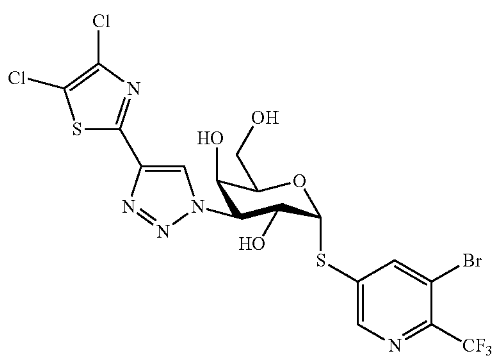 | 0.39 | 0.069 |
| 30 | 5-Bromo-2-isopropyl-pyridine-3-yl 3-[4-(4-chlorothiazol-2-yl)-1H-1,2,3-triazol-1-yl]-3-deoxy-1-thio-α-D-galactopyranoside | 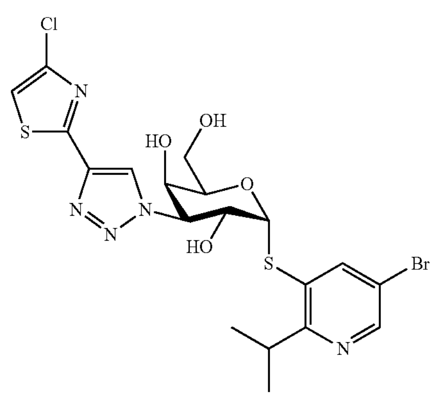 | | |
| 31 | 3,4-Dichloro-6-fluoro-phenyl 3-deoxy-3-[4-(2-hydroxythiazol-4-yl)-1H-1,2,3-triazol-1-yl]-1-thio-α-D-galactopyranoside | 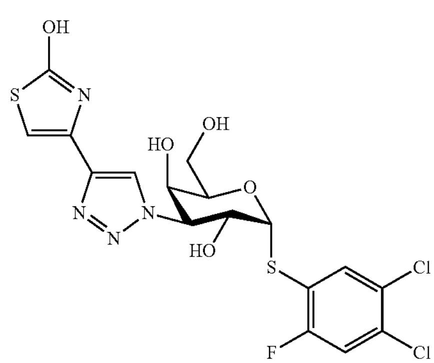 | 0.013 | 4.6 |

| Example | Name | Structure | Galectin-1 Kd (μM) | Galectin-3 Kd (μM) |
|---|---|---|---|---|
| 32 | 4-Chloro-N,N'-dimethylbenzamide-2-yl 3-deoxy-3-[4-(2-hydroxythiazol-4-yl)-1H-1,2,3-triazol-1-yl]-1-thio-α-D-galactopyranoside | 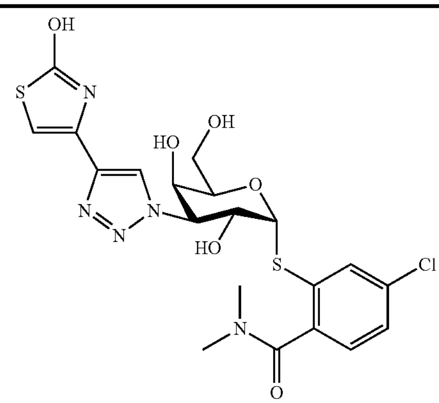 | 0.044 | 2.1 |
| 33 | 5-Chloro-N,N'-dimethyl-picolinamide-3-yl 3-deoxy-3-[4-(2-hydroxythiazol-4-yl)-1H-1,2,3-triazol-1-yl]-1-thio-α-D-galactopyranoside | 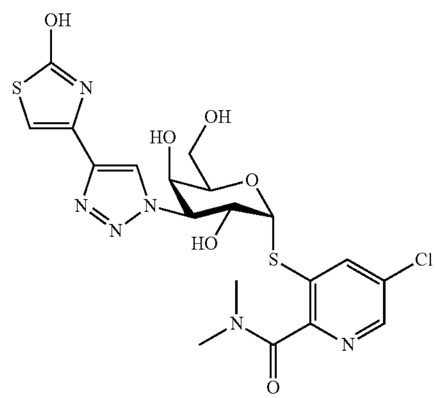 | 0.054 | 1.7 |

Synthesis of Examples and Intermediates

General Procedures

Nuclear Magnetic Resonance (NMR) spectra were recorded on a400 MHz Bruker AVANCE III 500 instrument or a Varian instrument at 400 MHz, at 25° C. Chemical shifts are reported in ppm (d) using the residual solvent as internal standard. Peak multiplicities are expressed as follow: s, singlet; d, doublet; dd, doublet of doublets; t, triplet; dt, doublet of triplet; q, quartet; m, multiplet; br s, broad singlet. LC-MS were acquired on anAgilent 1200 HPLC coupled with an Agilent MSD mass spectrometer operating in ES(+) ionization mode. Column: XBridge C18 (4.6×50 mm, 3.5 μm) or SunFire C18 (4.6×50 mm, 3.5 μm). Solvent A water+0.1% TFA and solvent B Acetonitrile+0.1% TFA or solvent A water (10 mM Ammonium hydrogen carbonate) and solvent B Acetonitrile. Wavelength: 254 nM. Alternatively LC-MS were acquired on an Agilent 1100 HPLC coupled with an Agilent MSD mass spectrometer operating in ES (+) ionization mode. Column: Waters symmetry 2.1×30 mm C18 or Chromolith RP-18 2×50 mm. Solvent A water+0.1% TFA and solvent B Acetonitrile+0.1% TFA. Wavelength 254 nm.

Preparative HPLC was performed on a Gilson 215. Flow: 25 mL/min Column: XBridge prep C18 10 μm OBD (19× 250 mm) column. Wavelength: 254 nM. Solvent A water (10 mM Ammonium hydrogen carbonate) and solvent B Acetonitrile.

Alternatively preparative HPLC were acquired on a Gilson system. Flow: 15 10124EP00 52 ml/min Column: kromasil 100-5-C18 column. Wavelength: 220 nm. Solvent A water+0.1% TFA and solvent B Acetonitrile+0.1% TFA.

The following abbreviations are used
aq: aqueous
Calcd: Calculated
$CH_3CN$: Acetonitrile
CuI: Copper Iodide
DCM: Dichloromethane
DIPEA: Diisopropylethylamine
DMF: N,N-dimethylformamide
ESI-MS: Electrospray ionization mass spectrometry
EtOAc or EA: Ethylacetate
GC: Gas chromatography
h: hour(s)
HPLC: High performance liquid chromatography
LC: Liquid Chromatography
MeCN: Acetonitrile
mL: milliliter
MeOH: Methanol
MeOD: Deuterated methanol
mm: millimeter
mM: millimolar
MS: Mass spectroscopy
nm: nanometer
NaI: Sodium Iodide
NaOMe: Sodium methoxide
NMP: N-Methyl-2-pyrrolidone
$N_2$: Nitrogen gas
NMR: Nuclear magnetic resonance PE: petroleum ether
pH: acidity
PMB: p-methoxybenzyl
Prep: Preparative
rt: Room temperature
TEA: Triethylamine
TFA: trifluoroacetic acid
THF: Tetrahydrofuran
TMS: Trimethylsilyl
UV: Ultraviolet
Å: Ångström Example 1

5-Bromo-6-trifluoromethyl-pyridine-3-yl 3-[4-(4-chlorothiazol-2-yl)-1H-1,2,3-triazol-1-yl]-3-deoxy-1-thio-α-D-galactopyranoside

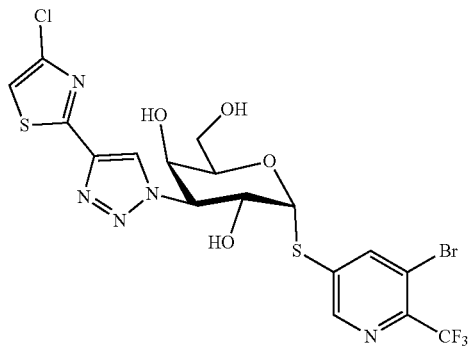

A solution of 5-bromo-6-trifluoromethyl-pyridine-3-yl 2,4,6-tri-O-acetyl-3-[4-(4-chlorothiazol-2-yl)-1H-1,2,3-triazol-1-yl]-3-deoxy-1-thio-α-D-galactopyranoside (50.0 mg, 0.0699 mmol) in MeOH/TEA/$H_2O$ (1/0.6/0.2) (1.8 mL) was stirred at room temperature for 4 h. The reaction mixture was evaporated to dryness and the crude product was purified by Prep-HPLC to afford the title compound (24.0 mg, 58%) as a white solid. $^1$H-NMR (400 MHz, MeOD) δ 8.74 (d, J=2 Hz 1H), 8.60 (s, 1H), 8.50 (d, J=1.2 Hz, 1H), 7.46 (m, 1H), 6.11 (d, J=5.2 Hz, 1H), 5.10-5.07 (m, 1H), 4.98-4.93 (m, 1H), 4.40-4.39 (t, J=5.6 Hz, 1H), 4.20 (d, J=2.8 Hz, 1H), 3.70-3.68 (m, 2H).

m/z calcd for $[C_7H_{14}BrCF_3N_5O_4S_2]^+$ [M+H]$^+$: 588.0; found: 588.0.

Example 2

5-Bromo-6-trifluoromethyl-pyridine-3-yl 3-[4-(4-bromothiazol-2-yl)-1H-1,2,3-triazol-1-yl]-3-deoxy-1-thio-α-D-galactopyranoside

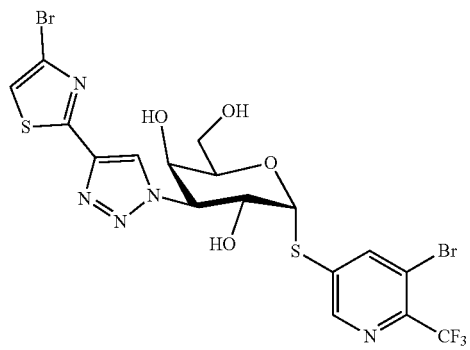

5-Bromo-6-trifluoromethyl-pyridine-3-yl 2,4,6-tri-O-acetyl-3-[4-(4-bromothiazol-2-yl)-1H-1,2,3-triazol-1-yl]-3-deoxy-1-thio-α-D-galactopyranoside (22.0 mg, 0.0290 mmol) was dissolved in MeOH (15 mL) followed by addition of TEA (14.6 mg, 0.145 mmol). The mixture was stirred at rt for 6 hours. The mixture was acidified to pH=6 by addition of 2 M HCl. The mixture was purified by reverse-phase chromatography to obtain the title compound (3.80 mg 20.7%) as white solid. $^1$H NMR (400 MHz, MeOD) δ 8.74 (d, J=2 Hz 1H), 8.61 (s, 1H), 8.50 (d, J=1.6 Hz, 1H), 7.58 (m, 1H), 6.12-6.11 (d, J=5.6 Hz, 1H), 5.07 (m, 1H), 4.98-4.96 (d, J=5.6 Hz, 1H), 4.40 (t, J=3.4 Hz, 1H), 4.20 (d, J=2.4 Hz, 1H), 3.70-3.69 (m, 2H). m/z calcd for $[C_{17}H_{14}Br_2F_3N_5O_4S_2]^+$ [M+H]$^+$: 632.0; found: 632.0.

Example 3

5-Chloro-6-cyano-pyridine-3-yl 3-[4-(4-chlorothiazol-2-yl)-1H-1,2,3-triazol-1-yl]-3-deoxy-1-thio-α-D-galactopyranoside

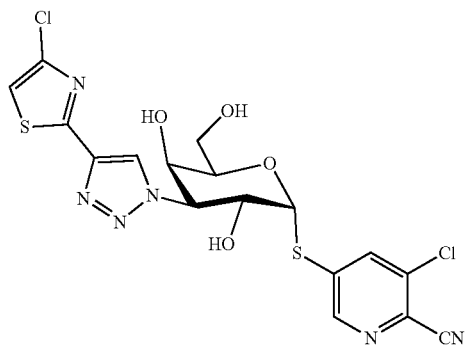

A solution of 5-chloro-6-cyano-pyridine-3-yl 2,4,6-tri-O-acetyl-3-[4-(4-chlorothiazol-4-yl)-1H-1,2,3-triazol-1-yl]-3-deoxy-1-thio-α-D-galactopyranoside (110 mg, 0.175 mmol) in MeOH/TEA/$H_2O$ (0.5/0.3/0.1)(5 mL) was stirred at room temperature for 4 h. The mixture was evaporated to dryness and the crude product was purified by Prep-HPLC to afford the title compound 50.0 mg (56.9% yield). $^1$H NMR (400 MHz, MeOD) δ 8.72 (d, J=1.9 Hz, 1H), 8.60 (s, 1H), 8.33 (d, J=1.9 Hz, 1H), 7.46 (s, 1H), 6.20 (d, J=5.3 Hz, 1H), 5.09 (dd, J=11.4, 2.8 Hz, 1H), 4.97 (dd, J=11.3, 5.4 Hz, 1H), 4.34 (t, J=6.1 Hz, 1H), 4.19 (d, J=2.8 Hz, 1H), 3.69 (d, J=6.0 Hz, 2H).

m/z calcd for $[C_{17}H_{14}Cl_2N_6O_4S_2]^+$ [M+H]$^+$: 501.4 found: 502.

Example 4

5-Bromo-2-cyano-pyridine-3-yl 3-[4-(4-chlorothiazol-2-yl)-1H-1,2,3-triazol-1-yl]-3-deoxy-1-thio-α-D-galactopyranoside

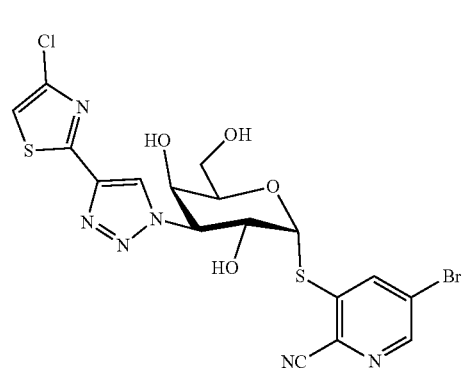

A solution of 5-bromo-2-cyano-pyridine-3-yl 2,4,6-tri-O-acetyl-3-[4-(4-chlorothiazol-2-yl)-1H-1,2,3-triazol-1-yl]-3-deoxy-1-thio-α-D-galactopyranoside (40.0 mg, 0.0597 mmol) in MeOH/TEA/H$_2$O (0.5/0.3/0.1)(5 mL) was stirred at room temperature for 4 h. The mixture was evaporated to dryness and the crude product was purified by Prep-HPLC to afford 20.0 mg (62%) of the title compound. $^1$H NMR (400 MHz, MeOD) δ 8.67 (d, J=2.0 Hz, 1H), 8.63-8.56 (m, 2H), 7.46 (s, 1H), 6.21 (d, J=5.4 Hz, 1H), 5.13 (dd, J=11.4, 2.8 Hz, 1H), 4.99 (dd, J=11.3, 5.4 Hz, 1H), 4.37 (t, J=6.2 Hz, 1H), 4.22 (d, J=2.0 Hz, 1H), 3.72-3.63 (m, 2H). m/z calcd for [C$_{17}$H$_{14}$BrClN$_6$O$_4$S$_2$][M+H]$^+$: 544; found: 545.

Example 5

5-Chloro-2-cyano-pyridine-3-yl 3-[4-(4-chlorothiazol-2-yl)-1H-1,2,3-triazol-1-yl]-3-deoxy-1-thio-α-D-galactopyranoside

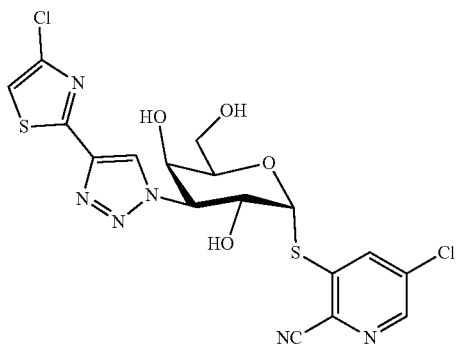

A solution of 5-chloro-2-cyano-pyridine-3-yl 2,4,6-tri-O-acetyl-3-[4-(4-chlorothiazol-2-yl)-1H-1,2,3-triazol-1-yl]-3-deoxy-1-thio-α-D-galactopyranoside (46.0 mg, 0.0733 mmol) in 5 mL of MeOH/TEA/H$_2$O (5/3/1) was stirred at room temperature for 4 h. The mixture was evaporated to dryness and the crude product was purified by Prep-HPLC to afford the title compound 21.4 mg (58.1%) as a white solid. $^1$H NMR (400 MHz, MeOD) δ 8.61 (s, 1H), 8.56 (d, J=2.2 Hz, 1H), 8.44 (d, J=2.2 Hz, 1H), 7.46 (s, 1H), 6.22 (d, J=5.4 Hz, 1H), 5.13 (dd, J=11.3, 2.8 Hz, 1H), 4.99 (dd, J=11.3, 5.4 Hz, 1H), 4.36 (t, J=6.0 Hz, 1H), 4.24-4.18 (m, 1H), 3.71-3.64 (m, 2H). m/z calcd for [C$_{17}$H$_{15}$Cl$_2$N$_6$O$_4$S$_2$]$^+$ [M+H]$^+$: 501.0; found: 501.1.

Example 6

5-Bromo-6-cyano-3-pyridyl 3-[4-(4-chlorothiazol-2-yl)-1H-1,2,3-triazol-1-yl]-3-deoxy-1-thio-α-D-galactopyranoside

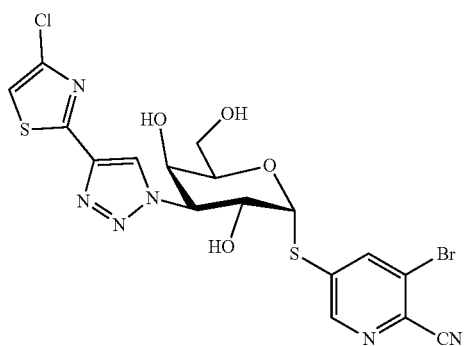

To a solution of 5-bromo-6-cyano-3-pyridyl 2,4,6-tri-O-acetyl-3-[4-(4-chlorothiazol-2-yl)-1H-1,2,3-triazol-1-yl]-3-deoxy-1-thio-α-D-galactopyranoside (57.0 mg, 0.0908 mmol) in 5 mL of MeOH/TEA/H$_2$O (5/3/1) was stirred at room temperature for 4 h. The mixture was evaporated to dryness and the crude product was purified by Prep-HPLC to afford the title compound 25.9 mg (56.9%) as a white solid. $^1$H NMR (400 MHz, MeOD) δ 8.76 (d, J=1.9 Hz, 1H), 8.60 (s, 1H), 8.47 (d, J=1.9 Hz, 1H), 7.46 (s, 1H), 6.18 (d, J=5.3 Hz, 1H), 5.09 (dd, J=11.4, 2.8 Hz, 1H), 4.97 (dd, J=11.4, 5.3 Hz, 1H), 4.35 (t, J=6.0 Hz, 1H), 4.23-4.19 (m, 1H), 3.75-3.66 (m, 2H). m/z calcd for [C$_{17}$H$_{15}$BrClN$_6$O$_4$S$_2$]$^+$ [M+H]$^+$: 544.95; found: 545.0.

Example 7

3,4-Dichlorophenyl 3-[4-(2-chlorothiazol-4-yl)-1H-1,2,3-triazol-1-yl]-3-deoxy-1-thio-α-D-galactopyranoside

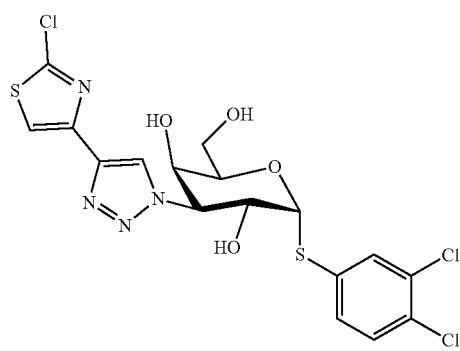

To a solution of 3,4-dichlorophenyl 2,4,6-tri-O-acetyl 3-[4-(2-chlorothiazol-4-yl)-1H-1,2,3-triazol-1-yl]-3-deoxy-1-thio-α-D-galactopyranoside (10.0 mg, 0.0157 mmol) in MeOH/TEA/H$_2$O (0.5/0.3/0.1)(1 mL) was stirred at room temperature with for 4 h. The mixture was evaporated to dryness and the crude product was purified by prep-HPLC to afford the title compound as a white solid (1.91 mg, 0.00322 mmol, yield: 20.5%). $^1$H NMR (400 MHz, MeOD) δ 8.40 (s, 1H), 7.86 (s, 1H), 7.80 (d, J=1.7 Hz, 1H), 7.58-7.51 (m, 1H), 7.48 (d, J=8.4 Hz, 1H), 5.84 (d, J=5.3 Hz, 1H), 4.99 (dd, J=11.5, 2.7 Hz, 1H), 4.91 (dd, J=11.5, 5.3 Hz, 1H), 4.48 (t, J=6.5 Hz, 1H), 4.20 (d, J=2.2 Hz, 1H), 3.76-3.65 (m, 2H). m/z calcd for [C$_{17}$H$_{15}$Cl$_3$N$_4$O$_4$S$_2$]$^+$ [M+H]$^+$: 509.0; found: 509.0.

Example 8

3,4-Dichlorophenyl 3-deoxy-3-[4-(2-fluorothiazol-4-yl)-1H-1,2,3-triazol-1-yl]-1-thio-α-D-galactopyranoside

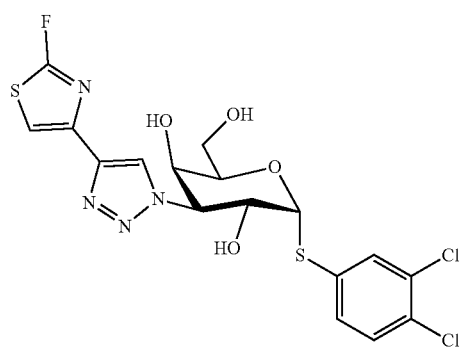

This compound is made via process a24 or a1 as described above.

Example 9

3,4-Dichlorophenyl 3-deoxy-3-[4-(4-fluorothiazol-2-yl)-1H-1,2,3-triazol-1-yl]-1-thio-α-D-galactopyranoside

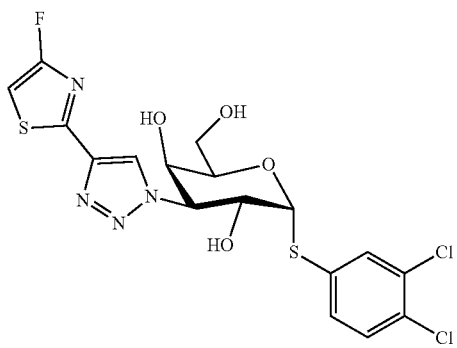

This compound is made via process a25 or a1 as described above.

Example 10

3,4-Dichlorophenyl 3-deoxy-3-[4-(4,5-difluorothiazol-2-yl)-1H-1,2,3-triazol-1-yl]-1-thio-α-D-galactopyranoside

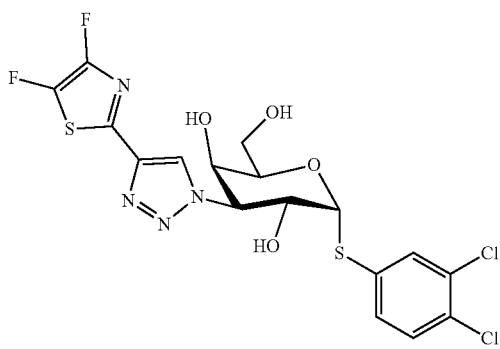

This compound is made via process a25 or a1 as described above.

Example 11

3,4-Dichlorophenyl 3-deoxy-3-[4-(4-hydroxythiazol-2-yl)-1H-1,2,3-triazol-1-yl]-1-thio-α-D-galactopyranoside

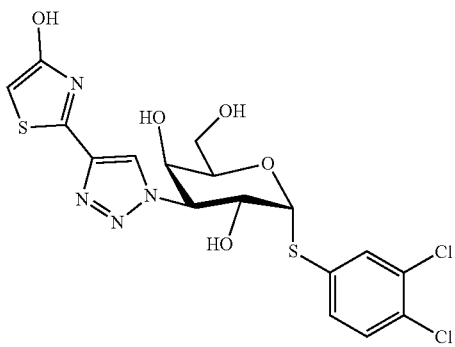

A solution of 3,4-dichlorophenyl 2,4,6-tri-O-acetyl-3-deoxy-3-[4-(4-hydroxythiazol-2-yl)-1H-1,2,3-triazol-1-yl]-1-thio-α-D-galactopyranoside (60.0 mg, 0.0972 mmol) in MeOH (2 mL) and the pH was adjusted to 8-9 by addition of sodium methoxide. The reaction was stirred at room temperature for 2 h. The mixture was evaporated to dryness under low temperature and the crude product was purified by Prep-HPLC to afford the title compound 10.0 mg (21%). 1H NMR (400 MHz, MeOD) δ 8.66 (dd, J=94.9, 48.9 Hz, 1H), 7.79 (d, J=2.1 Hz, 1H), 7.56-7.43 (m, 2H), 5.83 (dd, J=7.7, 4.7 Hz, 1H), 5.02 (s, 1H), 4.95-4.86 (m, 3H), 4.47 (d, J=5.2 Hz, 1H), 4.23-4.12 (m, 1H), 3.70 (t, J=6.0 Hz, 2H). m/z calcd for $[C_{17}H_{16}C_{12}N_4O_5S_2]$ [M+H]$^+$: 617.0; found: 617.0.

Example 12

3,4-Dichlorophenyl 3-deoxy-3-[4-(2-hydroxythiazol-4-yl)-1H-1,2,3-triazol-1-yl]-1-thio-α-D-galactopyranoside

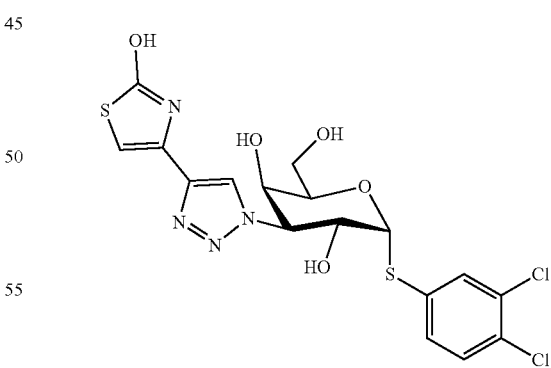

A solution of 3,4-dichlorophenyl 2,4,6-tri-O-acetyl-3-deoxy-3-[4-(2-hydroxythiazol-4-yl)-1H-1,2,3-triazol-1-yl]-1-thio-α-D-galactopyranoside (23.0 mg, 0.0372 mmol) in MeOH/TEA/H$_2$O (0.5/0.3/0.1)(0.9 mL) was stirred at room temperature for 4 h. The mixture was evaporated to dryness and the crude product was purified by Prep-HPLC to afford the title compound as a white solid 10.0 mg (27%). $^1$H NMR (400 MHz, MeOD) δ 8.35 (s, 1H), 7.79 (d, J=2.0 Hz, 1H), 7.53 (dd, J=8.4, 2.0 Hz, 1H), 7.47 (d, J=8.4 Hz, 1H), 6.69 (s, 1H), 5.83 (d, J=5.3 Hz, 1H), 4.98 (dd, J=11.4, 2.8 Hz, 1H), 4.83 (dd, J=11.4, 5.3 Hz, 1H), 4.47 (t, J=6.0 Hz, 1H), 4.18 (d, J=2.0 Hz, 1H), 3.76-3.64 (m, 2H). m/z calcd for $[C_{17}H_{16}Cl_2N_4O_5S_2]^+$ $[M+H]^+$: 491.0; found: 491.2.

Example 13

5-Chloro-6-cyano-pyridine-3-yl 3-deoxy-3-[4-(2-hydroxythiazol-4-yl)-1H-1,2,3-triazol-1-yl]-1-thio-α-D-galactopyranoside

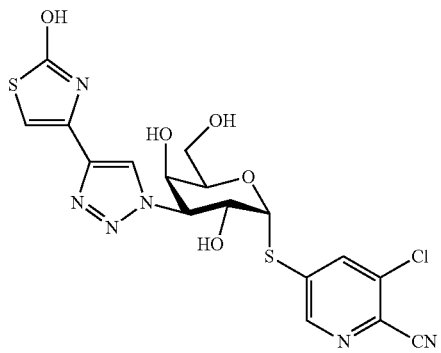

To a solution of 5-chloro-6-cyano-pyridine-3-yl 2,4,6-tri-O-acetyl 3-deoxy-3-[4-(2-hydroxythiazol-4-yl)-1H-1,2,3-triazol-1-yl]-1-thio-α-D-galactopyranoside (60.0 mg, 0.099 mmol) in MeOH (5.00 mL) was added TEA (0.841 mL, 6.03 mmol) and water (280 mg, 16 mmol). The mixture was stirred at rt for overnight followed by removal of the solvents. The residue was purified by C-18 column to obtain the title compound (16.0 mg, 0.053 mmol, yield: 54%). $^1$H NMR (400 MHz, MeOD) δ 8.74 (d, J=1.9 Hz, 1H), 8.41-8.33 (m, 2H), 6.72 (s, 1H), 6.21 (d, J=5.3 Hz, 1H), 5.07 (dd, J=11.3, 2.9 Hz, 1H), 4.95 dd, J=11.3, 5.3 Hz, 1H), 4.35 (t, J=6.0 Hz, 1H), 4.18 (s, 1H), 3.70 (d, J=6.0 Hz, 2H). m/z calcd for $[C_{17}H_{15}CN_6O_5S_2]^+$ $[M+H]^+$: 482.9; found: 483.

Example 14

5-Bromo-2-cyano-pyridine-3-yl 3-deoxy-3-[4-(2-hydroxythiazol-4-yl)-1H-1,2,3-triazol-1-yl]-1-thio-α-D-galactopyranoside

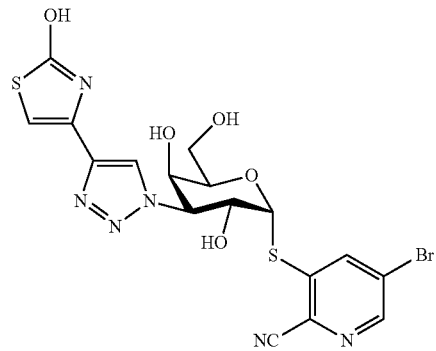

To a solution of 5-bromo-2-cyano-pyridine-3-yl 2,4,6-tri-O-acetyl-3-deoxy-3-[4-(2-hydroxythiazol-4-yl)-1H-1,2,3-triazol-1-yl]-1-thio-α-D-galactopyranoside (25.0 mg, 0.0383 mmol) in the MeOH (5.00 mL) was added TEA (0.841 mL, 6.03 mmol) and water (280 mg, 15.6 mmol). The mixture was stirred at rt for overnight. Removal of solvent gave a residue which was purified by Prep HPLC to obtain the title compound (8.00 mg, 0.015 mmol, yield: 40%). $^1$H NMR (400 MHz, MeOD) δ 8.69 (d, J=2.0 Hz, 1H), 8.61 (d, J=2.0 Hz, 1H), 8.34 (s, 1H), 6.71 (s, 1H), 6.22 (d, J=5.4 Hz, 1H), 5.08 (dd, J=11.3, 2.8 Hz, 1H), 4.96 (dd, J=11.4, 5.4 Hz, 1H), 4.37 (t, J=6.0 Hz, 1H), 4.22 (s, 1H), 3.72-3.63 (m, 2H). m/z calcd for $[C_{17}H_{15}BrN_6O_5S_2]^+$ $[M+H]^+$: 527; found: 527.

Example 15

5-Bromo-6-cyano-3-pyridyl 3-deoxy-3-[4-(2-hydroxythiazol-4-yl)-1H-1,2,3-triazol-1-yl]-1-thio-α-D-galactopyranoside

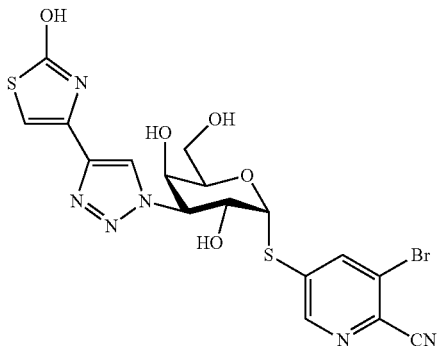

To a solution of 5-bromo-6-cyano-3-pyridyl 2,4,6-tri-O-acetyl 3-deoxy-3-[4-(2-hydroxythiazol-4-yl)-1H-1,2,3-triazol-1-yl]-1-thio-α-D-galactopyranoside (45.0 mg, 0.069 mmol) in the MeOH (5.00 mL) was added TEA (0.841 mL, 6.03 mmol) and water (280 mg, 15.6 mmol). The mixture was stirred at rt for overnight. Removal of solvent gave a residue which was purified by Prep HPLC to obtain the title compound (16.0 mg, 0.0303 mmol, yield: 44.1%). $^1$H NMR (400 MHz, MeOD) δ 8.78 (d, J=1.8 Hz, 1H), 8.49 (d, J=1.9 Hz, 1H), 8.38 (s, 1H), 6.72 (s, 1H), 6.20 (d, J=5.3 Hz, 1H), 5.06 (dd, J=11.4, 2.8 Hz, 1H), 4.93 (dd, J=11.4, 5.4 Hz, 1H), 4.36 (t, J=6.0 Hz, 1H), 4.19 (s, 1H), 3.71 (d, J=6.0 Hz, 2H). m/z calcd for $[C_{17}H_{15}BrN_6O_5S_2]^+$ $[M+H]^+$: 527; found: 527.

Example 16

5-Chloro-2-cyano-3-pyridyl 3-deoxy-3-[4-(2-hydroxythiazol-4-yl)-1H-1,2,3-triazol-1-yl]-1-thio-α-D-galactopyranoside

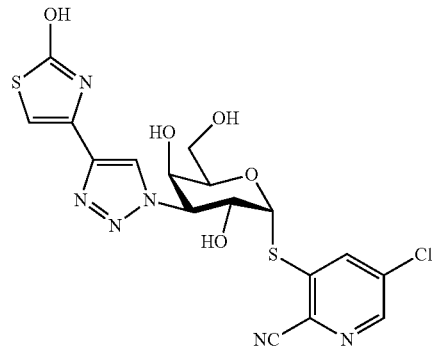

To a solution of 5-chloro-2-cyano-3-pyridyl 2,4,6-tri-O-acetyl-3-deoxy-3-[4-(2-hydroxythiazol-4-yl)-1H-1,2,3-triazol-1-yl]-1-thio-α-D-galactopyranoside (45.0 mg, 0.0739 mmol) in MeOH (5.00 mL) was added TEA (0.841 mL, 6.03 mmol) and water (280 mg, 15.6 mmol). The mixture was stirred at rt for overnight. Removal of solvent gave a residue which was purified by Prep-HPLC to obtain the title compound (20.0 mg, 0.0414 mmol, yield: 56.1%). $^1$H NMR (400 MHz, MeOD) δ 8.47 (d, J=2.1 Hz, 1H), 8.34 (d, J=2.1 Hz, 1H), 8.27 (s, 1H), 6.60 (s, 1H), 6.12 (d, J=5.3 Hz, 1H), 4.98 (dd, J=11.5, 2.5 Hz, 1H), 4.85 (dd, J=11.3, 5.4 Hz, 2H), 4.25 (t, J=6.1 Hz, 1H), 4.10 (s, 1H), 3.57 (d, J=6.0 Hz, 2H). m/z calcd for $[C_{17}H_{15}ClN_6O_5S_2]^+[M+H]^+$: 482.9; found: 483.0.

Example 17

5-Chloro-6-trifluoromethyl-pyridin-3-yl 3-deoxy-3-[4-(2-hydroxythiazol-4-yl)-1H-1,2,3-triazol-1-yl]-1-thio-α-D-galactopyranoside

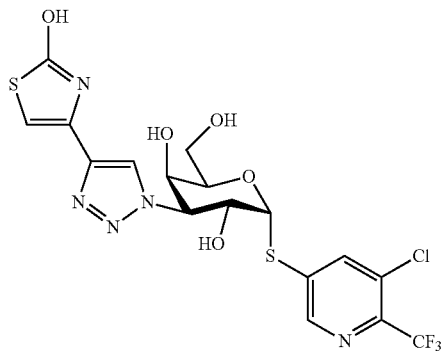

To a solution of 5-Bromo-6-trifluoromethyl-pyridin-3-yl 2,4,6-tri-O-acetyl-3-deoxy-3-[4-(2-hydroxythiazol-4-yl)-1H-1,2,3-triazol-1-yl]-1-thio-α-D-galactopyranoside (12.0 mg, 0.0184 mmol) in the MeOH (5.00 mL) was added TEA (0.841 mL, 6.03 mmol) and water (280 mg, 15.6 mmol). The mixture was stirred at rt overnight. Removal of solvent gave a residue which was purified by C-18 column to obtain the title compound (2.45 mg, 0.00466 mmol, yield: 25.3%). $^1$H NMR (400 MHz, MeOD) δ 8.72 (d, J=1.6 Hz, 1H), 8.40-8.32 (m, 2H), 6.71 (s, 1H), 6.14 (d, J=5.5 Hz, 1H), 5.05 (dd, J=11.8, 2.9 Hz, 1H), 4.95 (dd, J=11.8, 5.4 Hz, 1H), 4.41 (t, J=5.5 Hz, 1H), 4.19 (d, J=2.3 Hz, 1H), 3.71 (d, J=6.4 Hz, 2H). m/z calcd for $[C_{17}H_{12}ClF_3N_5O_5S_2]^+$ [M+H]$^+$: 526.0; found: 526.0.

Example 18

3,5-Dichloro-4-fluoro-phenyl 3-deoxy-3-[4-(2-hydroxythiazol-4-yl)-1H-1,2,3-triazol-1-yl]-1-thio-α-D-galactopyranoside

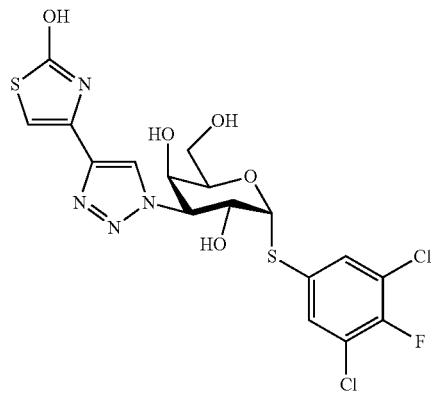

To a solution of 3,5-Dichloro-4-fluoro-phenyl 3-2,4,6-tri-O-acetyl-deoxy-3-[4-(2-hydroxythiazol-4-yl)-1H-1,2,3-triazol-1-yl]-1-thio-α-D-galactopyranoside (70.0 mg, 0.110 mmol) in MeOH/TEA/H$_2$O (5/3/1)(2 mL) was stirred at room temperature for 4 h. The mixture was evaporated to dryness and the crude product was purified by prep-HPLC to afford the title compound as a white solid (9.00 mg, 0.0177 mmol, yield: 16.0%). $^1$H NMR (400 MHz, MeOD) δ 8.26 (s, 1H), 7.63 (d, J=6.3 Hz, 2H), 6.60 (s, 1H), 5.72 (d, J=5.3 Hz, 1H), 4.88 (dd, J=11.4, 2.8 Hz, 1H), 4.74 (dd, J=11.4, 5.3 Hz, 1H), 4.38 (t, J=6.0 Hz, 1H), 4.08 (d, J=2.0 Hz, 1H), 3.66-3.56 (m, 2H).

m/z calcd for $[C_7H_{12}C_2FN_4O_5S_2]^+$ [M+H]$^+$: 509.0; found: 509.0.

Example 19

3-Chloro-4-fluoro-phenyl 3-deoxy-3-[4-(2-hydroxythiazol-4-yl)-1H-1,2,3-triazol-1-yl]-1-thio-α-D-galactopyranoside

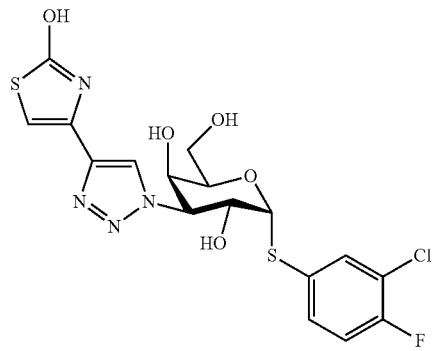

Example 20

3,4,5-trichlorophenyl 3-deoxy-3-[4-(2-hydroxythiazol-4-yl)-1H-1,2,3-triazol-1-yl]-1-thio-α-D-galactopyranoside

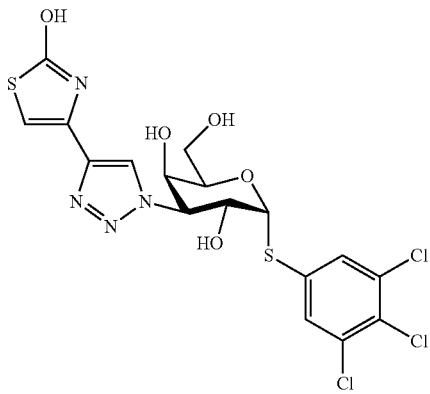

To a solution of 3,4,5-trichlorophenyl 2,4,6-tri-O-acetyl-3-[4-(2-hydroxythiazol-4-yl)triazol-1-yl]-3-deoxy-1-thio-α-D-galactopyranoside (35.0 mg, 0.0537 mmol) in the MeOH (2 mL) was added TEA (1.00 mL, 7.17 mmol) and water (19.3 mg, 1.07 mmol). The mixture was stirred at rt for overnight. After concentration, the residue was purified by column chromatography (MeCN/H$_2$O=10/1~95/5, C-18 column, 10 mL/min, UV 254) to obtain the title compound (15.0 mg, 0.030 mmol, yield: 52%). $^1$H NMR (400 MHz, MeOD) δ 8.24 (s, 1H), 7.67 (s, 2H), 6.59 (s, 1H), 5.81 (d, J=5.3 Hz, 1H), 4.88 (dd, J=11.3, 2.6 Hz, 1H), 4.79 (m, 1H), 4.34 (t, J=5.9 Hz, 1H), 4.08 (s, 1H), 3.67-3.55 (m, 2H). m/z calcd for [C$_{17}$H$_{15}$Cl$_3$N$_4$O$_5$S$_2$]: [M+1]$^+$: 525.0; found: 525.

Example 21

3,5-dibromo-4-fluorophenyl 3-deoxy-3-[4-(2-hydroxythiazol-4-yl)-1H-1,2,3-triazol-1-yl]-1-thio-α-D-galactopyranoside

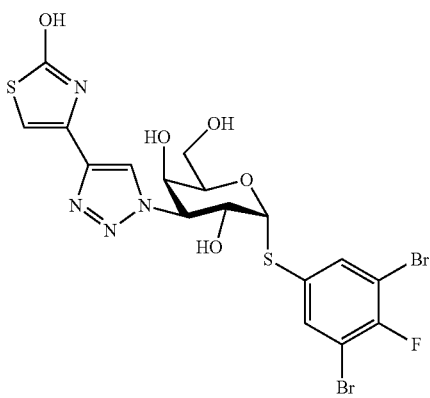

A solution of 3,5-dibromo-4-fluorophenyl 2,4,6-tri-O-acetyl-3-deoxy-3-[4-(2-hydroxythiazol-4-yl)-1H-1,2,3-triazol-1-yl]-1-thio-α-D-galactopyranoside (50.0 mg, 0.0690 mmol) in MeOH/Et$_3$N/H$_2$O (0.5/0.3/0.1)(0.9 mL) was stirred at room temperature for 4 hours followed by removal of solvent by evaporation. The residue was purified by preparative HPLC (X-Select10 um 19*250 mm, 20 mL/min, MeOH/H$_2$O (10 mM NH$_4$HCO$_3$)=20%~90%) to afford the title compound as a white solid (16.0 mg, 0.0267 mmol, yield: 38.7%). $^1$H NMR (400 MHz, MeOD) δ 8.32 (s, 1H), 7.88 (d, J=5.9 Hz, 2H), 6.68 (s, 1H), 5.79 (d, J=5.3 Hz, 1H), 4.96 (dd, J=11.4, 2.7 Hz, 1H), 4.84 (d, J=6.1 Hz, 1H), 4.47 (t, J=6.0 Hz, 1H), 4.16 (d, J=1.8 Hz, 1H), 3.71 (dd, J=6.0, 2.0 Hz, 2H). m/z calcd for [C$_{17}$H$_{12}$Br$_2$FN$_4$O$_4$S$_2$]$^+$ [M+H]$^+$: 597; found: 597.

Example 22

3-Bromo-4-cyanophenyl 3-deoxy-3-[4-(2-hydroxythiazol-4-yl)-1H-1,2,3-triazol-1-yl]-1-thio-α-D-galactopyranoside

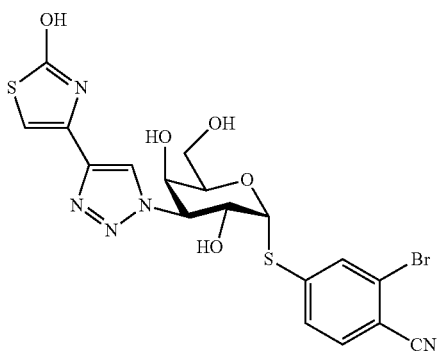

A solution of 3-bromo-4-cyanophenyl 2,4,6-tri-O-acetyl-3-deoxy-3-[4-(2-hydroxythiazol-4-yl)-1H-1,2,3-triazol-1-yl]-1-thio-α-D-galactopyranoside (30.0 mg, 0.0460 mmol) in MeOH (5.00 mL) was added TEA (0.841 mL, 6.03 mmol) and water (280 mg, 15.6 mmol). The mixture was stirred at room temperature overnight. Removal of solvent gave a residue. The residue was purified by column chromatography (MeCN/H$_2$O=1/20~3/1, C-18 column, 20 mL/min, UV 254) to obtain the title compound (95.0%, 20.0 mg, 0.0361 mmol, yield: 78.5%). 1H NMR (400 MHz, MeOD) δ 8.26 (s, 1H), 7.91 (s, 1H), 7.64-7.51 (m, 2H), 6.60 (s, 1H), 5.99 (d, J=5.3 Hz, 1H), 4.90 (d, J=2.8 Hz, 1H), 4.83-4.78 (m, 1H), 4.27 (s, 1H), 4.08 (s, 1H), 3.65-3.51 (m, 2H). m/z calcd for [C$_{18}$H$_{16}$BrN$_5$O$_5$S$_2$]: [M+1]$^+$: 526; found: 526.

Example 23

5-Bromo-6-trifluoromethyl-3-pyridyl 3-deoxy-3-[4-(2-hydroxythiazol-4-yl)-1H-1,2,3-triazol-1-yl]-1-thio-α-D-galactopyranoside

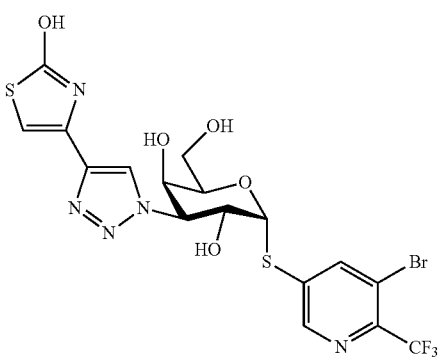

A solution of 5-bromo-6-trifluoromethyl-3-pyridyl 2,4,6-tri-O-acetyl-3-deoxy-3-[4-(2-hydroxythiazol-4-yl)-1H-1,2,3-triazol-1-yl]-1-thio-α-D-galactopyranoside (65.0 mg, 0.0933 mmol) in MeOH/Et$_3$N/H$_2$O (5/3/1, 8 mL) was stirred at room temperature overnight. The solvents were removed by evaporation to afford crude product which was purified by Prep HPLC (X-Select10 um 19*250 mm, 20 mL/min, MeCN/H$_2$O (10 mM NH$_4$HCO$_3$)=20%~80%) to give the title compound as white solid (21.0 mg, 0.0368 mmol, yield: 39.5%). $^1$H NMR (400 MHz, MeOD) δ 8.76 (d, J=1.7 Hz, 1H), 8.52 (s, 1H), 8.39 (s, 1H), 6.72 (s, 1H), 6.13 (d, J=5.3 Hz, 1H), 5.06 (dd, J=11.3, 2.9 Hz, 1H), 4.93 (dd, J=11.3, 5.4 Hz, 1H), 4.42 (t, J=6.4 Hz, 1H), 4.21 (s, 1H), 3.77-3.66 (m, 2H). m/z calcd for [C$_7$H$_{15}$BrF$_3$NO$_5$S$_2$] [M+H]$^+$: 572; found: 572.

Example 24

3-Chloro-4-trifluoromethylphenyl 3-deoxy-3-[4-(2-hydroxythiazol-4-yl)-1H-1,2,3-triazol-1-yl]-1-thio-α-D-galactopyranoside

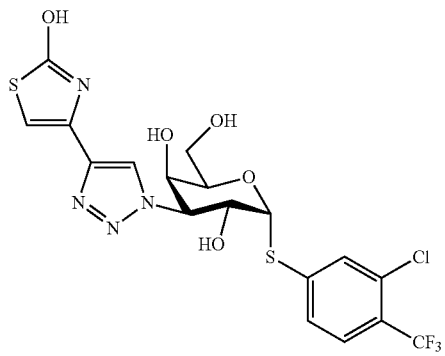

To a solution of 3-chloro-4-trifluoromethylphenyl 2,4,6-tri O-acetyl-3-deoxy-3-[4-(2-hydroxythiazol-4-yl)-1H-1,2,3-triazol-1-yl]-1-thio-α-D-galactopyranoside (30.0 mg, 0.0461 mmol) in MeOH (5.00 mL) was added TEA (704 mg, 6.96 mmol) and water (323 mg, 17.9 mmol). The reaction mixture was stirred at room temperature overnight. Removal of solvent gave a residue. The residue was purified by column chromatography (MeCN/H$_2$O=1/20~1/5, C-18 column, 20 mL/min, UV 254) to obtain 1-(3-chloro-4-(trifluoromethyl)phenyl)-3-[4-(2-hydroxythiazol-4-yl)-1H-1,2,3-triazol-1-yl]-1,3-dideoxy-1-thio-α-D-galactopyranoside (9.00 mg, yield: 36.5%). $^1$H NMR (400 MHz, CDCl$_3$) δ 8.26 (s, 1H), 7.73 (s, 1H), 7.58 (s, 2H), 6.60 (s, 1H), 5.95 (s, 1H), 4.89 (d, J=11.6 Hz, 1H), 4.81 (m, 1H), 4.31 (m, 1H), 4.08 (m, 1H), 3.60 (m, 2H). m/z calcd for [C$_{18}$H$_{16}$ClF$_3$N$_4$O$_5$S$_2$] [M+1]$^+$: 525; found: 525.

Example 25

3-Chloro-4-trifluoromethylthiophenol 3-deoxy-3-[4-(2-hydroxythiazol-4-yl)-1H-1,2,3-triazol-1-yl]-1-thio-α-D-galactopyranoside

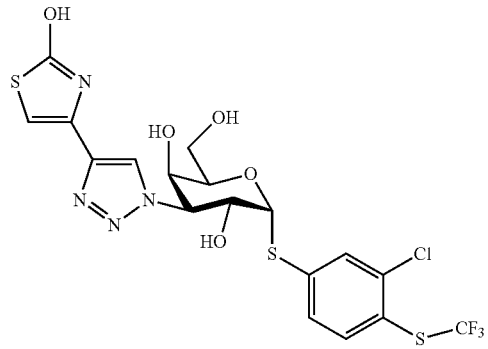

This compound is made via process a1 or a2 described above.

Example 26

3-Chloro-4-methylphenyl 3-deoxy-3-[4-(2-hydroxythiazol-4-yl)-1H-1,2,3-triazol-1-yl]-1-thio-α-D-galactopyranoside

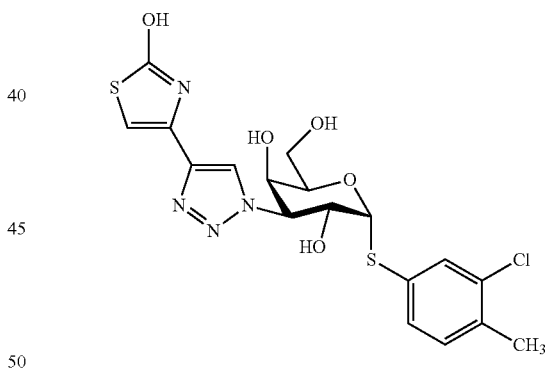

A solution of 3-chloro-4-methylphenyl 2,4,6-tri-O-acetyl-3-deoxy-3-[4-(2-hydroxythiazol-4-yl)-1H-1,2,3-triazol-1-yl]-1-thio-α-D-galactopyranoside (50.0 mg, 0.0837 mmol) in MeOH/Et$_3$N/H$_2$O (5/3/1)(8 mL) was stirred at room temperature overnight. After removal of the solvents, the residue was purified by Prep HPLC (X-Select10 um 19*250 mm, 20 mL/min, MeCN/H$_2$O (10 mM NH$_4$HCO$_3$)=30%~90%) to give the title compound (20.6 mg, 0.0437 mmol, yield: 52.2%) as white solid. $^1$H NMR (400 MHz, MeOD) δ 8.35 (s, 1H), 7.62 (d, J=1.5 Hz, 1H), 7.43 (dd, J=7.9, 1.6 Hz, 1H), 7.25 (d, J=7.9 Hz, 1H), 6.69 (s, 1H), 5.73 (d, J=5.3 Hz, 1H), 4.97 (dd, J=11.5, 2.7 Hz, 1H), 4.83-4.77 (m, 1H), 4.52 (t, J=6.2 Hz, 1H), 4.18 (d, J=1.9 Hz, 1H), 3.70 (qd, J=11.4, 6.2 Hz, 2H), 2.35 (s, 3H). m/z calcd for [C$_{18}$H$_{19}$CN$_4$O$_5$S$_2$] [M+H]$^+$: 471; found: 471.

Example 27

5-Chloro-picolinamide-3-yl 3-[4-(4-chlorothiazol-2-yl)-1H-1,2,3-triazol-1-yl]-3-deoxy-1-thio-α-D-galactopyranoside

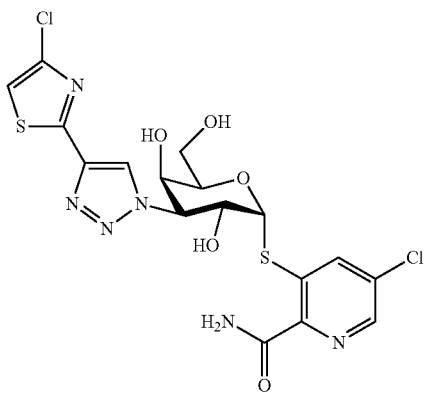

This compound is made via process a1 or a2 described above.

Example 28

2-carboxy-5-chloropyridyl 3-deoxy-3-[4-(2-hydroxythiazol-4-yl)-1H-1,2,3-triazol-1-yl]-1-thio-α-D-galactopyranoside

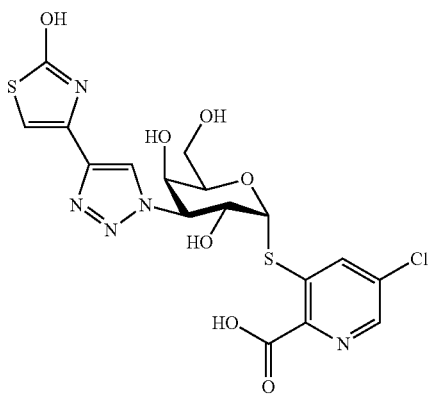

A stirred solution of 5-chloro-2-(methoxycarbonyl)pyridin-3-yl 2,4,6-tri-O-acetyl-3-deoxy-3-[4-(2-hydroxythiazol-4-yl)-1H-1,2,3-triazol-1-yl]-1-thio-α-D-galactopyranoside (200.0 mg, 0.311 mmol) in MeOH (5 mL) was added TEA (2 mL) and H₂O (1 mL). The reaction was stirred at room temperature for 24 hours. LiOH.H₂O (65.4 mg, 1.56 mmol) was added and the reaction was stirred at room temperature for 4 hours. Acidic resin was added into the solution and the pH value was adjusted to 3~4. After filtration, the solvent was removed and the obtained residue was purified twice by Preparative HPLC (X-Select10 um 19*250 mm, 20 m/min, MeCN/H₂O=0%~10%) to afford the title compound (10 mg, 0.02 mmol, yield: 6.4%). $^1$H NMR (400 MHz, D₂O) δ 8.44 (s, 1H), 8.42 (s, 1H), 8.27 (s, 1H), 6.80 (s, 1H), 6.06 (d, J=5.5 Hz, 1H), 5.20 (dd, J=11.4, 2.8 Hz, 1H), 5.00 (dd, J=11.6, 5.5 Hz, 1H), 4.58 (dd, J=7.7, 4.4 Hz, 1H), 4.29 (d, J=2.4 Hz, 1H), 3.78~3.68 (m, 2H). m/z calcd for [C₁₇H₁₆Cl₁N₅O₇S₂][M+1]⁺: 502, found: 502.

Example 29

5-Bromo-6-trifluoromethyl-pyridine-3-yl 3-deoxy-3-[4-(4,5-dichlorothiazol-2-yl)-1H-1,2,3-triazol-1-yl]-1-thio-α-D-galactopyranoside

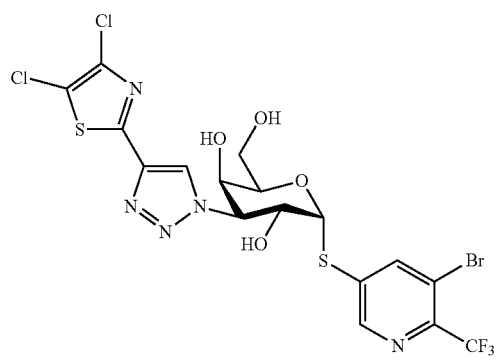

A solution of 5-bromo-6-(trifluoromethyl)pyridin-3-yl 3-deoxy-3-[4-(4,5-dichlorothiazol-2-yl)-1H-1,2,3-triazol-1-yl]-1-thio-α-D-galactopyranoside (45.0 mg, 0.0601 mmol) in MeOH/TEA/H₂O (5/3/1) (2 mL) was stirred at room temperature for 4 hours. The solvents were evaporated and the crude product was purified by prep HPLC (X-Select10 μm 19*250 mm, 20 mL/min, MeCN/H₂O (10 mM NH₄HCO₃)=20%~80%) to afford the title compound. (26.0 mg, 0.0417 mmol, yield: 69.5%). $^1$H NMR (400 MHz, MeOD) δ 8.76 (d, J=1.6 Hz, 1H), 8.63 (s, 1H), 8.52 (s, 1H), 6.13 (d, J=5.3 Hz, 1H), 5.11 (dd, J=11.3, 2.8 Hz, 1H), 4.98 (dd, J=11.3, 5.3 Hz, 1H), 4.42 (t, J=6.1 Hz, 1H), 4.22 (s, 1H), 3.78-3.66 (m, 2H). m/z calcd for [C₁₇H₁₀BrCl₂F₃N₅O₄S₂][M+H]⁺: 622; found: 622.

Example 30

5-Bromo-2-isopropyl-pyridine-3-yl 3-[4-(4-chlorothiazol-2-yl)-1H-1,2,3-triazol-1-yl]-3-deoxy-1-thio-α-D-galactopyranoside

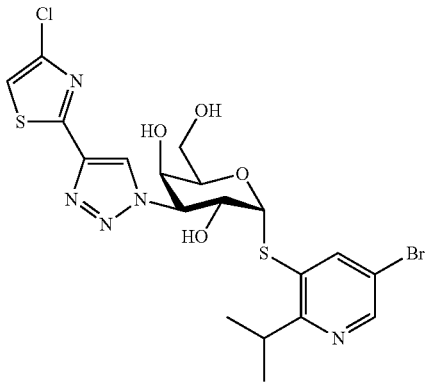

Example 31

3,4-Dichloro-6-fluoro-phenyl 3-deoxy-3-[4-(2-hydroxythiazol-4-yl)-1H-1,2,3-triazol-1-yl]-1-thio-α-D-galactopyranoside

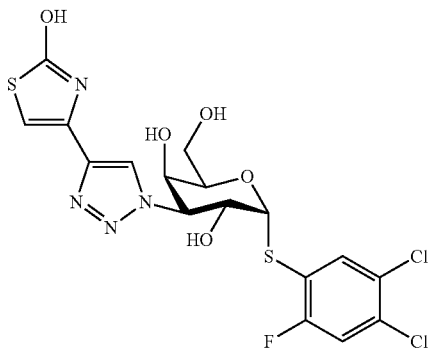

This compound is made via process a1 or a25 described above.

A solution of 3,4-dichloro-6-fluoro-phenyl 2,4,6-tri-O-acetyl-3-deoxy-3-[4-(2-hydroxythiazol-4-yl)-1H-1,2,3-triazol-1-yl]-1-thio-α-D-galactopyranoside (53.0 mg, 0.0834 mmol) in MeOH (3 mL) was added TEA (1.50 mL, 10.8 mmol), and water (500 mg, 27.8 mmol). The mixture was stirred at room temperature overnight. After concentration, the residue was purified by column chromatography (MeCN/H$_2$O=1/20~1/5, C-18 column, 15 mL/min, UV 254) to obtain the title compound (97.0%, 15.6 mg, 0.0297 mmol, yield: 35.6%). $^1$H NMR (400 MHz, MeOD) δ 8.35 (s, 1H), 7.89 (d, J=7.0 Hz, 1H), 7.44 (d, J=8.8 Hz, 1H), 6.69 (s, 1H), 5.93 (d, J=5.4 Hz, 1H), 5.05 (dd, J=11.4, 2.8 Hz, 1H), 4.88 (m, 1H), 4.39 (t, J=6.2 Hz, 1H), 4.18 (d, J=2.5 Hz, 1H), 3.71-3.50 (m, 2H). m/z calcd for [C$_{17}$H$_{15}$C$_{12}$FN$_4$O$_5$S$_2$] [M+1]$^+$: 509, found: 509.

Example 32

4-Chloro-N,N'-dimethylbenzamide-2-yl 3-deoxy-3-[4-(2-hydroxythiazol-4-yl)-1H-1,2,3-triazol-1-yl]-1-thio-α-D-galactopyranoside

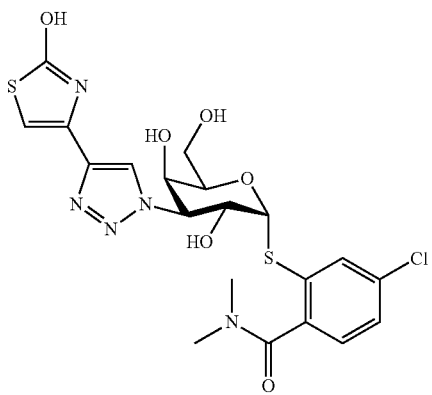

5-Chloro-N,N'-dimethyl-benzamid-2-yl 3-azido-3-deoxy-1-thio-α-D-galactopyranoside (53 mg, 0.13 mmol), 4-(2-trimethylsilylethynyl)thiazol-2-ol (39 mg, 0.20 mmol) and CuI (2.5 mg, 0.013 mmol) were dissolved in MeCN (3 mL) followed by addition of DIPEA (68 µL, 0.40 mmol) and stirring 16 h at 50° C. The mixture was concentrated and purification by HPLC (Cis, H$_2$O/MeCN/0.1% TFA) and freezedrying afforded the title compound as a white powder (53 mg, 76%). $^1$H NMR (400 MHz, Methanol-d$_4$) δ 8.35 (s, 1H), 7.86 (s, 1H), 7.42 (d, J=8.2 Hz, 1H), 7.27 (d, J=8.2, 1H), 6.69 (s, 1H), 5.91 (d, J=5.3 Hz, 1H), 4.96 (dd, J=11.5, 2.7 Hz, 1H), 4.87-4.85 (m, 1H), 4.47 (t, J=6.1 Hz, 1H), 4.18 (d, J=2.5 Hz, 1H), 3.76-3.65 (m, 2H), 3.13 (s, 3H), 2.89 (s, 3H). ESI-MS m/z calcd for [C$_{20}$H$_{22}$ClNO$_5$O$_6$S$_2$]$^+$ (M+H)$^+$: 528.1; found: 528.1.

Example 33

5-Chloro-N,N'-dimethyl-picolinamide-3-yl 3-deoxy-3-[4-(2-hydroxythiazol-4-yl)-1H-1,2,3-triazol-1-yl]-1-thio-α-D-galactopyranoside

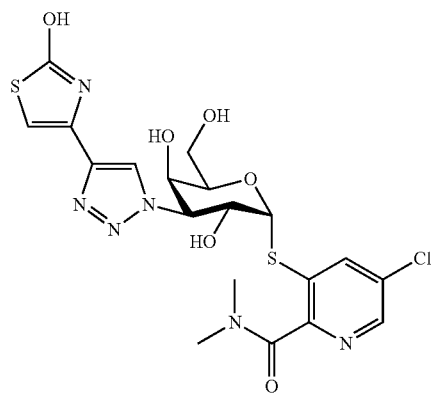

A solution of CuSO$_4$.5H$_2$O (5.5 mg, 0.022 mmol) and L-ascorbic acid sodium salt (8.7 mg, 0.044 mmol) in H$_2$O (0.5 mL) was added to a solution of 5-chloro-2-(dimethylcarbamoyl)-3-pyridyl 2,4,6-tri-O-acetyl-3-azido-3-deoxy-1-thio-α-D-galactopyranoside (116 mg, 0.22 mmol), 4-(2-trimethylsilylethynyl)thiazol-2-ol (65 mg, 0.33 mmol) and K$_2$CO$_3$ (303 mg, 2.19 mmol) in MeOH (3 mL) and THF (3 mL). After stirring 20 h at 50° C. CuI (10 mg, 0.053 mmol) was added and after stirring an additional 20 h at 50° C. the mixture was concentrated. Purification by HPLC (Cis, H$_2$O/MeCN/0.1% TFA) and freezedrying afforded the title compound as a white powder (6 mg, 5%)., $^1$H NMR (400 MHz, Methanol-d$_4$) δ 8.50 (d, J=1.5 Hz, 1H), 8.35 (s, 2H), 6.69 (s, 1H), 6.02 (d, J=5.3 Hz, 1H), 4.99 (dd, J=11.4, 2.7 Hz, 1H), 4.89-4.85 (m, 1H), 4.43 (t, J=6.1 Hz, 1H), 4.17 (d, J=2.5 Hz, 1H), 3.70 (d, J=6.0 Hz, 2H), 3.15 (s, 3H), 2.89 (s, 3H). ESI-MS m/z calcd for [C$_{19}$H$_{21}$ClN$_6$O$_6$S$_2$]$^+$ (M+H)$^+$: 529.1; found: 529.1.

Intermediates Used to Make Examples 1-33

Intermediate 1

5-Bromo-6-trifluoromethyl-pyridine-3-yl 2,4,6-tri-O-acetyl-3-[4-(4-chlorothiazol-2-yl)-1H-1,2,3-triazol-1-yl]-3-deoxy-1-thio-α-D-galactopyranoside 3-Bromo-5-fluoro-2-iodo-pyridine

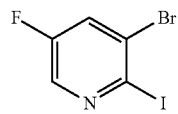

To a solution of 2,3-dibromo-5-fluoro-pyridine (5.00 g, 19.6 mmol) in MeCN (20 mL) were added NaI (8.82 g, 58.9 mmol) and trimethylsilyl chloride (2.12 g, 19.6 mmol). The reaction was stirred at room temperature for 2 h under $N_2$. Removal of solvent gave a residue which was purified by column chromatography (PE) to give the title compound (3.5 g, 44.8%). m/z calcd for $[C_5H_2BrFIN]^+$ $[M+H]^+$: 301.0; found: 301.0.

3-bromo-5-fluoro-2-(trifluoromethyl)pyridine

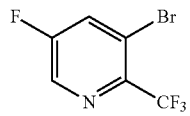

KF (423 mg, 7.29 mmol) and Iodocopper (1.26 g, 6.63 mmol) were thoroughly mixed before being heated under vacuum (1 mm Hg) with the flame of a Bunsen burner with gentle shaking until an homogeneous greenish color was obtained. NMP (20 mL), (Trifluoromethyl)trimethylsilane (942 mg, 6.63 mmol) was added. The mixture was stirred at 50° C. for 45 min followed by addition of 3-bromo-5-fluoro-2-iodo-pyridine (2 g, 6.63 mmol). The mixture was stirred at 50° C. for overnight. The reaction was monitored by GC-MS. Water (20 mL) was added to the mixture and extracted with EA (30 mL×3). The combined organic layers were washed with brine and evaporated to afford crude product, which was purified by flash chromatography on a Biotage® (EA/PE=1%~50%, ISCO® 40 g, 25 mL/min, normal phase silica gel, UV 254) to afford the title compound 1.15 g (71.1%) as a white solid. m/z calcd for $[C_6H_2BrF_4N]^+[M+H]^+$: 244.0; found: 244.0.

3-thiol 5-bromo-6-(trifluoromethyl)pyridine

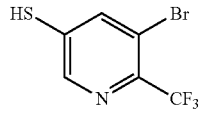

To a solution of 3-bromo-5-fluoro-2-(trifluoromethyl)pyridine (1.15 g, 4.71 mmol) in DMF (20 mL) was added sodium sulfide (1.245 g, 5.18 mmol). The reaction mixture was stirred at room temperature for 3 h. The pH was adjusted to pH-9 by adding 10% NaOH(aq). The mixture was extracted with $Et_2O$ (30 mL×3) and the aqueous layer was acidified with 2M $NaHSO_4$ to pH-3. The mixture was extracted with EA (20 mL×3). The combined organic layers were washed with brine and evaporated to afford crude product, which was purified by flash chromatography using a Biotage® (EA/PE=1%~50%, ISCO® 20 g, 15 mL/min, normal phase silica gel, UV 254) to afford the title compound 729 mg (60%) as a brown oil. m/z calcd for $[C_6H_3BrF_3NS]^+$ $[M+H]^+$: 257.0; found: 257.0.

5-Bromo-6-trifluoromethyl-pyridine-3-yl 2,4,6-tri-O-acetyl-3-azido-3-deoxy-1-thio-α-D-galactopyranoside

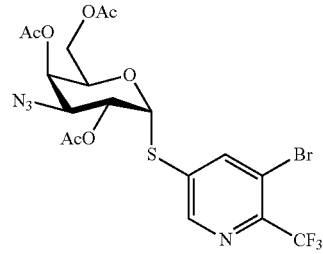

$Cs_2CO_3$ (1.40 g, 4.29 mmol) was added to a solution of 5-bromo-6-(trifluoromethyl)pyridine-3-thiol (738 mg, 2.86 mmol) in DMF (20 mL) at 0° C. The solution was stirred at rt for 30 min. Then 2,4,6-tri-O-acetyl-3-azido-3-deoxy-β-D-galactopyranosyl chloride (1.00 g, 2.86 mmol) was added to mixture. The reaction was stirred at 50° C. for 2 h. The mixture was cooled to room temperature followed by addition of water (30 mL). The aqueous phase was extracted with EtOAc (30 mL×3) and the combined organic layers were washed with brine, dried over $Na_2SO_4$ and concentrated in vacuo to afford crude product, which was purified by flash chromatography on a Biotage® (EA/PE=5%~40%, ISCO® 40 g, 30 mL/min, normal phase silica gel, uv 254) to afford the target compound (226 mg, 13.8%) as a white solid. m/z calcd for $[C_{18}H_{18}BrF_3N_4O_7S]+$ $[M+H]+$: 571.0; found: 571.0.

5-Bromo-6-trifluoromethyl-pyridine-3-yl 2,4,6-tri-O-acetyl-3-[4-(4-chlorothiazol-2-yl)-1H-1,2,3-triazol-1-yl]-3-deoxy-1-thio-α-D-galactopyranoside

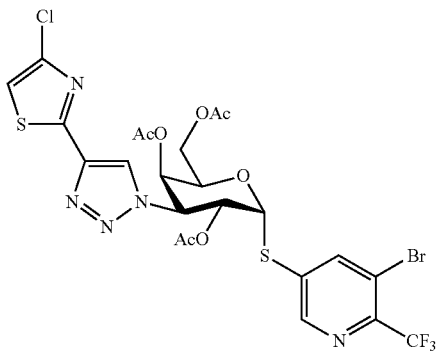

To a solution of 5-Bromo-6-trifluoromethyl-pyridine-3-yl 2,4,6-tri-O-acetyl-3-azido-3-deoxy-1-thio-α-D-galactopyranoside (80.0 mg, 0.140 mmol) in CH₃CN (2 mL) were added TEA (0.0976 mL) 0.700 mmol), Copper(I)Iodide (8.00 mg, 0.0420 mmol), CsF (31.9 mg, 0.210 mmol), 2-(4-chlorothiazol-2-yl)ethynyl-trimethyl-silane (45.3 mg, 0.210 mmol). The reaction was stirred at room temperature 20 h under a nitrogen atmosphere. Water (5 mL) and DCM (5 mL) were added and the phases were separated. The aqueous phase was extracted with DCM (10 mL×2) and the combined organic phases were washed with water (10 mL) and brine (10 mL), dried over anhydrous sodium sulphate. The solvents were removed and the crude material was purified by column chromatography (PE/EA=2/1) to give the title compound (50.0 mg, 50%) as a white solid. m/z calcd for $[C_{23}H_{20}BrClF_3N_5O_7S_2]^+$ $[M+H]^+$: 714.0; found: 714.0.

Intermediate 2

5-Bromo-6-trifluoromethyl-pyridine-3-yl 2,4,6-tri-O-acetyl-3-[4-(4-bromothiazol-2-yl)-1H-1,2,3-triazol-1-yl]-3-deoxy-1-thio-α-D-galactopyranoside 4-bromo-2-((trimethylsilyl)ethynyl)thiazole

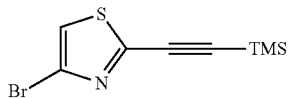

To a solution of 2,4-dibromothiazole (500 mg, 2.07 mmol) in CH₃CN (10 mL) was added CuI (20 mg, 0.10 mmol), TEA (1.4 mL), Pd(PPh₃)₂Cl₂ (73 mg, 0.10 mmol), ethynyl (trimethyl)silane (304 mg, 3.10 mmol). The mixture was heated under N₂ at 50° C. for 20 h. Removal of solvent gave a residue which was purified by column chromatography (PE/EA=10/1) to obtain the title compound (350 mg, 65.3%). m/z calcd for [C8H10BrNSSi] [M]: 258.9; found: 260.0 [M+H].

5-Bromo-6-trifluoromethyl-pyridine-3-yl 2,4,6-tri-O-acetyl-3-[4-(4-bromothiazol-2-yl)-1H-1,2,3-triazol-1-yl]-3-deoxy-1-thio-α-D-galactopyranoside

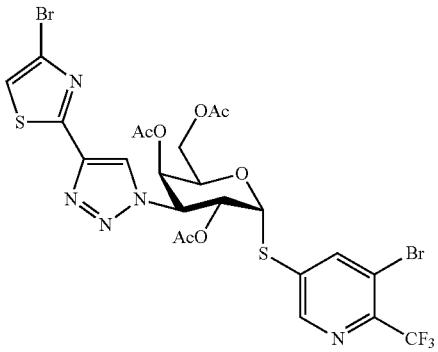

To a solution of 5-Bromo-6-trifluoromethyl-pyridine-3-yl 2,4,6-tri-O-acetyl-3-azido-3-deoxy-1-thio-α-D-galactopyranoside (38.0 mg, 0.0665 mmol) in CH₃CN (5 mL) was added 2-(4-bromothiazol-2-yl)ethynyl-trimethyl-silane (26.0 mg, 0.0998 mmol), DIPEA (0.0569 mL) 0.333 mmol), Copper(I)Iodide (12.7 mg, 0.0665 mmol) and CsF (10.1 mg, 0.0665 mmol). The mixture was heated under a N₂ atmosphere at reflux overnight. Removal of solvent gave a residue which was purified by column chromatography to obtain the title compound 22.0 mg (43.6%) as a white solid. m/z calcd for $[C_{23}H_{20}Br_2F_3N_5O_7S_2]^+$ $[M+H]^+$: 758.0; found: 758.0.

Intermediate 3

5-Chloro-6-cyano-pyridine-3-yl 2,4,6-tri-O-acetyl-3-[4-(4-chlorothiazol-2-yl)-1H-1,2,3-triazol-1-yl]-3-deoxy-1-thio-α-D-galactopyranoside and Intermediate 4

5-Bromo-2-cyano-pyridine-3-yl 2,4,6-tri-O-acetyl-3-[4-(4-chlorothiazol-2-yl)-1H-1,2,3-triazol-1-yl]-3-deoxy-1-thio-α-D-galactopyranoside Acetyl 2,4,6-tri-O-acetyl-3-azido-3-deoxy-1-thio-α-D-galactopyranoside

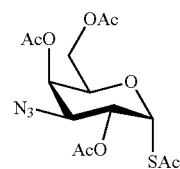

To a solution of 2,4,6-tri-O-acetyl-3-azido-3-deoxy-β-D-galactopyranosyl chloride (3.49 g, 10.0 mmol) in DMF (40 mL), potassium thioacetate (2.28 g, 20.0 mmol) and 4 Å molecular sieves (3.5 g) were added. The reaction was stirred at rt overnight followed by followed by removal of solvents in vacuum. The residue was purified by column chromatography to obtain the title compound (2.2 g 57%)¹H NMR (400 MHz, CDCl₃) δ 6.18 (d, J=5.3 Hz, 1H), 5.36 (d, J=3.1 Hz, 1H), 5.33 (dd, J=11.0, 5.3 Hz, 1H), 4.08-4.00 (m, 2H), 3.98-3.92 (m, 1H), 3.64 (dd, J=10.9, 3.3 Hz, 1H), 2.36 (s, 3H), 2.10 (s, 3H), 2.02 (s, 3H), 1.97 (s, 3H). m/z calcd for $[C_{14}H_{19}N_3O_8S]$ $[M+H]^+$: 390.1; found: 390.1.

5-Chloro-6-cyano-pyridine-3-yl 2,4,6-tri-O-acetyl-3-azido-3-deoxy-1-thio-α-D-galactopyranoside and 5-Bromo-2-cyano-pyridine-3-yl 2,4,6-tri-O-acetyl-3-azido-3-deoxy-1-thio-α-D-galactopyranoside

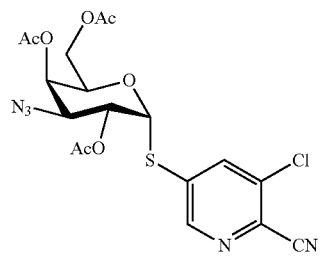

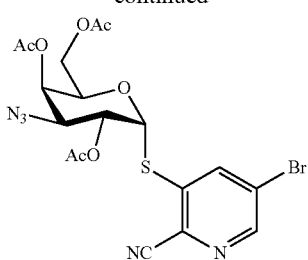

To a solution of acetyl 2,4,6-tri-O-acetyl-3-azido-3-deoxy-1-thio-α-D-galactopyranoside (900 mg, 2.31 mmol) in DMF (10 mL) was added 2-cyano-3-bromo-5-chloro-pyridine (1379 mg, 4.62 mmol) and diethylamine (502 mg, 2.31 mmol). The mixture was stirred under a $N_2$ atmosphere at rt overnight. The solvents were removed and the residue was purified by column chromatography to obtain the title mixture of products (450 mg).

5-Chloro-6-cyano-pyridine-3-yl 2,4,6-tri-O-acetyl-3-azido-3-deoxy-1-thio-α-D-galactopyranoside m/z calcd for $[C_{18}H_{18}ClN_5O_7S]^+$ $[M+H]^+$: 484.1; found: 484.1.

5-Bromo-2-cyano-pyridine-3-yl 2,4,6-tri-O-acetyl-3-azido-3-deoxy-1-thio-α-D-galactopyranoside m/z calcd for $[C_{18}H_{18}BrN_5O_7S]^+$ $[M+H]^+$: 529.0; found: 529.0.

Intermediate 3

5-Chloro-6-cyano-pyridine-3-yl 2,4,6-tri-O-acetyl-3-[4-(4-chlorothiazol-2-yl)-1H-1,2,3-triazol-1-yl]-3-deoxy-1-thio-α-D-galactopyranoside and

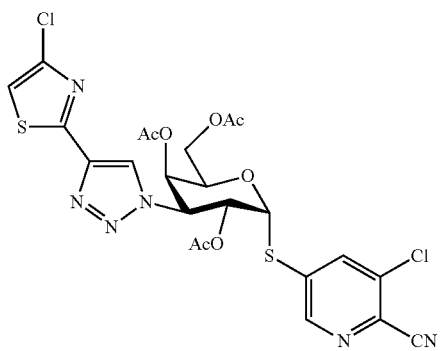

Intermediate 4

5-Bromo-2-cyano-pyridine-3-yl 2,4,6-tri-O-acetyl-3-[4-(4-chlorothiazol-2-yl)-1H-1,2,3-triazol-1-yl]-3-deoxy-1-thio-α-D-galactopyranoside

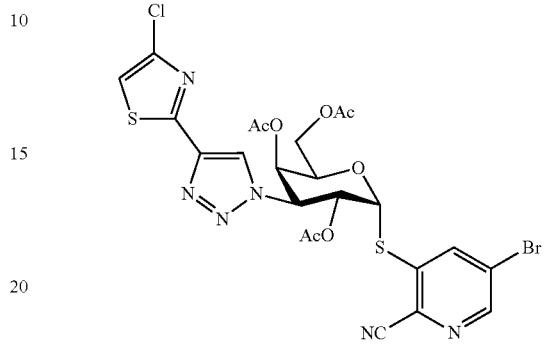

To a mixture of 5-chloro-6-cyano-pyridine-3-yl 2,4,6-tri-O-acetyl-3-azido-3-deoxy-1-thio-α-D-galactopyranoside and 5-bromo-2-cyano-pyridine-3-yl 2,4,6-tri-O-acetyl-3-azido-3-deoxy-1-thio-α-D-galactopyranoside (107 mg, 0.203 mmol) in acetonitrile (5 mL) was added 2-(4-chlorothiazol-2-yl)ethynyl-trimethyl-silane (65 mg, 0.304 mmol). Triethylamine (102 mg, 1.01 mmol), copper(I) iodide (11.6 mg, 0.061 mmol) and CsF (46.3 mg, 0.305 mmol) were added. The reaction was stirred at room temperature overnight. The mixture was concentrated in vacuum and the residue was purified by column chromatography (PE/EA=5/1) to obtain Intermediate 3

5-Chloro-6-cyano-pyridine-3-yl 2,4,6-tri-O-acetyl-3-[4-(4-chlorothiazol-2-yl)-1H-1,2,3-triazol-1-yl]-3-deoxy-1-thio-α-D-galactopyranoside, 110 mg m/z calcd for $[C_{23}H_{20}Cl_2N_6O_7S_2]^+$ $[M+H]^+$: 627.5; found: 628.

and

Intermediate 4

5-Bromo-2-cyano-pyridine-3-yl 2,4,6-tri-O-acetyl-3-[4-(4-chlorothiazol-2-yl)-1H-1,2,3-triazol-1-yl]-3-deoxy-1-thio-α-D-galactopyranoside, 40 mg m/z calcd for $[C_{23}H_{20}BrClN_6O_7S_2]^+$ $[M+H]^+$: 671.9; found: 672.

Intermediate 5

5-Chloro-2-cyano-pyridine-3-yl 2,4,6-tri-O-acetyl-3-[4-(4-chlorothiazol-2-yl)-1H-1,2,3-triazol-1-yl]-3-deoxy-1-thio-α-D-galactopyranoside and

Intermediate 6

5-Bromo-6-cyano-3-pyridyl 2,4,6-tri-O-acetyl-3-[4-(4-chlorothiazol-2-yl)-1H-1,2,3-triazol-1-yl]-3-deoxy-1-thio-α-D-galactopyranoside 4-chloro-2-((trimethylsilyl)ethynyl)thiazole

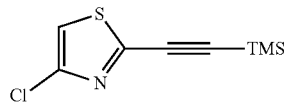

To a solution of 2-bromo-4-chlorothiazole (500 mg, 2.52 mmol) in THF (10 mL) were added copper(I) iodide (24 mg, 0.13 mmol), TEA (1.76 mL) 12.6 mmol), [(C$_6$H$_5$)$_3$P]$_2$PdCl$_2$ (88.4 mg, 0.126 mol), ethynyl(trimethyl)silane (0.495 g, 5.04 mmol). The mixture was stirred under N$_2$ atmosphere for 3 h. Removal of solvent gave a residue which was purified by column chromatography (PE/EA=10/1) to obtain 110 mg (20%) of the title compound. m/z calcd for [C$_8$H$_{11}$ClNSSi]$^+$ [M+H]$^+$: 216.01; found: 216.0.

5-Chloro-2-cyano-pyridine-3-yl 2,4,6-tri-O-acetyl-3-azido-3-deoxy-1-thio-α-D-galactopyranoside and 5-Bromo-6-cyano-3-pyridyl 2,4,6-tri-O-acetyl-3-azido-3-deoxy-1-thio-α-D-galactopyranoside

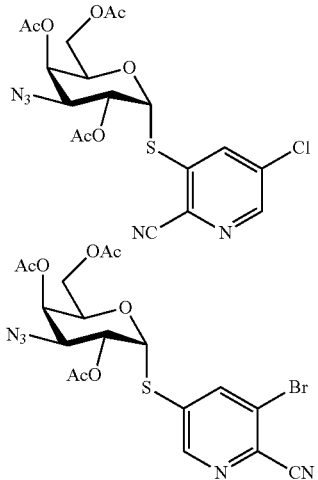

Acetyl 2,4,6-tri-O-acetyl-3-azido-3-deoxy-1-thio-α-D-galactopyranoside (784 mg, 2.01 mmol) and 3-bromo-5-chloro-pyridine-2-carbonitrile (876 mg, 4.03 mmol) were dissolved in DMF (30 mL). Diethylamine (295 mg, 4.03 mmol) was added. The reaction was stirred at room temperature for 20 h. Water (50 mL) and DCM (50 mL) were added. The phases were separated and the aqueous phase was extracted with DCM (50 mL×2), the combined organic phases were washed with water (100 mL) and brine (100 mL), dried over anhydrous sodium sulphate. Removal of solvent gave a residue which was purified by column chromatography (PE/EA=3/1) to obtain the title compound mixture 265 mg (25%).

5-Chloro-2-cyano-pyridine-3-yl 2,4,6-tri-O-acetyl-3-azido-3-deoxy-1-thio-α-D-galactopyranoside m/z calcd for [C$_{18}$H$_{19}$ClN$_5$O$_7$S]$^+$ [M+H]$^+$: 484.07; found: 484.1.

5-Bromo-6-cyano-3-pyridyl 2,4,6-tri-O-acetyl-3-azido-3-deoxy-1-thio-α-D-galactopyranoside m/z calcd for [C$_{18}$H$_{19}$BrN$_5$O$_7$S]$^+$ [M+H]$^+$: 528.02; found: 528.0.

Intermediate 5

5-Chloro-2-cyano-pyridine-3-yl 2,4,6-tri-O-acetyl-3-[4-(4-chlorothiazol-2-yl)-1H-1,2,3-triazol-1-yl]-3-deoxy-1-thio-α-D-galactopyranoside and

Intermediate 6

5-Bromo-6-cyano-3-pyridyl 2,4,6-tri-O-acetyl-3-[4-(4-chlorothiazol-2-yl)-1H-1,2,3-triazol-1-yl]-3-deoxy-1-thio-α-D-galactopyranoside

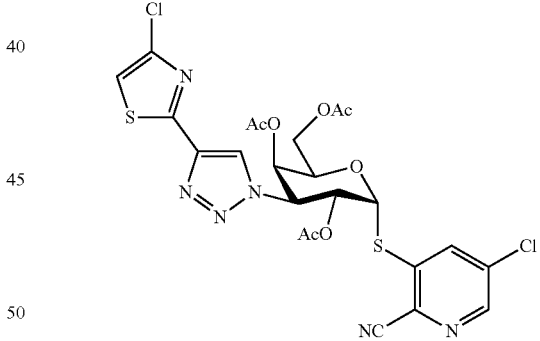

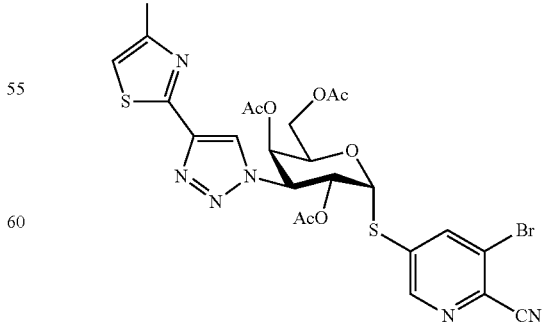

To a mixture of 5-bromo-6-cyano-3-pyridyl 2,4,6-tri-O-acetyl-3-azido-3-deoxy-1-thio-α-D-galactopyranoside and 5-chloro-2-cyano-pyridine-3-yl 2,4,6-tri-O-acetyl-3-azido-3-deoxy-1-thio-α-D-galactopyranoside (100 mg, 0.189 mmol) in DCM (5 mL) were added TEA (0.132 mL, 0.946 mmol), copper(I) iodide (10.8 mg, 0.0568 mmol), CsF (43.1 mg, 0.284 mmol), 2-(4-chlorothiazol-2-yl)ethynyl-trimethyl-silane (61.3 mg, 0.284 mmol). The reaction was stirred at room temperature for 4 h under a N₂ atmosphere. Water (10 mL) and DCM (10 mL) were added. The phases were separated and the aqueous phase was extracted with DCM (10 mL×2), the combined organic phases were washed with water (20 mL) and brine (20 mL), dried over anhydrous sodium sulphate. Removal of solvent gave a residue which was purified by column chromatography (PE/EA=4/1) to obtain

Intermediate 5

5-Chloro-2-cyano-pyridine-3-yl 2,4,6-tri-O-acetyl-3-[4-(4-chlorothiazol-2-yl)-1H-1,2,3-triazol-1-yl]-3-deoxy-1-thio-α-D-galactopyranoside 46.0 mg (38.7%)

¹H NMR (400 MHz, CDCl₃) δ 8.53 (d, J=2.2 Hz, 1H), 8.09 (s, 1H), 8.00 (d, J=2.2 Hz, 1H), 7.07 (s, 1H), 6.22 (d, J=5.6 Hz, 1H), 5.98 (dd, J=11.7, 5.6 Hz, 1H), 5.58 (d, J=2.3 Hz, 1H), 5.18 (dd, J=11.8, 3.0 Hz, 1H), 4.83-4.67 (m, 1H), 4.11 (dd, J=11.8, 4.9 Hz, 1H), 4.02 (td, J=11.6, 7.3 Hz, 1H), 2.02 (s, 3H), 1.96 (s, 3H), 1.95 (s, 3H). m/z calcd for $[C_{23}H_{21}Cl_2N_6O_7S_2]^+$ [M+H]⁺: 627.03; found: 627.0.

Intermediate 6

5-Bromo-6-cyano-3-pyridyl 2,4,6-tri-O-acetyl-3-[4-(4-chlorothiazol-2-yl)-1H-1,2,3-triazol-1-yl]-3-deoxy-1-thio-α-D-galactopyranoside 57.0 mg (45%)

¹H NMR (400 MHz, CDCl₃) δ 8.60 (d, J=1.9 Hz, 1H), 8.12-8.01 (m, 2H), 7.08 (s, 1H), 6.28 (d, J=5.6 Hz, 1H), 5.97 (dd, J=11.7, 5.6 Hz, 1H), 5.56 (d, J=2.5 Hz, 1H), 5.18 (dd, J=11.7, 3.0 Hz, 1H), 4.72-4.57 (m, 1H), 4.10 (dd, J=11.8, 4.7 Hz, 1H), 4.02 (td, J=11.6, 7.4 Hz, 1H), 2.04 (s, 3H), 1.93 (s, 3H), 1.91 (s, 3H). m/z calcd for $[C_{23}H_{21}BrClN_6O_7S_2]^+$ [M+H]⁺: 670.98; found: 671.0.

Intermediate 7

3,4-Dichlorophenyl 2,4,6-tri-O-acetyl-3-deoxy-3-[4-(2-hydroxythiazol-4-yl)-1H-1,2,3-triazol-1-yl]-1-thio-α-D-galactopyranoside 4-bromo-2-[(4-methoxyphenyl)methoxy]thiazole

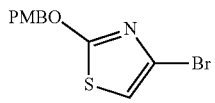

To a solution of (4-methoxyphenyl)methanol (313 mg, 2.26 mmol) in THF (5 mL) was added NaH (59.3 mg, 2.47 mmol). The mixture was stirred at room temperature for 0.5h. Then 2,4-dibromothiazole (500 mg, 2.06 mmol) was added. The reaction was stirred at room temperature over night. Removal of solvent gave a residue which was purified by column chromatography (PE/EA=10/1) to obtain 500 mg (80.9%) of the title compound. ¹H NMR (400 MHz, CDCl₃) δ 7.31 (d, J=8.6 Hz, 2H), 6.85 (d, J=8.7 Hz, 2H), 6.51 (s, 1H), 5.30 (s, 2H), 3.75 (s, 3H). m/z calculated for $[C_3H_2BrNOS][M-PMB+H=]+$: 180.0; found: 180.1.

2-[2-[(4-methoxyphenyl)methoxy]thiazol-4-yl]ethynyl-trimethyl-silane

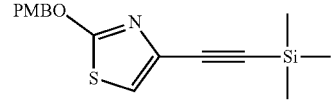

To a solution of 4-bromo-2-[(4-methoxyphenyl)methoxy]thiazole (500 mg, 1.67 mmol) in DMF (5 mL) was added Copper(I)Iodide (15.9 mg, 0.0833 mmol), TEA (1.16 mL) 8.33 mmol), Pd(PPh₃)₂Cl₂ (58.5 mg, 0.0833 mmol), ethynyl (trimethyl)silane (469 mg, 4.77 mmol). The mixture was heated under N₂ at 50° C. for 20 h. Removal of solvent gave a residue which was purified by column chromatography (PE/EA=10/1) to obtain the title compound 60.0 mg (11.3%).

¹H NMR (400 MHz, CDCl₃) δ 7.31 (dd, J=8.9, 2.5 Hz, 2H), 6.88-6.81 (m, 3H), 5.33 (s, 2H), 3.75 (s, 3H), 0.18 (s, 9H). m/z calcd for $[C_{16}H_{19}NO_2SSi]+$ [M-PMB+H]+: 198.0; found: 198.1.

3,4-Dichlorophenyl 2,4,6-tri-O-acetyl-3-deoxy-3-[4-(2-((4-methoxybenzyl)oxy)thiazol-4-yl)-1H-1,2,3-triazol-1-yl]-1-thio-α-D-galactopyranoside

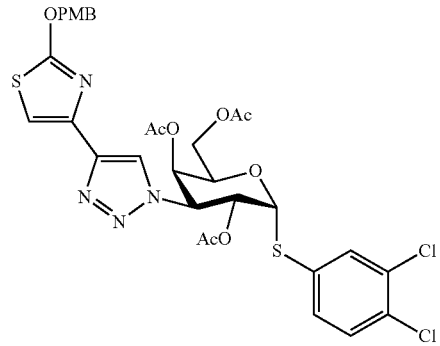

To a solution of 3,4-dichlorophenyl 2,4,6-tri-O-acetyl-3-azido-3-deoxy-1-thio-α-D-galactopyranoside (60.0 mg, 0.122 mmol) (Prepared in according to WO2016/120403) in CH₃CN (5 mL) were added TEA (0.0849 mL) 0.609 mmol), copper(I) iodide (6.96 mg, 0.0366 mmol), CsF (27.8 mg, 0.183 mmol), 2-[2-[(4-methoxyphenyl)methoxy]thiazol-4-yl]ethynyl-trimethyl-silane (58.0 mg, 0.183 mmol). The reaction was stirred at room temperature for 20 h under a N₂ atmosphere. Water (10 mL) and DCM (10 mL) were added. The phases were separated and the aqueous phase was extracted with DCM (5 mL×2), the combined organic phases were washed with water (20 mL) and brine (20 mL), dried over anhydrous sodium sulphate. Removal of solvent gave a residue which was purified by column chromatography (PE/EA=2/1) to obtain the product 55.0 mg (61.2%).

m/z calcd for $[C_{31}H_{30}Cl_2N_4O_9S_2]^+$ [M+H]⁺: 737.1; found: 737.1.

3,4-Dichlorophenyl 2,4,6-tri-O-acetyl-3-deoxy-3-[4-(2-hydroxythiazol-4-yl)-1H-1,2,3-triazol-1-yl]-1-thio-α-D-galactopyranoside

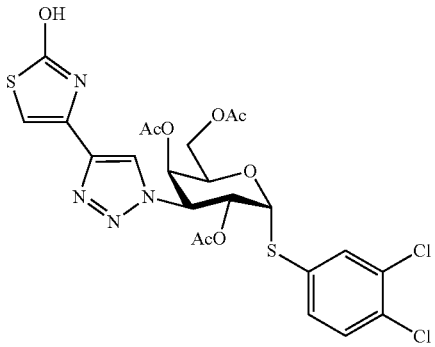

To a solution of 3,4-Dichlorophenyl 2,4,6-tri-O-acetyl-3-deoxy-3-[4-(2-((4-methoxybenzyl)oxy)thiazol-4-yl)-1H-1,2,3-triazol-1-yl]-1-thio-α-D-galactopyranoside (55.0 mg, 0.0746 mmol) in DCM (5 mL) was added TFA (0.0277 mL) 0.373 mmol). The reaction was stirred at room temperature for 4 h. The mixture was evaporated to dryness and the crude product was purified by column chromatography (PE/EA=2/1) to obtain the title compound (30.0 mg, 0.0356 mmol, yield: 47.8%). m/z calcd for $[C_{23}H_{22}C_2N_4O_8S_2]^+$ $[M+H]^+$: 617.0; found: 617.0.

3,4-Dichlorophenyl 2,4,6-tri-O-acetyl 3-[4-(2-chlorothiazol-4-yl)-1H-1,2,3-triazol-1-yl]-3-deoxy-1-thio-α-D-galactopyranoside

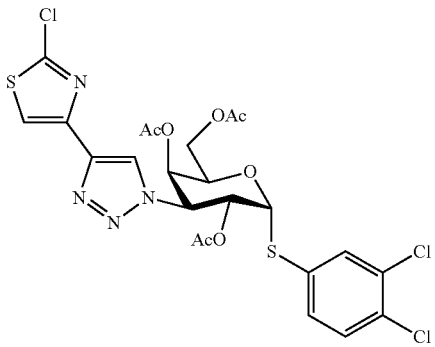

3,4-Dichlorophenyl 2,4,6-tri-O-acetyl-3-deoxy-3-[4-(2-hydroxythiazol-4-yl)-1H-1,2,3-triazol-1-yl]-1-thio-α-D-galactopyranoside (60.0 mg, 0.0972 mmol) was dissolved in $POCl_3$ (2 mL) and the reaction was heated to 100° C. overnight. The reaction was cooled to room temperature and poured into saturated $NaHCO_3$ (aq). The aqueous phase was extracted with DCM (5 mL×2) and the combined organic phases were washed with water (20 mL) and brine (20 mL), dried over anhydrous sodium sulphate. Removal of solvent gave a residue which was purified by column chromatography (PE/EA=2/1) to obtain 10.0 mg (16.2%) of the title compound. m/z calcd for $[C_{23}H_{21}Cl_3N_4O_7S_2]^+$ $[M+H]^+$: 635.0; found: 635.0.

Intermediate 11

3,4-Dichlorophenyl 2,4,6-tri-O-acetyl-3-deoxy-3-[4-(4-carbamoyl)-1H-1,2,3-triazol-1-yl]-1-thio-α-D-galactopyranoside

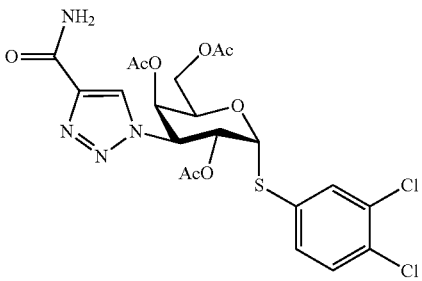

To a solution of 3,4-dichlorophenyl 2,4,6-tri-O-acetyl-3-azido-3-deoxy-1-thio-α-D-galactopyranoside (4.00 g, 8.12 mmol)(Prepared in according to WO2016/120403) in $CH_3CN$ (20 mL) were added TEA (5.66 mL) 40.6 mmol), copper(I) iodide (77.4 mg, 0.406 mmol), prop-2-ynamide (842 mg, 12.2 mmol). The reaction was stirred at room temperature for 20 h under a $N_2$ atmosphere. Water (10 mL) and DCM (10 mL) were added. The phases were separated and the aqueous phase was extracted with DCM (5 mL*2), the combined organic phases were washed with water (20 mL) and brine (20 mL), dried over anhydrous sodium sulphate. Removal of solvent gave a residue which was purified by column chromatography (PE/EA=2/1) to give 1.20 g (26.3%) of the title compound. $^1H$ NMR (400 MHz, $CDCl_3$) δ 8.12 (s, 1H), 7.61 (d, J=2.0 Hz, 1H), 7.42 (d, J=8.4 Hz, 1H), 7.32 (dd, J=8.4, 2.0 Hz, 1H), 7.00 (s, 1H), 6.14 (d, J=5.5 Hz, 1H), 5.93 (dd, J=11.7, 5.5 Hz, 1H), 5.65 (s, 1H), 5.59 (d, J=2.4 Hz, 1H), 5.26 (dd, J=11.7, 2.9 Hz, 1H), 4.82 (t, J=6.2 Hz, 1H), 4.19-4.00 (m, 1H), 2.07 (s, 3H), 2.00 (s, 3H), 1.98 (s, 3H). m/z calcd for $[C_2H_{22}Cl_2N_4O_8S]^+$ $[M+H]^+$: 561.1; found: 561.2.

3,4-Dichlorophenyl 2,4,6-tri-O-acetyl-3-deoxy-3-[4-(4-carbamothioyl)-1H-1,2,3-triazol-1-yl]-1-thio-α-D-galactopyranoside

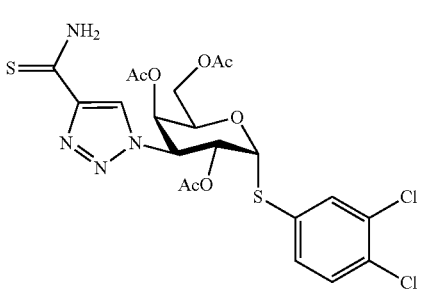

To a solution of 3,4-dichlorophenyl 2,4,6-tri-O-acetyl-3-deoxy-3-[4-(4-carbamoyl)-1H-1,2,3-triazol-1-yl]-1-thio-α-D-galactopyranoside (1.20 g, 2.1 mmol) in DCM (20 mL) was added Lawessons reagent (1.73 g, 4.3 mmol). The mixture was stirred at room temperature for 20 h. Removal of solvent gave a residue which was purified by column chromatography (PE/EA=2/1) to obtain the title compound (650 mg, 1.13 mmol, yield: 52.7%). m/z calcd for [C$_{21}$H$_{22}$C$_{12}$N$_4$O$_7$S$_2$]$^+$ [M+H]$^+$: 577.0; found: 577.0.

3,4-Dichlorophenyl 2,4,6-tri-O-acetyl-3-deoxy-3-[4-(4-hydroxythiazol-2-yl)-1H-1,2,3-triazol-1-yl]-1-thio-α-D-galactopyranoside

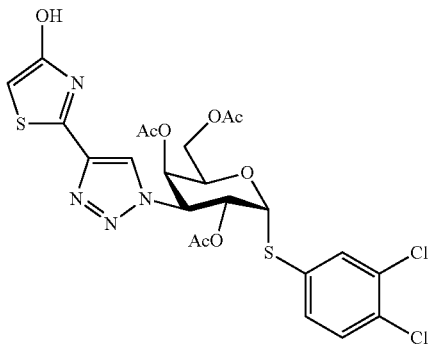

To a solution of 3,4-dichlorophenyl 2,4,6-tri-O-acetyl-3-deoxy-3-[4-(4-carbamothioyl)-1H-1,2,3-triazol-1-yl]-1-thio-α-D-galactopyranoside (100 mg, 0.173 mmol) in DCM (5 mL) were added NaHCO$_3$ (145 mg, 1.73 mmol), 2-chloroacetyl chloride (156 mg, 1.39 mmol). The reaction was stirred at room temperature with for 20 h under a N$_2$ atmosphere. Water (10 mL) and DCM (10 mL) were added. The phases were separated and the aqueous phase was extracted with DCM (5 mL*2), the combined organic phases were washed with water (20 mL) and brine (20 mL), dried over anhydrous sodium sulphate. Removal of solvent gave a residue which was purified by column chromatography (PE/EA=2/1) to the title compound (60.0 mg, 0.0972 mmol, yield: 56.1%) m/z calcd for [C$_{23}$H$_{22}$C$_{12}$N$_4$O$_8$S$_2$]$^+$ [M+H]$^+$: 617.0; found: 617.0.

Intermediate 12

See Intermediate 7

Intermediate 13

5-Chloro-6-cyano-pyridine-3-yl 2,4,6-tri-O-acetyl3-deoxy-3-[4-(2-hydroxythiazol-4-yl)-1H-1,2,3-triazol-1-yl]-1-thio-α-D-galactopyranoside and Intermediate 14

5-Bromo-2-cyano-pyridine-3-yl 2,4,6-tri-O-acetyl-3-deoxy-3-[4-(2-hydroxythiazol-4-yl)-1H-1,2,3-triazol-1-yl]-1-thio-α-D-galactopyranoside 4-bromo-2-[(4-methoxyphenyl)methoxy]thiazole

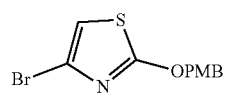

To a solution of (4-methoxyphenyl)methanol (6.256 g, 45.3 mmol) in THF (100 mL) was added NaH (1.087 g, 45.3 mmol). The mixture was stirred at room temperature for 0.5h. Then 2,4-dibromothiazole (10.0 g, 41.2 mmol) was added in. The reaction was stirred at room temperature overnight. Removal of solvent gave a residue which was purified by column chromatography (PE/EA=10/1) to obtain the title compound. (7.00 g, 23.3 mmol, yield: 56.6%). $^1$H NMR (400 MHz, CDCl$_3$) δ 7.31 (d, J=8.6 Hz, 2H), 6.85 (d, J=8.7 Hz, 2H), 6.51 (s, 1H), 5.30 (s, 2H), 3.75 (s, 3H). m/z calcd for C$_{11}$H$_{10}$BrNO$_2$S: 300.1; found: 300.1.

2-[2-[(4-methoxyphenyl)methoxy]thiazol-4-yl]ethynyl-trimethyl-silane

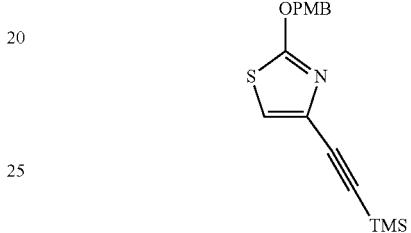

To a solution of 4-bromo-2-[(4-methoxyphenyl)methoxy]thiazole (7.00 g, 23.3 mmol) in DMF (70 mL) was added Copper(I)Iodide (222 mg, 1.17 mmol), TEA (16.3 mL, 117 mmol), Pd(PPh$_3$)$_2$Cl$_2$ (819 mg, 1.17 mmol), ethynyl(trimethyl)silane (3.4 g, 35.0 mmol). The mixture was heated under N$_2$ atmosphere at 50° C. for 20 h. Removal of solvent gave a residue which was purified by column chromatography (PE/EA=10/1) to afford th title compound (2.5 g, 7.9 mmol, yield: 34%)$^1$H NMR (400 MHz, CDCl$_3$) δ 7.30 (d, J=8.7 Hz, 2H), 6.89-6.80 (m, 3H), 5.33 (s, 2H), 3.75 (s, 3H), 0.18 (s, 9H). m/z calcd for [C$_6$H$_{19}$NO$_2$SSi]: 317; found: 317.

4-(2-trimethylsilylethynyl)thiazol-2-ol

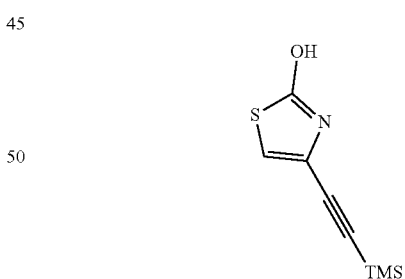

To a solution of 2-[2-[(4-methoxyphenyl)methoxy]thiazol-4-yl]ethynyl-trimethyl-silane (2.50 g, 7.87 mmol) in TFA/DCM (20 mL, v/v=1/20) was stirred at room temperature for 4h. Then the pH was adjusted to adjust pH 7-8 by addition of NaHCO$_3$ aq. to. The phases were separated and the organic layer was dried and concentrated to dryness. The crude product was purified by column chromatography to obtain the title compound (1.2 g, 6.08 mmol, yield: 77.2%). $^1$H NMR (400 MHz, CDCl$_3$) δ 8.09 (s, 1H), 6.30 (s, 1H), 0.17 (s, 9H). m/z calcd for [C$_8$H$_{11}$NOSSi]$^+$ [M+H]$^+$: 197.3; found: 197.

5-Chloro-6-cyano-pyridine-3-yl 2,4,6-tri-O-acetyl-3-azido-3-deoxy-1-thio-α-D-galactopyranoside and 5-Bromo-2-cyano-pyridine-3-yl 2,4,6-tri-O-acetyl-3-azido-3-deoxy-1-thio-α-D-galactopyranoside

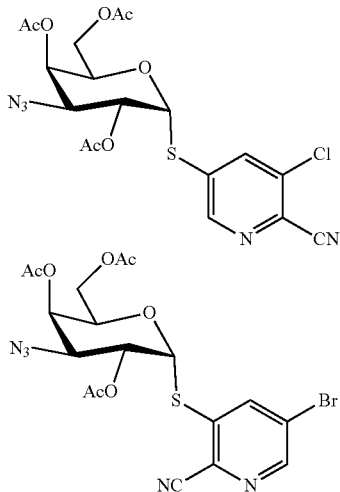

To a solution of acetyl 2,4,6-tri-O-acetyl-3-azido-3-deoxy-1-thio-α-D-galactopyranoside (900 mg, 2.31 mmol) in DMF (10 mL) was added 2-cyano-5-bromo-3-chloro-pyridine (1379 mg, 4.62 mmol) and diethylamine (502 mg, 2.31 mmol). The mixture was stirred under $N_2$ at rt overnight. Removal of solvent gave a residue which was purified by column chromatography to obtain the title mixture of products (450 mg).

5-Chloro-6-cyano-pyridine-3-yl 2,4,6-tri-O-acetyl-3-azido-3-deoxy-1-thio-α-D-galactopyranoside m/z calcd for $[C18H18ClN5O7S]^+$ $[M+H]^+$: 484.1; found: 484.1.

5-Bromo-2-cyano-pyridine-3-yl 2,4,6-tri-O-acetyl-3-azido-3-deoxy-1-thio-α-D-galactopyranoside m/z calcd for $[C18H18BrN5O7S]^+$ $[M+H]^+$: 529.0; found: 529.0.

5-Chloro-6-cyano-pyridine-3-yl 2,4,6-tri-O-acetyl3-deoxy-3-[4-(2-hydroxythiazol-4-yl)-1H-1,2,3-triazol-1-yl]-1-thio-α-D-galactopyranoside and

5-Bromo-2-cyano-pyridine-3-yl 2,4,6-tri-O-acetyl-3-deoxy-3-[4-(2-hydroxythiazol-4-yl)-1H-1,2,3-triazol-1-yl]-1-thio-α-D-galactopyranoside

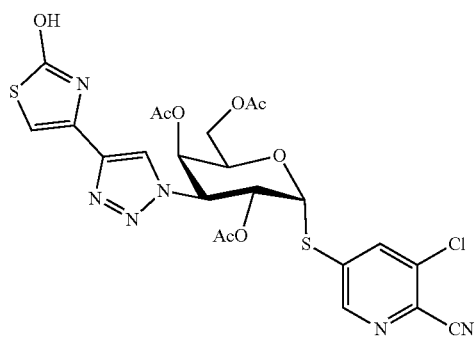

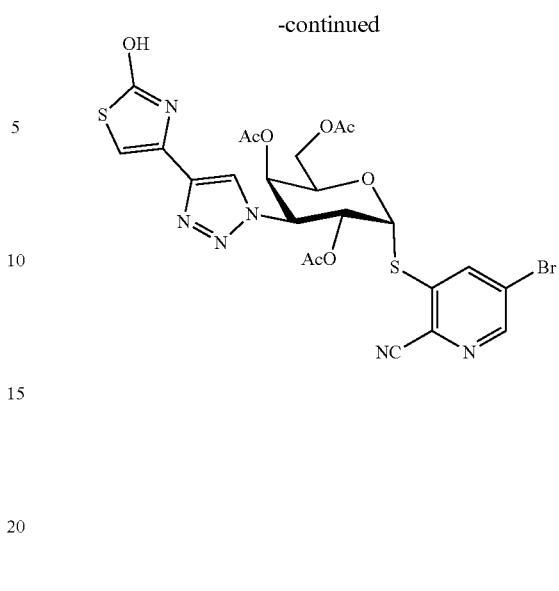

To a solution of 5-chloro-6-cyano-pyridine-3-yl 2,4,6-tri-O-acetyl-3-azido-3-deoxy-1-thio-α-D-galactopyranoside and 5-bromo-2-cyano-pyridine-3-yl 2,4,6-tri-O-acetyl-3-azido-3-deoxy-1-thio-α-D-galactopyranoside in acetonitrile (5 mL) and 4-(2-trimethylsilylethynyl)thiazol-2-ol (112 mg, 0.568 mmol) was dissolved in acetonitrile (5 ml). Triethylamine (102 mg, 1.01 mmol), Copper(I)Iodide (21.6 mg, 0.114 mmol) and CsF (46.3 mg, 0.305 mmol) was added. The reaction was stirred at room temperature overnight. The reaction mixture was concentrated in vacuum and the residue was purified by column chromatography to obtain the two title compounds:

5-Chloro-6-cyano-pyridine-3-yl 2,4,6-tri-O-acetyl3-deoxy-3-[4-(2-hydroxythiazol-4-yl)-1H-1,2,3-triazol-1-yl]-1-thio-α-D-galactopyranoside, 60.0 mg (26.0%)

$^1$H NMR (400 MHz, CDCl$_3$) δ 11.26 (s, 1H), 8.57 (d, J=1.9 Hz, 1H), 7.97-7.90 (m, 2H), 6.66 (s, 1H), 6.29 (d, J=5.5 Hz, 1H), 6.03 (dd, J=11.7, 5.6 Hz, 1H), 5.57 (d, J=2.4 Hz, 1H), 5.20 (dd, J=11.7, 2.9 Hz, 1H), 4.69 (dd, J=7.5, 4.9 Hz, 1H), 4.21-3.96 (m, 2H), 2.05 (s, 3H), 1.93 (d, J=6.3 Hz, 6H). m/z calcd for $[C_{23}H_{21}ClN_6O_8S_2]^+[M+H_2O]^+$:609; found: 627.

5-Bromo-2-cyano-pyridine-3-yl 2,4,6-tri-O-acetyl-3-deoxy-3-[4-(2-hydroxythiazol-4-yl)-1H-1,2,3-triazol-1-yl]-1-thio-α-D-galactopyranoside, 25 mg (10%)

$^1$H NMR (400 MHz, CDCl$_3$) δ 10.48 (s, 1H), 8.63 (d, J=1.8 Hz, 1H), 8.15 (d, J=1.9 Hz, 1H), 7.89 (s, 1H), 6.54 (s, 1H), 6.23 (d, J=5.5 Hz, 1H), 6.05 (dd, J=11.6, 5.5 Hz, 1H), 5.58 (s, 1H), 5.16 (dd, J=11.7, 2.7 Hz, 1H), 4.84-4.70 (m, 1H), 4.14-4.03 (m, 2H), 2.02 (s, 3H), 1.96 (d, J=3.3 Hz, 6H). m/z calcd for $[C_{23}H_{21}BrN_6O_8S_2]^+[M+H_2O]^+$:653; found: 671.

Intermediate 15

5-Bromo-6-cyano-3-pyridyl 2,4,6-tri-O-acetyl 3-deoxy-3-[4-(2-hydroxythiazol-4-yl)-1H-1,2,3-triazol-1-yl]-1-thio-α-D-galactopyranoside and

Intermediate 16

5-Chloro-2-cyano-3-pyridyl 2,4,6-tri-O-acetyl-3-deoxy-3-[4-(2-hydroxythiazol-4-yl)-1H-1,2,3-triazol-1-yl]-1-thio-α-D-galactopyranoside 5-Bromo-6-cyano-3-pyridyl 2,4,6-tri-O-acetyl-3-azido-3-deoxy-1-thio-α-D-galactopyranoside and 5-Chloro-2-cyano-3-pyridyl 2,4,6-tri-O-acetyl-3-azido-3-deoxy-1-thio-α-D-galactopyranoside

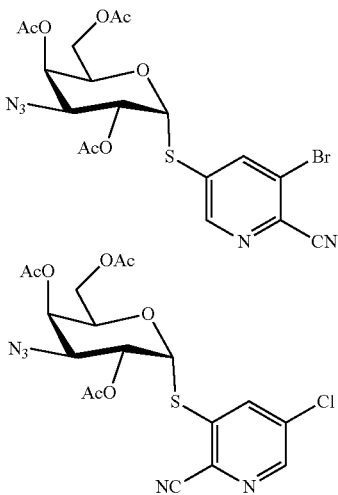

To a solution of acetyl 2,4,6-tri-O-acetyl-3-azido-3-deoxy-1-thio-α-D-galactopyranoside (900 mg, 2.31 mmol) in DMF (10 mL) was added 2-cyano-3-bromo-5-chloro-pyridine (1379 mg, 4.62 mmol) and diethylamine (502 mg, 2.31 mmol). The mixture was stirred under $N_2$ atmosphere at rt overnight. Removal of solvent to give a residue which was purified by column chromatography to obtain the title product mixture (450 mg)

5-Bromo-6-cyano-3-pyridyl 2,4,6-tri-O-acetyl-3-azido-3-deoxy-1-thio-α-D-galactopyranoside m/z calcd for $[C_{18}H_{18}BrN_5O_7S]^+$ $[M+H]^+$: 529.0; found: 529.0.

5-Chloro-2-cyano-3-pyridyl 2,4,6-tri-O-acetyl-3-azido-3-deoxy-1-thio-α-D-galactopyranoside m/z calcd for $[C_{18}H_{18}ClN_5O_7S]^+$ $[M+H]^+$: 484.1; found: 484.1.

5-Bromo-6-cyano-3-pyridyl 2,4,6-tri-O-acetyl 3-deoxy-3-[4-(2-hydroxythiazol-4-yl)-1H-1,2,3-triazol-1-yl]-1-thio-α-D-galactopyranoside and 5-Chloro-2-cyano-3-pyridyl 2,4,6-tri-O-acetyl-3-deoxy-3-[4-(2-hydroxythiazol-4-yl)-1H-1,2,3-triazol-1-yl]-1-thio-α-D-galactopyranoside

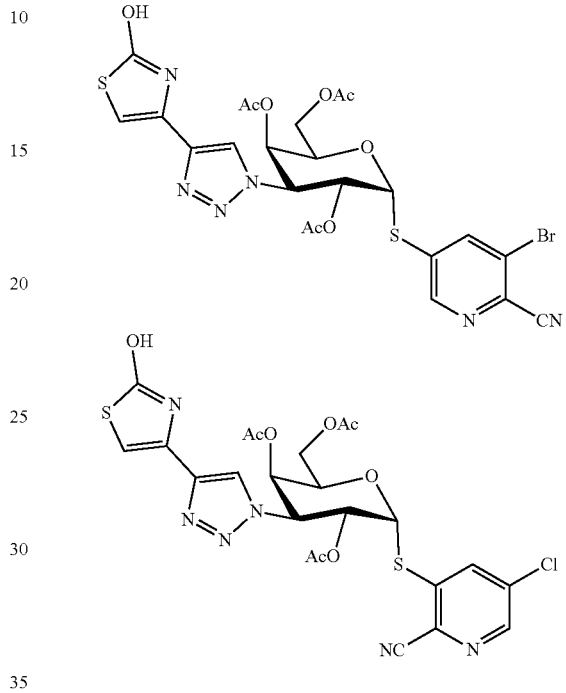

To a solution of the mixture of 5-bromo-6-cyano-3-pyridyl 2,4,6-tri-O-acetyl-3-azido-3-deoxy-1-thio-α-D-galactopyranoside and 5-chloro-2-cyano-3-pyridyl 2,4,6-tri-O-acetyl-3-azido-3-deoxy-1-thio-α-D-galactopyranoside (200 mg) in acetonitrile (5 mL) was added 4-(2-trimethylsilylethynyl)thiazol-2-ol (112 mg, 0.568 mmol) was dissolved in acetonitrile (5 ml) followed by triethylamine (102 mg, 1.01 mmol), Copper(I)Iodide (21.6 mg, 0.114 mmol) and CsF (46.3 mg, 0.305 mmol). The reaction was stirred at room temperature overnight. The mixture was concentrated in vacuum and the residue was purified by column chromatography (PE/EA=5/1) to obtain the two title compounds.

5-Bromo-6-cyano-3-pyridyl 2,4,6-tri-O-acetyl 3-deoxy-3-[4-(2-hydroxythiazol-4-yl)-1H-1,2,3-triazol-1-yl]-1-thio-α-D-galactopyranoside. 45 mg (17%)

$^1$H NMR (400 MHz, CDCl$_3$) δ 10.74 (s, 1H), 8.60 (d, J=1.9 Hz, 1H), 8.08 (d, J=1.9 Hz, 1H), 7.88 (s, 1H), 6.57 (s, 1H), 6.28 (d, J=5.5 Hz, 1H), 6.03 (dd, J=11.7, 5.5 Hz, 1H), 5.56 (d, J=2.5 Hz, 1H), 5.17 (dd, J=11.7, 3.0 Hz, 1H), 4.76-4.62 (m, 1H), 4.24-3.97 (m, 2H), 2.05 (s, 3H), 1.93 (d, J=8.2 Hz, 6H). m/z calcd for $[C_{23}H_{21}BrN_6O_8S_2]^+$ $[M+H_2O]^+$:653; found: 671.

5-Chloro-2-cyano-3-pyridyl 2,4,6-tri-O-acetyl-3-deoxy-3-[4-(2-hydroxythiazol-4-yl)-1H-1,2,3-triazol-1-yl]-1-thio-α-D-galactopyranoside, 45 mg (18%)

$^1$H NMR (400 MHz, CDCl$_3$) δ 10.71 (s, 1H), 8.53 (d, J=2.1 Hz, 1H), 8.01 (d, J=2.1 Hz, 1H), 7.90 (s, 1H), 6.57 (s, 1H), 6.24 (d, J=5.5 Hz, 1H), 6.05 (dd, J=11.6, 5.5 Hz, 1H), 5.59 (d, J=2.3 Hz, 1H), 5.17 (dd, J=11.7, 2.9 Hz, 1H), 4.86-4.71 (m, 1H), 4.25-3.92 (m, 2H), 2.03 (s, 3H), 1.97 (d, J=4.0 Hz, 6H).

m/z calcd for $[C_{23}H_{21}ClN_6O_8S_2]^+$ $[M+H_2O]^+$:609; found: 627.

Intermediate 17

5-Chloro-6-trifluoromethyl-pyridin-3-yl 2,4,6-tri-O-acetyl-3-deoxy-3-[4-(2-hydroxythiazol-4-yl)-1H-1,2,3-triazol-1-yl]-1-thio-α-D-galactopyranoside

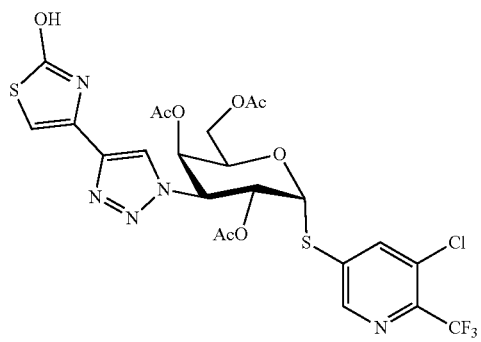

To a solution of 5-chloro-6-trifluoromethyl-pyridin-3-yl 2,4,6-tri-O-acetyl-3-azido-3-deoxy-1-thio-α-D-galactopyranoside (15.0 mg, 0.0285 mmol)(WO2016/120403) in $CH_3CN$ (2 mL) were added TEA (0.0198 mL, 0.142 mmol), copper (I) iodide (1.63 mg, 0.00854 mmol), CsF (6.49 mg, 0.0427 mmol), 4-(2-trimethylsilylethynyl)thiazol-2-ol (8.43 mg, 0.0427 mmol). The reaction was stirred at room temperature with stirring for 20 h under $N_2$ atmosphere. Water (10 mL) and DCM (10 mL) were added and the phases were separated. The aqueous phase was extracted with DCM (5 mL×2) and the combined organic phases were washed with water (20 mL) and brine (20 mL), dried over anhydrous sodium sulphate. Removal of solvent gave a residue which was purified by column chromatography (PE/EA=2/1) to obtain the title compound (12 mg, 0.0184 mmol, yield: 64.6%). $^1H$ NMR (400 MHz, $CDCl_3$) δ 11.14 (s, 1H), 8.55 (d, J=1.8 Hz, 1H), 7.95 (d, J=1.3 Hz, 1H), 7.91 (s, 1H), 6.62 (s, 1H), 6.26 (d, J=5.5 Hz, 1H), 6.02 (dd, J=11.7, 5.5 Hz, 1H), 5.57 (d, J=2.4 Hz, 1H), 5.21 (dd, J=11.7, 2.9 Hz, 1H), 4.72 (dd, J=7.5, 4.9 Hz, 1H), 4.14-3.94 (m, 2H), 2.05 (s, 3H), 1.92 (d, J=2.6 Hz, 6H).

Intermediate 18

3,5-Dichloro-4-fluoro-phenyl 3-2,4,6-tri-O-acetyl-deoxy-3-[4-(2-hydroxythiazol-4-yl)-1H-1,2,3-triazol-1-yl]-1-thio-α-D-galactopyranoside 3,5-dichloro-4-fluoro-benzenethiol

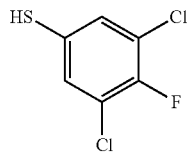

A solution of 3,5-dichloro-4-fluoroaniline (1 g, 5.58 mmol) in con. HCl (20 mL) was cooled to 0-5° C. A solution of sodium nitrite (424 mg, 6.14 mmol) in water (1 mL) was added dropwise over 20 min with stirring. The resulting solution was stirred for 1 h at 0-5° C. Potassium ethyl xantogenate (1.33 g, 8.37 mmol) was added and the reaction mixture was stirred at 70° C. overnight. The resulting solution was extracted with EtOAc (20 mL×3). The combined organic layers were washed with brine (20 mL), dried over $Na_2SO_4$, and concentrated in vacuum to give crude product, which was purified by FC to afford crude product. The crude product dissolved in EtOH (20 mL) followed by addition of 2M NaOH (5.6 mL). The mixture was stirred at 70° C. for 2h. The mixture was extracted with DCM (30 mL) and the water layer pH was adjusted to pH5-6 by $NaHSO_4$ aq. followed by addition of DCM (30 mL). The organic layer was isolated and was washed, dried over sodium sulphate and concentrated to dryness to give the title compound 90.2 mg which was used in the next step without further purification. m/z calcd for $[C_6H_3Cl_2FS]^+$ $[M-H]^-$:195.0; found: 195.0.

3,5-dichloro-4-fluoro-phenyl 2,4,6-tri-O-acetyl-3-azido-3-deoxy-1-thio-α-D-galactopyranoside

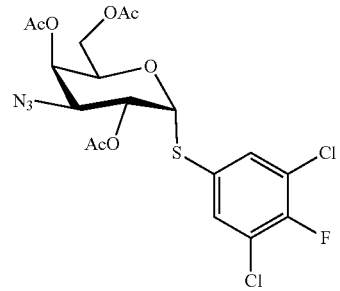

$Cs_2CO_3$ (149 mg, 0.458 mmol) was added to a solution of 3,5-dichloro-4-fluoro-benzenethiol (90.2 mg, 0.458 mmol) in DMF (5 mL) at 0° C. The solution was stirred at rt for 30 min. Then 2,4,6-tri-O-acetyl-3-azido-3-deoxy-β-D-galactopyranosyl chloride (80.0 mg, 0.229 mmol) was added to mixture. The reaction was stirred at 50° C. for 2 h. The mixture was cooled to room temperature and water (50 mL) was added. The reaction mixture was extracted with EtOAc (15 mL×3) and the combined organic layers were washed with brine, dried over $Na_2SO_4$ and concentrated in vacuo to afford crude product, which was purified by flash chromatography on a Biotage® (EA/PE=5%~40%, 30 mL/min, normal phase silica gel, uv 254) to afford th title compound (80 mg, 0.157 mmol, yield: 68.5%). $^1H$ NMR (400 MHz, $CDCl_3$) δ 7.37 (d, J=6.1 Hz, 2H), 5.86 (d, J=5.5 Hz, 1H), 5.41 (d, J=3.1 Hz, 1H), 5.19 (dd, J=11.0, 5.6 Hz, 1H), 4.53 (dd, J=7.4, 4.6 Hz, 1H), 4.01 (ddd, J=19.6, 11.7, 6.4 Hz, 2H), 3.84 (dd, J=11.0, 3.2 Hz, 1H). m/z calcd for $[C_{18}H_{18}Cl_2FN_3O_7S]^+$ $[M+H]^+$: 510.0; found: 510.0.

3,5-Dichloro-4-fluoro-phenyl 3-2,4,6-tri-O-acetyl-deoxy-3-[4-(2-hydroxythiazol-4-yl)-1H-1,2,3-triazol-1-yl]-1-thio-α-D-galactopyranoside

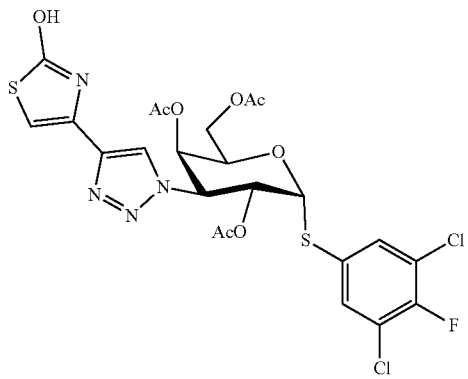

To a solution of 3,5-dichloro-4-fluoro-phenyl 2,4,6-tri-O-acetyl-3-azido-3-deoxy-1-thio-α-D-galactopyranoside (80.0 mg, 0.157 mmol) in CH$_3$CN (5 mL) were added TEA (0.109 mL, 0.784 mmol), Copper(I)Iodide (1.63 mg, 0.00854 mmol), CsF (35.7 mg, 0.235 mmol), 4-(2-trimethylsilylethynyl)thiazol-2-ol (46.4 mg, 0.235 mmol). The reaction was stirred at room temperature for 20 h under N$_2$ atmosphere. Water (10 mL) and DCM (10 mL) were added and the phases were separated, the aqueous phase was extracted with DCM (5 mL×2) and the combined organic phases were washed with water (20 mL) and brine (20 mL), dried over anhydrous sodium sulphate. Removal of solvent gave a residue which was purified by column chromatography (PE/EA=2/1) to obtain th title compound (70.0 mg, 0.110 mmol, yield: 70.3%). $^1$H NMR (400 MHz, CDCl$_3$) δ 11.00 (s, 1H), 7.95 (s, 1H), 7.49 (d, J=6.0 Hz, 2H), 6.66 (s, 1H), 6.12 (d, J=5.6 Hz, 1H), 6.02 (dd, J=11.7, 5.5 Hz, 1H), 5.62 (d, J=2.8 Hz, 1H), 5.21 (dd, J=11.6, 3.0 Hz, 1H), 4.90-4.78 (m, 1H), 4.22-4.02 (m, 2H). m/z calcd for [C$_{23}$H$_{21}$Cl$_2$FN$_4$O$_8$S$_2$]$^+$ [M+H]$^+$: 635.0; found: 635.0.

Intermediate 20

3,4,5-trichlorophenyl 2,4,6-tri-O-acetyl-3-[4-(2-hydroxythiazol-4-yl)triazol-1-yl]-3-deoxy-1-thio-α-D-galactopyranoside 3,4,5-trichlorobenzenethiol

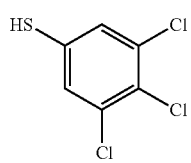

To a solution of 3,4,5-trichloroaniline (1000 mg, 5.09 mmol) in aqueous HCl (10 mL) was added NaNO$_2$ (702 mg, 10.2 mmol). The mixture was stirred at 0° C. for 2 hours. Then an aqueous solution of potassium ethyl xanthogenate (1632 mg, 10.2 mmol) (10 mL) was added into the above mixture and the reaction was stirred at 55° C. for 1 hour. The reaction mixture was cooled to room temperature and extracted with EtOAc (15 mL×2) and the combined organic layers were concentrated to afford a residue. The residue was dissolved in EtOH (5 mL) and 2M NaOH aqueous solution (2 mL) was added. The mixture was stirred at 70° C. under a nitrogen atmosphere for 2 hours. Water (10 mL) and DCM (10 mL) were added. After separation, the aqueous phase was extracted with DCM (5 mL×2) and then the pH was adjusted to pH=6-7 with saturated NaHSO$_4$ aqueous solution. The resulting solution was extracted with DCM (5 mL×2) and the combined organic phases were washed with water (20 mL) and brine (20 mL), dried over anhydrous Na$_2$SO$_4$. Removal of solvent gave the title compound (50.0% purity, 710 mg, 1.66 mmol, yield: 32.7%) which was used to the next step without any further purification 3,4,5-trichlorophenyl 2,4,6-tri-O-acetyl-3-azido-3-deoxy-1-thio-α-D-galactopyranoside

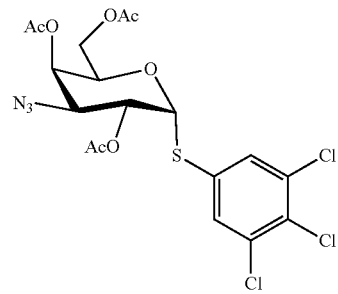

A solution of 3,4,5-trichlorobenzenethiol (300 mg, 1.41 mmol) in DMF (10 mL) was added 2,4,6-tri-O-acetyl-3-azido-3-deoxy-β-D-galactopyranosyl chloride (442 mg, 1.26 mmol) and Cs$_2$CO$_3$ (687 mg, 2.11 mmol). The mixture was stirred under a nitrogen atmosphere at room temperature overnight. The reaction mixture was poured into 20 mL of water and extracted with EA (10 mL×2). The organic layers were washed with water (5 mL×5). The organic layer was concentrated to give a brown residue which was purified by column chromatography (PE/EA=8/1~2/1, Silica-CS 12 g, 30 mL/min, silica gel, UV 254) to obtain the title compound (200 mg, 0.380 mmol, yield: 27.0%). $^1$H NMR (400 MHz, CDCl$_3$) δ 7.42 (s, 2H), 5.94 (d, J=5.5 Hz, 1H), 5.40 (d, J=2.9 Hz, 1H), 5.21 (dd, J=10.9, 5.6 Hz, 1H), 4.51 (dd, J=7.5, 4.9 Hz, 1H), 4.04 (s, 1H), 3.98-3.88 (m, 1H), 3.85 (dd, J=11.0, 3.3 Hz, 1H), 2.11 (d, J=7.5 Hz, 6H), 1.94 (s, 3H). m/z calcd for [C$_{18}$H$_{18}$Cl$_3$N$_3$O$_7$S]: [M+18]$^+$: 543; found: 543.

3,4,5-trichlorophenyl 2,4,6-tri-O-acetyl-3-[4-(2-hydroxythiazol-4-yl)triazol-1-yl]-3-deoxy-1-thio-α-D-galactopyranoside

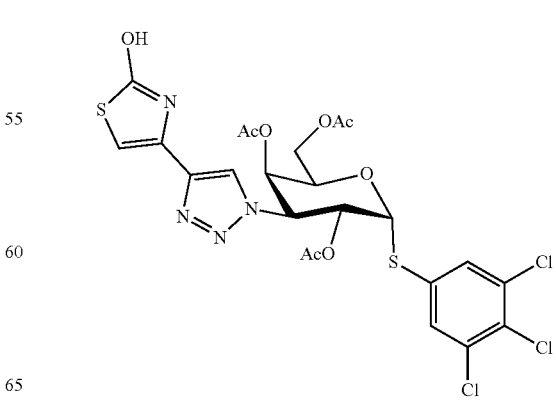

To a solution of 3,4,5-trichlorophenyl 2,4,6-tri-O-acetyl-3-azido-3-deoxy-1-thio-α-D-galactopyranoside (200 mg, 0.380 mmol) in DMF (10 mL) was added 4-(2-trimethylsilylethynyl)thiazol-2-ol (150 mg, 0.759 mmol), Copper(I) Iodide (21.7 mg, 0.114 mmol), CsF (115 mg, 0.759 mmol) and DIPEA (0.195 mL, 1.14 mmol). The mixture was stirred under a nitrogen atmosphere at room temperature overnight. The reaction mixture was poured into 20 mL of water and extracted with EtOAc (10 mL×2). The organic layer was washed with water (5 mL×5). The organic layer was concentrated to give a brown-black residue which was purified by column chromatography (PE/EA=10/1~1/1, Silica-CS 4 g, 10 mL/min, silica gel, UV 254) to obtain the title compound (35.0 mg, 0.0537 mmol, yield: 14.1%). $^1$H NMR (400 MHz, CDCl$_3$) δ 7.84 (s, 1H), 7.47 (s, 2H), 6.49 (s, 1H), 6.11 (d, J=5.5 Hz, 1H), 5.97 (dd, J=11.8, 5.3 Hz, 1H), 5.53 (s, 1H), 5.13 (d, J=9.5 Hz, 1H), 4.81-4.64 (m, 1H), 4.15-4.05 (m, 2H), 2.02 (s, 3H), 1.95 (s, 3H), 1.91 (s, 3H). m/z calcd for [C$_{23}$H$_{21}$C$_3$N$_4$O$_8$S$_2$]: [M+1]$^+$: 651.0; found: 651.0.

Intermediate 21

3,5-dibromo-4-fluorophenyl 2,4,6-tri-O-acetyl-3-deoxy-3-[4-(2-hydroxythiazol-4-yl)-1H-1,2,3-triazol-1-yl]-1-thio-α-D-galactopyranoside O-ethyl (3,5-dibromo-4-fluoro-phenyl)sulfanylmethanethioate

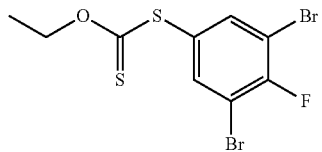

A solution of NaNO$_2$ (192 mg, 2.79 mmol) in water (1 mL) was added dropwise over 20 min to a stirred solution of 3,5-dibromo-4-fluoro-aniline (500 mg, 1.86 mmol) in aqueous concentrated HCl/H$_2$O (1/3, 12 mL) at 0-5° C. The resulting reaction mixture was stirred for 1 hour at 0-5° C. and then added dropwise to a solution of Potassium ethyl xanthate (894 mg, 5.58 mmol) in 2 mL of water. The reaction mixture was stirred at 50° C. for 2 hours. The resulting reaction mixture was cooled and extracted with EtOAc (10 mL×3). The combined organic layers were washed with brine (20 mL), dried over Na$_2$SO$_4$, and concentrated in vacuum to give crude product, which was purification by column chromatography (PE/EA=20/1~10/1, Silica-CS 12 g, 20 mL/min, silica gel, UV 254) to afford the title compound (400 mg, 1.07 mmol, yield: 57.5%). $^1$H NMR (400 MHz, CDCl$_3$) δ 7.59 (d, J=5.7 Hz, 2H), 4.56 (q, J=7.1 Hz, 2H), 1.30 (t, J=7.1 Hz, 3H).

3,5-dibromo-4-fluoro-benzenethiol

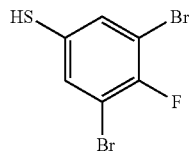

A solution of O-ethyl (3,5-dibromo-4-fluoro-phenyl)sulfanylmethanethioate (400 mg, 1.07 mmol) in EtOH (5 mL) was added NaOH (2M aqueous solution, 2 mL). The mixture was stirred under a nitrogen atmosphere at 70° C. for 2 hours. Water (10 mL) and DCM (10 mL) were added. The phases were separated and the aqueous phase was extracted with DCM (5 mL×2). The pH of the aqueous solution was adjusted to pH=6-7 with saturated aqueous NaHSO$_4$ solution. The resulting solution was extracted with DCM (15 mL×2). The combined organic phases were washed with water (20 mL) and brine (20 mL), dried over anhydrous sodium sulfate. Removal of solvent gave the crude product (250 mg, 0.874 mmol, yield: 81.8%) which was used to the next step without further purification.

m/z calcd for [C$_6$H$_3$Br$_2$FS]$^-$ [M−H]$^-$: 285; found: 285.5.

3,5-dibromo-4-fluorophenyl 2,4,6-tri-O-acetyl-3-azido-3-deoxy-1-thio-α-D-galactopyranoside

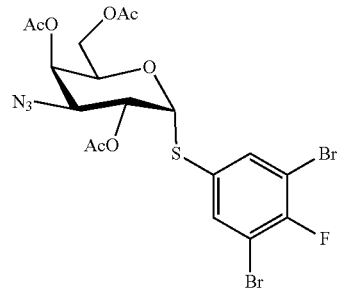

Cs$_2$CO$_3$ (279 mg, 0.858 mmol) was added to a solution of 3,5-dibromo-4-fluoro-benzenethiol (245 mg, 0.858 mmol) in DMF (5 mL) at 0° C. The solution was stirred at room temperature for 30 min. Then 2,4,6-tri-O-acetyl-3-azido-3-deoxy-β-D-galactopyranosyl chloride (200 mg, 0.572 mmol) was added to the mixture. The reaction was stirred at room temperature over night. Then it was extracted with EtOAc (5 mL×3). The combined organic layers were washed with brine, dried over Na$_2$SO$_4$ and concentrated in vacuum to afford crude product, which was purified by column chromatography (PE/EA=10/1~4/1, Silica-CS 12 g, 20 mL/min, silica gel, UV 254) to obtain the title compound (180 mg, 0.300 mmol, yield: 52.5%). $^1$H NMR (400 MHz, CDCl$_3$) δ 7.54 (d, J=5.7 Hz, 2H), 5.87 (d, J=5.5 Hz, 1H), 5.41 (d, J=2.7 Hz, 1H), 5.19 (dd, J=11.0, 5.5 Hz, 1H), 4.56-4.49 (m, 1H), 4.01 (ddd, J=19.4, 11.6, 6.2 Hz, 2H), 3.84 (dd, J=11.0, 3.2 Hz, 1H), 2.11 (d, J=11.1 Hz, 6H), 1.98 (s, 3H). m/z calcd for [C$_{18}$H$_{18}$Br$_2$FN$_3$O$_7$S]$^+$ [M+H]$^+$: 598; found: 598.

3,5-dibromo-4-fluorophenyl 2,4,6-tri-O-acetyl-3-deoxy-3-[4-(2-hydroxythiazol-4-yl)-1H-1,2,3-triazol-1-yl]-1-thio-α-D-galactopyranoside

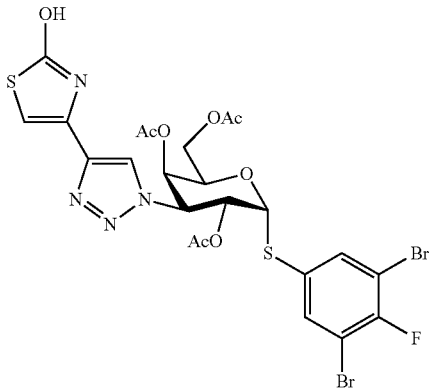

To a solution of 3,5-dibromo-4-fluorophenyl 2,4,6-tri-O-acetyl-3-azido-3-deoxy-1-thio-α-D-galactopyranoside (90.0 mg, 0.150 mmol) in DMF (3 mL) was added TEA (0.105 mL, 0.751 mmol), Copper(I)Iodide (8.58 mg, 0.0451 mmol), CsF (34.2 mg, 0.225 mmol), 4-(2-trimethylsilylethynyl)thiazol-2-ol (44.5 mg, 0.225 mmol). The reaction was stirred at room temperature under a nitrogen atmosphere for 20 hours. Water (10 mL) and DCM (10 mL) were added. The phases were separated and the aqueous phase was extracted with DCM (5 mL×2). The combined organic phases were washed with water (20 mL) and brine (20 mL), dried and over anhydrous sodium sulfate. Removal of solvent gave a residue. The residue was purified by column chromatography (PE/EA=10/1~2/1, Silica-CS 4 g, 12 mL/min, silica gel, UV 254) to obtain the title compound (50.0 mg, 0.0690 mmol, yield: 46.0%). $^1$H NMR (400 MHz, CDCl$_3$) δ 10.13 (s, 1H), 7.81 (s, 1H), 7.59 (s, 2H), 6.47 (s, 1H), 6.01 (d, J=27.9 Hz, 2H), 5.53 (s, 1H), 5.13 (s, 1H), 4.75 (s, 1H), 4.07 (d, J=19.0 Hz, 2H), 2.00 (d, J=14.8 Hz, 6H), 1.92 (s, 3H). m/z calcd for $[C_{23}H_{21}Br_2FN_4O_8S_2]^+$ $[M+H]^+$: 723; found: 723.

Intermediate 22

3-Bromo-4-cyanophenyl 2,4,6-tri-O-acetyl-3-deoxy-3-[4-(2-hydroxythiazol-4-yl)-1H-1,2,3-triazol-1-yl]-1-thio-α-D-galactopyranoside 3-Bromo-4-cyanophenyl 2,4,6-tri-O-acetyl-3-azido-3-deoxy-1-thio-α-D-galactopyranoside

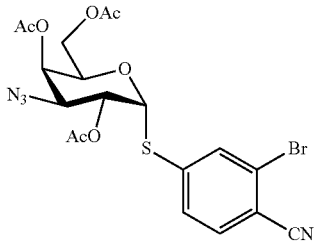

A solution of 2,4,6-tri-O-acetyl-3-azido-3-deoxy-β-D-galactopyranosyl chloride (544 mg, 1.56 mmol) and 2-bromo-4-sulfanyl-benzonitrile (500 mg, 2.33 mmol) in DMF (10 mL) was added Cs$_2$CO$_3$ (3000 mg, 9.2 mmol). The solution was stirred at room temperature overnight. The reaction mixture was poured into 20 mL of water and extracted with EtOAc (15 mL×3). The combined organic layers were washed with brine, dried over Na$_2$SO$_4$ and concentrated in vacuo to give a brown residue. The residue was purified by column chromatography (PE/EA=10/1~3/1, Silica-CS 12 g, 20 mL/min, silica gel, UV 254) to afford the title compound (0.3 g, yield: 37%). 1H NMR (400 MHz, CDCl$_3$) δ 7.69 (d, J=1.7 Hz, 1H), 7.48 (d, J=8.2 Hz, 1H), 7.38 (dd, J=8.2, 1.7 Hz, 1H), 6.09 (d, J=5.6 Hz, 1H), 5.41 (d, J=2.5 Hz, 1H), 5.24 (dd, J=11.0, 5.6 Hz, 1H), 4.50-4.37 (m, 1H), 4.07 (dd, J=11.6, 5.0 Hz, 1H), 3.90 (ddd, J=14.3, 11.3, 5.5 Hz, 2H), 2.10 (t, J=4.3 Hz, 6H), 1.89 (d, J=7.0 Hz, 3H). m/z calcd for $[C_{19}H_{19}BrN_4O_7S]$ $[M+18-3Ac]^+$: 418; found: 418.

3-Bromo-4-cyanophenyl 2,4,6-tri-O-acetyl-3-deoxy-3-[4-(2-hydroxythiazol-4-yl)-1H-1,2,3-triazol-1-yl]-1-thio-α-D-galactopyranoside

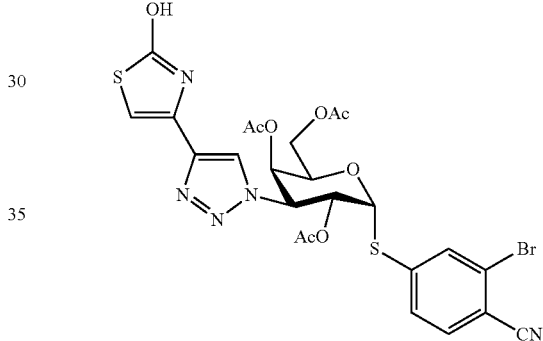

A solution of 3-bromo-4-cyanophenyl 2,4,6-tri-O-acetyl-3-azido-3-deoxy-1-thio-α-D-galactopyranoside (15.0 mg, 0.0284 mmol) in MeCN (2.0 mL) was added 4-(2-trimethylsilylethynyl)thiazol-2-ol (13.9 mg, 0.0706 mmol), Copper(I)Iodide (1.63 mg, 0.00853 mmol), CsF (8.64 mg, 0.0569 mmol) and DIPEA (18.4 mg, 0.143 mmol). The mixture was stirred at room temperature for 3 hours and concentrated under vacuum. The residue was purified by column chromatography (PE/EA=8/1~3/1, Silica-CS 4 g, 10 mL/min, silica gel, UV 254) to obtain the title compound (15 mg, 80.8% yield).

$^1$H NMR (400 MHz, CDCl$_3$) δ 10.78 (s, 1H), 8.66 (d, J=1.8 Hz, 1H), 8.20 (d, J=1.6 Hz, 1H), 8.02 (s, 1H), 7.97 (s, 1H), 6.64 (s, 1H), 6.32 (d, J=5.5 Hz, 1H), 6.09 (dd, J=11.7, 5.6 Hz, 1H), 5.63 (d, J=2.4 Hz, 1H), 5.26 (dd, J=11.7, 3.0 Hz, 1H), 4.79 (dd, J=7.4, 4.8 Hz, 1H), 4.13 (ddd, J=19.5, 11.8, 6.2 Hz, 2H), 2.11 (s, 3H), 1.99 (d, J=1.8 Hz, 6H). m/z calcd for $[C_{24}H_{22}BrN_5O_8S_2]$: $[M+1]^+$: 652; found: 652.

Intermediate 23

5-Bromo-6-trifluoromethyl-3-pyridyl 2,4,6-tri-O-acetyl-3-deoxy-3-[4-(2-hydroxythiazol-4-yl)-1H-1,2,3-triazol-1-yl]-1-thio-α-D-galactopyranoside 3-bromo-5-fluoro-2-iodo-pyridine

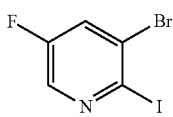

A mixture of 2,3-dibromo-5-fluoro-pyridine (5.00 g, 19.6 mmol), NaI (8.821 g, 58.9 mmol) and chloro(trimethyl)silane (2.131 g, 19.6 mmol) in MeCN (50 mL) was heated at reflux for 45 min. The reaction mixture was then poured into a 2.0 M aqueous solution of sodium hydroxide (10 mL) and extracted with diethyl ether (3×20 mL). The combined organic layers were washed with brine and evaporated to afford crude product, which was purified by column chromatography (EA/PE=1%~10%, Silica-CS 40 g, 25 mL/min, silica gel, UV 254) to afford the target compound as a gray solid (2.2 g, 37.2% yield). $^1$H NMR (400 MHz, CDCl$_3$) $^1$H NMR (400 MHz, CDCl$_3$) δ 8.21 (d, J=2.7 Hz, 1H), 7.56 (dd, J=7.5, 2.7 Hz, 1H). m/z calcd for [CH$_2$BrFIN] [M]: 300.8; found: 301. (GCMS)

3-bromo-5-fluoro-2-(trifluoromethyl)pyridine

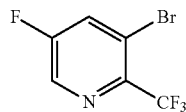

To a solution of 3-bromo-5-fluoro-2-iodo-pyridine (800 mg, 2.65 mmol) in DMF (15 mL) was added CuI (3.533 g, 18.6 mmol), methyl fluorosulfonyldifluoroacetate (3.564 g, 18.6 mmol). The mixture was heated under a nitrogen atmosphere at 80° C. for 3h. The reaction mixture was cooled to room temperature and water (50 mL) was added followed by extraction with EtOAc (15 mL×3). The combined organic layers were washed with brine, dried over Na$_2$SO$_4$ and concentrated in vacuo to afford crude product, which was purified by column chromatography (EA/PE=5%~40%, Silica-CS 40 g, 30 mL/min, silica gel, UV 254) to afford the title compound (400 mg, 1.64 mmol, yield: 61.9%). m/z calcd for [C$_6$H$_2$BrF$_4$N] [M]: 243; found: 243 (GCMS).

5-bromo-6-(trifluoromethyl)pyridine-3-thiol

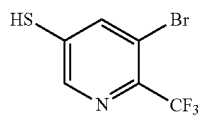

To a solution of 3-bromo-5-fluoro-2-(trifluoromethyl)pyridine (410 mg, 1.68 mmol) in DMF (10 mL) was added Na$_2$S (393 mg, 5.04 mmol). The mixture was stirred under a nitrogen atmosphere at room temperature for 8 hours. 10% aqueous NaOH solution was added into the mixture to adjust the pH to 9. The mixture was extracted with Et$_2$O (3×30 mL) and the aqueous layer was acidified with 2 M NaHSO$_4$ to pH=3. The mixture was extracted with EA (3×20 mL). The combined organic layers were washed with brine and evaporated to afford the crude product (280 mg, 1.09 mmol, yield: 64.6%). $^1$H NMR (400 MHz, CDCl$_3$) δ 8.43 (d, J=2.3 Hz, 1H), 8.19 (d, J=2.6 Hz, 1H), 3.65 (dd, J=6.8, 4.3 Hz, 1H). m/z calcd for [C$_6$H$_3$BrF$_3$NS] [M−1]$^-$: 256; found: 256.

5-Bromo-6-(trifluoromethyl)-3-pyridinyl 2,4,6-tri-O-acetyl-3-azido-3-deoxy-1-thio-α-D-galactopyranoside

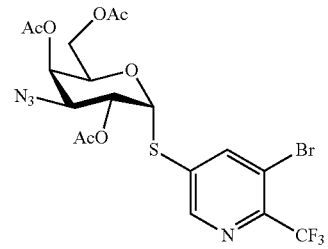

Cs$_2$CO$_3$ (405 mg, 1.24 mmol) was added to a solution of 5-bromo-6-(trifluoromethyl)pyridine-3-thiol (300 mg, 1.16 mmol) in DMF (8 mL) at 0° C. The solution was stirred at rt for 30 min. Then 2,4,6-tri-O-acetyl-3-azido-3-deoxy-β-D-galactopyranosyl chloride (290 mg, 0.829 mmol) was added to mixture. The reaction was stirred at room temperature over night. Water (30 mL) was added. Then the mixture was extracted with EtOAc (30 mL×3). The combined organic layers were washed with brine, dried over Na$_2$SO$_4$ and concentrated in vacuo to afford crude product, which was purified by column chromatography (EA/PE=5%~40%, Silica-CS 40 g, 30 mL/min, silica gel, UV 254) to afford the title compound (220 mg, 0.385 mmol, yield: 46.4%). $^1$H NMR (400 MHz, CDCl$_3$) δ 8.53 (d, J=1.8 Hz, 1H), 8.07 (d, J=1.5 Hz, 1H), 6.06 (d, J=5.5 Hz, 1H), 5.42 (d, J=2.6 Hz, 1H), 5.25 (dd, J=10.9, 5.5 Hz, 1H), 4.48 (dd, J=7.4, 4.6 Hz, 1H), 3.97-3.87 (m, 2H), 3.65 (dd, J=7.0, 5.1 Hz, 1H), 2.12 (d, J=7.3 Hz, 6H), 1.91 (s, 3H). m/z calcd for [C$_{18}$H$_{18}$BrF$_3$N$_4$O$_7$S][M+1]$^+$: 571; found: 571.

5-Bromo-6-trifluoromethyl-3-pyridyl 2,4,6-tri-O-acetyl-3-deoxy-3-[4-(2-hydroxythiazol-4-yl)-1H-1,2,3-triazol-1-yl]-1-thio-α-D-galactopyranoside

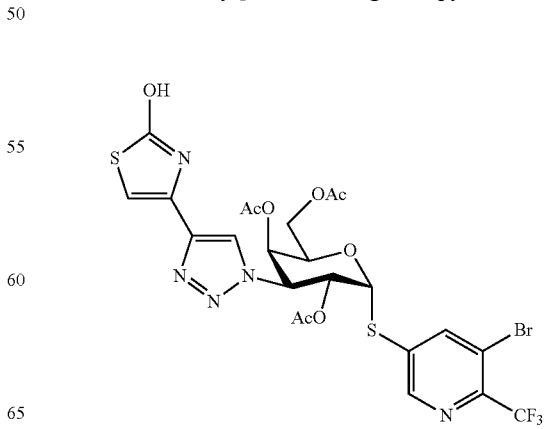

To a solution of 5-bromo-6-(trifluoromethyl)-3-pyridinyl 2,4,6-tri-O-acetyl-3-azido-3-deoxy-1-thio-α-D-galactopyranoside (70.0 mg, 0.123 mmol) in DMF (5 mL) was added TEA (0.0854 mL, 0.613 mmol), Copper(I)Iodide (7.00 mg, 0.0368 mmol), CsF (37.2 mg, 0.245 mmol), 4-(2-trimethylsilylethynyl)thiazol-2-ol (48.4 mg, 0.245 mmol). The reaction was stirred at room temperature for 20 h under a nitrogen atmosphere. Water (10 mL) and DCM (10 mL) were added. The aqueous phase was separated and extracted with DCM (5 mL×2), the combined organic phases were washed with water (20 mL) and brine (20 mL), dried over anhydrous sodium sulphate. Removal of solvent gave a residue. The residue was purified by column chromatography (PE/EA=2/1, Silica-CS 12 g, 20 mL/min, silica gel, UV 254) to obtain the title compound (65.0 mg, 0.0933 mmol, yield: 76.2%). $^1$H NMR (400 MHz, CDCl$_3$) δ 10.30 (s, 1H), 8.58 (d, J=1.9 Hz, 1H), 8.12 (s, 1H), 7.84 (s, 1H), 6.50 (s, 1H), 6.25 (d, J=5.5 Hz, 1H), 6.03 (dd, J=11.6, 5.5 Hz, 1H), 5.55 (d, J=2.9 Hz, 1H), 5.17 (dd, J=11.6, 2.9 Hz, 1H), 4.71 (d, J=7.0 Hz, 1H), 4.06 (ddd, J=19.7, 11.9, 6.5 Hz, 2H), 2.04 (s, 3H), 1.92 (d, J=1.5 Hz, 6H). m/z calcd for [C$_{23}$H$_{21}$BrF$_3$N$_5$O$_8$S$_2$]$^+$ [M+H]$^+$: 698; found: 697.8.

Intermediate 24

3-Chloro-4-trifluoromethylphenyl 2,4,6-tri-O-acetyl-3-azido-3-deoxy-1-thio-α-D-galactopyranoside

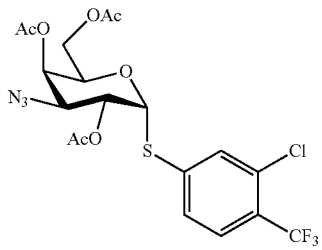

A solution of 2,4,6-tri-O-acetyl-3-azido-3-deoxy-β-D-galactopyranosyl chloride (500 mg, 1.43 mmol) and 3-chloro-4-(trifluoromethyl)benzenethiol (454 mg, 2.145 mmol) in DMF (10 mL) was added Cs$_2$CO$_3$ (1.4 g, 4.3 mmol) and the solution was stirred at room temperature overnight. The reaction was poured into 30 mL of water and extracted with EtOAc (15 mL×3). The combined organic layers were washed with brine, dried over Na$_2$SO$_4$ and concentrated in vacuo to obtain crude product. The crude target was purified by column chromatography (PE/EA=10/1~3/1, Silica-CS 12 g, 20 mL/min, silica gel, UV 254) to afford the title compound. (0.386 g, yield: 51.3%). $^1$H NMR (400 MHz, CDCl$_3$) δ 7.53 (d, J=7.7 Hz, 2H), 7.37-7.29 (m, 1H), 6.06 (d, J=5.5 Hz, 1H), 5.41 (d, J=2.6 Hz, 1H), 5.27-5.20 (m, 1H), 4.49 (dd, J=7.3, 5.3 Hz, 1H), 4.05 (d, J=4.6 Hz, 1H), 3.97-3.93 (m, 1H), 3.88 (dd, J=11.0, 3.3 Hz, 1H), 2.11 (d, J=2.5 Hz, 6H), 1.86 (d, J=3.7 Hz, 3H). m/z calcd for [C$_{19}$H$_{19}$ClF$_3$N$_3$O$_7$S] [M+18]$^+$: 543; found: 543.

3-Chloro-4-trifluoromethylphenyl 2,4,6-tri O-acetyl-3-deoxy-3-[4-(2-hydroxythiazol-4-yl)-1H-1,2,3-triazol-1-yl]-1-thio-α-D-galactopyranoside

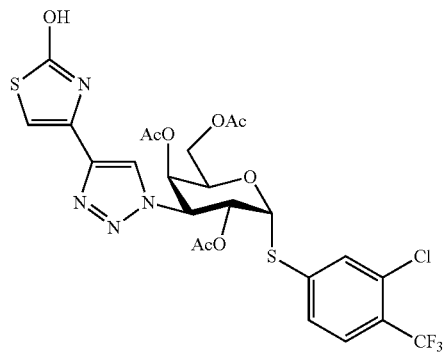

A solution of 3-chloro-4-trifluoromethylphenyl 2,4,6-tri-O-acetyl-3-azido-3-deoxy-1-thio-α-D-galactopyranoside (15.0 mg, 0.0260 mmol) in MeCN (2.0 mL) was added 4-(2-trimethylsilylethynyl)thiazol-2-ol (14 mg, 0.0708 mmol), Copper(I)Iodide (1.63 mg, 0.00856 mmol), CsF (8.67 mg, 0.0570 mmol) and DIPEA (18.4 mg, 0.143 mmol). The mixture was stirred at room temperature for 3 hours followed by solvent evaporation. The residue was purified by column chromatography (PE/EA=10/1~1/1, Silica-CS 4 g, 12 mL/min, silica gel, UV 254) to obtain the title compound (15 mg, 80.8% yield). $^1$H NMR (400 MHz, CDCl$_3$) δ 10.52 (s, 1H), 7.86 (s, 1H), 7.60-7.55 (m, 2H), 7.39 (d, J=8.1 Hz, 1H), 6.53 (s, 1H), 6.25 (d, J=5.5 Hz, 1H), 6.01 (dd, J=11.7, 5.5 Hz, 1H), 5.55 (s, 1H), 5.18 (dd, J=11.6, 2.9 Hz, 1H), 4.75-4.67 (m, 1H), 4.10-4.02 (m, 2H), 2.04 (s, 3H), 1.93-1.86 (m, 6H). m/z calcd for [C$_{24}$H$_{22}$CF$_3$N$_4$O$_8$S$_2$] [M+1]$^+$: 651; found: 651.

Intermediate 26

3-Chloro-4-methylphenyl 2,4,6-tri-O-acetyl-3-deoxy-3-[4-(2-hydroxythiazol-4-yl)-1H-1,2,3-triazol-1-yl]-1-thio-α-D-galactopyranoside 3-Chloro-4-methylphenyl 2,4,6-tri-O-acetyl-3-azido-3-deoxy-1-thio-α-D-galactopyranoside

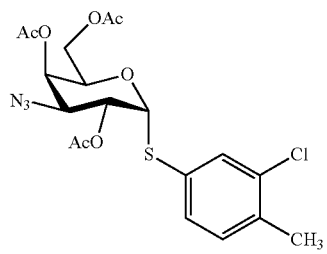

Cs$_2$CO$_3$ (838 mg, 2.57 mmol) was added to a solution of 2,4,6-tri-O-acetyl-3-azido-3-deoxy-β-D-galactopyranosyl chloride (300 mg, 0.858 mmol) and 3-chloro-4-methylbenzenethiol (272 mg, 1.72 mmol) in DMF (5 mL) at room temperature. The reaction was stirred at room temperature overnight. After diluting with water (20 mL), the reaction mixture was extracted with EtOAc (10 mL×3). The combined organic layers were washed with brine, dried over Na$_2$SO$_4$ and concentrated in vacuo. The residue was purified by column chromatography (PE/EA=10/1~3/1, Silica-CS 12 g, 20 mL/min, silica gel, UV 254) to give th title compound (270 mg, 0.572 mmol, yield: 66.7%) as pale yellow solid. $^1$H NMR (400 MHz, CDCl$_3$) δ 7.45 (s, 1H), 7.22 (s, 1H), 7.15 (d, J=7.9 Hz, 1H), 5.89 (t, J=9.4 Hz, 1H), 5.46 (s, 1H), 5.25 (dd, J=10.8, 5.4 Hz, 1H), 4.65 (t, J=5.9 Hz, 1H), 4.11 (dd, J=11.5, 4.8 Hz, 1H), 4.05-3.87 (m, 2H), 2.34 (s, 3H), 2.16 (d, J=12.3 Hz, 6H), 2.02 (d, J=13.2 Hz, 3H). m/z calcd for [C$_{19}$H$_{22}$CN$_3$O$_7$S] [M+18]$^+$: 489; found: 489.2.

3-Chloro-4-methylphenyl 2,4,6-tri-O-acetyl-3-de-oxy-3-[4-(2-hydroxythiazol-4-yl)-1H-1,2,3-triazol-1-yl]-1-thio-α-D-galactopyranoside

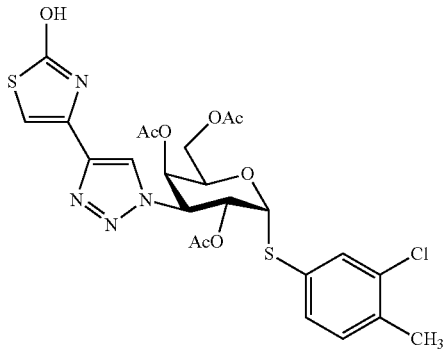

To a solution of 3-chloro-4-methylphenyl 2,4,6-tri-O-acetyl-3-azido-3-deoxy-1-thio-α-D-galactopyranoside (100 mg, 0.212 mmol) in DMF (5 mL) were added DIPEA (0.181 mL, 1.06 mmol), Copper(I)Iodide (12.1 mg, 0.0636 mmol), CsF (64.4 mg, 0.424 mmol), 4-(2-trimethylsilylethynyl)thiazol-2-ol (83.6 mg, 0.424 mmol). The reaction was stirred at room temperature under a nitrogen atmosphere overnight. Water (10 mL) and DCM (10 mL) were added. The separated aqueous phase was extracted with DCM (5 mL×2), the combined organic phases were washed with water (20 mL) and brine (20 mL), dried over anhydrous sodium sulphate. Removal of solvent gave a residue. The residue was purified by column chromatography (PE/EA=8/1~1/1, Silica-CS 12 g, 20 mL/min, silica gel, UV 254) to obtain the title compound. (50.0 mg, 0.0837 mmol, yield: 39.5%) as pale yellow solid.

$^1$H NMR (400 MHz, CDCl$_3$) δ 10.79 (s, 1H), 7.92 (s, 1H), 7.49 (d, J=1.5 Hz, 1H), 7.31-7.27 (m, 1H), 7.19 (d, J=7.9 Hz, 1H), 6.62 (s, 1H), 6.09 (d, J=5.5 Hz, 1H), 6.00 (dd, J=11.6, 5.6 Hz, 1H), 5.60 (s, 1H), 5.25 (dd, J=11.6, 2.9 Hz, 1H), 4.87 (t, J=6.0 Hz, 1H), 4.14 (dd, J=11.7, 5.5 Hz, 1H), 4.06 (dd, J=11.6, 7.3 Hz, 1H), 2.36 (s, 3H), 2.08 (s, 3H), 1.99 (d, J=14.5 Hz, 6H). m/z calcd for [C$_{24}$H$_{25}$CN$_4$O$_8$S$_2$] [M+H]$^+$: 597; found: 597.1.

Intermediate 28

5-chloro-2-(methoxycarbonyl)pyridin-3-yl 2,4,6-tri-O-acetyl-3-deoxy-3-[4-(2-hydroxythiazol-4-yl)-1H-1,2,3-triazol-1-yl]-1-thio-α-D-galactopyranoside 5-Chloro-3-fluoro-2-(methoxycarbonyl)pyridine

A solution of 5-chloro-3-fluoro-pyridine-2-carboxylic acid (1000 mg, 5.70 mmol) in MeOH (20 mL) was added thionyl chloride (1355 mg, 11.4 mmol). The mixture was stirred under a nitrogen atmosphere at room temperature overnight. After concentration, the residue was diluted with DCM (20 mL) and the pH adjusted to pH=8~9 with K$_2$CO$_3$ aqueous solution. The organic layer was concentrated in vacuum to afford th title compound (720 mg, 3.80 mmol, yield: 66.7%). $^1$H NMR (400 MHz, CDCl$_3$) δ 8.52 (d, J=1.1 Hz, 1H), 7.63 (dd, J=9.5, 1.9 Hz, 1H), 4.02 (s, 3H). m/z calcd for [C$_7$H$_5$ClFNO$_2$] [M+1]$^+$: 190, found: 190.

5-chloro-2-(methoxycarbonyl)pyridin-3-yl 2,4,6-tri-O-acetyl-3-azido-3-deoxy-1-thio-α-D-galactopyranoside

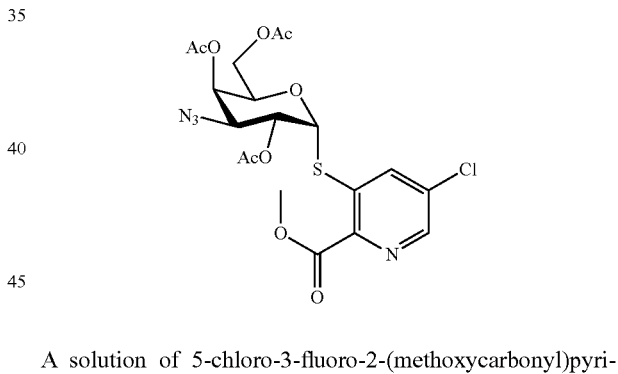

A solution of 5-chloro-3-fluoro-2-(methoxycarbonyl)pyridine (300 mg, 1.58 mmol) in DMF (20 mL) was added 2,4,6-tri-O-acetyl-3-azido-3-deoxy-β-D-galactopyranosyl chloride (1232 mg, 3.17 mmol) and diethylamine (231 mg, 3.17 mmol). The reaction was stirred under a nitrogen atmosphere at room temperature overnight. The reaction mixture was poured into 20 mL of water followed by extraction with EtOAc (10 mL×3). The combined organic layer was washed with water (10 mL×3) and brine (10 mL×3). The EtOAc solution was dried over Na$_2$SO$_4$ and filtered. The filtrate was concentrated and the residue was purified by column chromatography (PE/EA=10/1~2/1, Silica-CS 12 g, 15 mL/min, silica gel, UV 254) to obtain the title compound. (240 mg, 0.464 mmol, yield: 29.3%). $^1$H NMR (400 MHz, CDCl$_3$) δ 8.46 (d, J=2.0 Hz, 1H), 8.09 (d, J=2.0 Hz, 1H), 6.13 (d, J=5.6 Hz, 1H), 5.47 (d, J=2.6 Hz, 1H), 5.37 (dd, J=11.0, 5.6 Hz, 1H), 4.57-4.48 (m, 1H), 4.11 (ddd, J=13.1, 8.5, 4.3 Hz, 3H), 4.03 (d, J=5.5 Hz, 3H), 2.18 (d, J=2.7 Hz, 6H), 1.92 (s, 3H). m/z calcd for [C$_{19}$H$_{21}$ClN$_4$O$_9$S] [M+1]$^+$: 517, found: 517.

5-chloro-2-(methoxycarbonyl)pyridin-3-yl 2,4,6-tri-O-acetyl-3-deoxy-3-[4-(2-hydroxythiazol-4-yl)-1H-1,2,3-triazol-1-yl]-1-thio-α-D-galactopyranoside

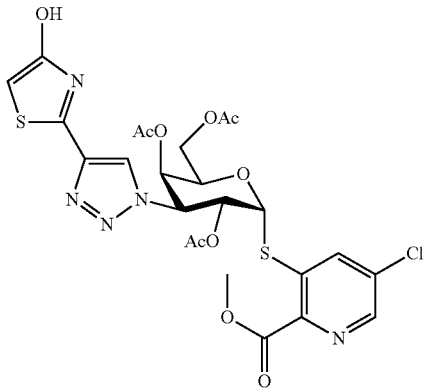

A solution of 5-chloro-2-(methoxycarbonyl)pyridin-3-yl 2,4,6-tri-O-acetyl-3-azido-3-deoxy-1-thio-α-D-galactopyranoside (240 mg, 0.464 mmol) in DMF (10 mL) was added 4-(2-trimethylsilylethynyl)thiazol-2-ol (183 mg, 0.929 mmol), copper(I) iodide (26.5 mg, 0.139 mmol), CsF (141 mg, 0.929 mmol) and DIPEA (0.318 mL, 1.86 mmol). The reaction was stirred under a nitrogen atmosphere overnight. The reaction mixture was poured into 20 mL of water followed by extraction with EtOAc (10 mL×3). The combined organic layers were washed with water (10 mL×3) and brine (10 mL×3). The EtOAc solution was dried over Na$_2$SO$_4$ and filtered. The filtrate was concentrated and the residue was purified by column chromatography (PE/EA=8/1~1/2, Silica-CS 12 g, 15 mL/min, silica gel, UV 254) to obtain the title compound (150 mg, 0.234 mmol, yield: 40.3%). $^1$H NMR (400 MHz, CDCl$_3$) δ 10.86 (s, 1H), 8.43 (s, 1H), 8.07 (s, 1H), 7.93 (s, 1H), 6.60 (s, 1H), 6.27 (d, J=5.4 Hz, 1H), 6.10 (d, J=6.3 Hz, 1H), 5.54 (s, 1H), 5.31 (d, J=10.9 Hz, 1H), 4.71 (s, 1H), 4.05 (mz, 2H), 3.98 (s, 3H), 2.03 (s, 3H), 1.98 (s, 3H), 1.90 (s, 3H). m/z calcd for [C$_{24}$H$_{24}$C$_1$N$_5$O$_{10}$S$_2$] [M+1]$^+$: 642, found: 642.

Intermediate 29

5-bromo-6-(trifluoromethyl)pyridin-3-yl 3-deoxy-3-[4-(4,5-dichlorothiazol-2-yl)-1H-1,2,3-triazol-1-yl]-1-thio-α-D-galactopyranoside 2-(4,5-dichlorothiazol-2-yl)ethynyl-trimethyl-silane

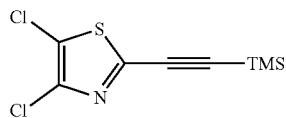

A solution of 2,4,5-trichlorothiazole (500 mg, 2.39 mmol) in DMF (5 mL) was added CuI (15.2 mg, 0.0796 mmol), TEA (1.11 mL, 7.96 mmol), PdCl$_2$(PPh$_3$)$_2$ (55.9 mg, 0.0796 mmol) and ethynyl(trimethyl)silane (313 mg, 3.18 mmol). The reaction was stirred under a nitrogen atmosphere at 30° C. for 20 hours. Removal of solvent in vacuum gave a residue. The residue was purified by column chromatography (PE/EA=50/1~10/1, Silica-CS 20 g, 20 mL/min, silica gel, UV 254) to obtain the title compound. (200 mg, 0.799 mmol, yield: 50.2%). m/z calcd for [C$_8$H$_9$Cl$_2$NSSi] [M]: 249; found: 249 (GCMS).

5-bromo-6-(trifluoromethyl)pyridin-3-yl 3-deoxy-3-[4-(4,5-dichlorothiazol-2-yl)-1H-1,2,3-triazol-1-yl]-1-thio-α-D-galactopyranoside

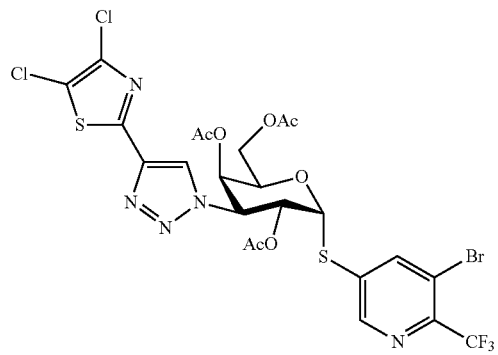

A solution of 5-Bromo-6-(trifluoromethyl)-3-pyridinyl 2,4,6-tri-O-acetyl-3-azido-3-deoxy-1-thio-α-D-galactopyranoside (intermediate 23) (50.0 mg, 0.0875 mmol) in DMF (3 mL) were added TEA (0.0610 mL, 0.438 mmol), Copper(I) Iodide (5.00 mg, 0.0263 mmol), CsF (26.6 mg, 0.175 mmol), and trimethyl-[2-(2-pyridyl)ethynyl]silane (140 mg, 0.57 mmol). The reaction was stirred under a nitrogen atmosphere at room temperature for 20 hours. Water (10 mL) and DCM (10 mL) were added. After separation, the aqueous phase was extracted with DCM (5 mL×2). The combined organic phases were washed with water (20 mL) and brine (20 mL), dried over anhydrous sodium sulfate. Removal of solvent gave a residue. The residue was purified by column chromatography (PE/EA=8/1~2/1, Silica-CS 12 g, 15 mL/min, silica gel, UV 254) to obtain the title compound (45.0 mg, 0.0601 mmol, yield: 68.6%). $^1$H NMR (400 MHz, CDCl$_3$) δ 8.58 (d, J=1.8 Hz, 1H), 8.17-8.07 (m, 1H), 8.03 (s, 1H), 6.25 (d, J=5.5 Hz, 1H), 5.97 (dd, J=11.7, 5.6 Hz, 1H), 5.55 (d, J=2.2 Hz, 1H), 5.19 (dd, J=11.7, 3.1 Hz, 1H), 4.77-4.66 (m, 1H), 4.16-3.95 (m, 2H), 2.03 (s, 3H), 1.92 (d, J=2.8 Hz, 6H). m/z calcd for [C$_{23}$H$_{19}$BrCl$_2$F$_3$N$_5$O$_7$S$_2$]$^+$[M+H]$^+$: 748; found: 748.

Intermediate 31

3,4-Dichloro-6-fluoro-phenyl 2,4,6-tri-O-acetyl-3-deoxy-3-[4-(2-hydroxythiazol-4-yl)-1H-1,2,3-triazol-1-yl]-1-thio-α-D-galactopyranoside 4,5-dichloro-2-fluoro-benzenethiol

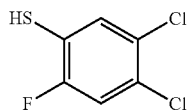

A solution of 4,5-dichloro-2-fluoro-aniline (500 mg, 2.78 mmol) in HCl (10 mL) was added NaNO$_2$ (383 mg, 5.56 mmol). The reaction was stirred at 0° C. for 2 hours. A solution of ethylxanthic acid potassium salt (891 mg, 5.56 mmol) in water (10 mL) was added into the reaction mixture and stirred at 55° C. for 1 hour. The solvents were removed in vacuo and the residue was diluted with EtOH (5 mL) followed by addition of 2M NaOH (2 mL). The mixture was heated at 70° C. under a nitrogen atmosphere for 2 hours. After cooling to room temperature, the reaction was added 10 mL of water and 10 mL of DCM. After separation, the aqueous phase was extracted with DCM (5 mL×2) and the pH was adjusted to pH=6-7 with saturated NaHSO$_4$. The resulted solution was extracted with DCM (5 mL×3) and the combined organic phases were washed with water (10 mL) and brine (10 mL), dried over anhydrous sodium sulfate. Removal of solvent gave the crude product (60.0% purity, 547 mg, yield: 50.2%) which was used to the next step without any purification 4,5-dichloro-2-fluoro-phenyl 2,4,6-tri-O-acetyl-3-azido-3-deoxy-1-thio-α-D-galactopyranoside

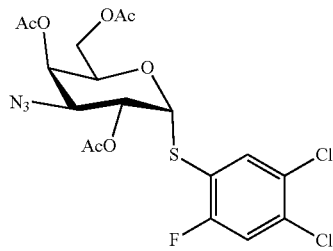

A solution of 4,5-dichloro-2-fluoro-benzenethiol (410 mg, 2.08 mmol) in DMF (10 mL) was added 2,4,6-tri-O-acetyl-3-azido-3-deoxy-β-D-galactopyranosyl chloride (655 mg, 1.87 mmol) and Cs$_2$CO$_3$ (1017 mg, 3.12 mmol). The mixture was stirred under a nitrogen atmosphere at room temperature overnight. The reaction mixture was poured into 20 mL of water followed by extraction with EtOAc (10 mL×3). The combined organic layer was washed with water (10 mL×3) and brine (10 mL×3). The EtOAc solution was dried over Na$_2$SO$_4$ and filtered. The filtrate was concentrated and the residue was purified by column chromatography (PE/EA=10/1~3/1, Silica-CS 20 g, 20 mL/min, silica gel, UV 254) to obtain the title compound (220 mg, 0.431 mmol, yield: 17.2%). $^1$H NMR (400 MHz, CDCl$_3$) δ 7.61 (d, J=6.9 Hz, 1H), 7.24 (s, 1H), 5.98 (d, J=5.5 Hz, 1H), 5.48 (d, J=2.5 Hz, 1H), 5.28 (dd, J=11.0, 5.5 Hz, 1H), 4.65-4.54 (m, 1H), 4.08 (d, J=4.9 Hz, 1H), 4.03-3.91 (m, 2H), 2.22-2.12 (m, 6H), 1.99 (s, 3H). m/z calcd for [C$_{18}$H$_{18}$Cl$_2$FN$_3$O$_7$S] [M+1]$^+$: 510, found: 510.

3,4-Dichloro-6-fluoro-phenyl 2,4,6-tri-O-acetyl-3-deoxy-3-[4-(2-hydroxythiazol-4-yl)-1H-1,2,3-triazol-1-yl]-1-thio-α-D-galactopyranoside

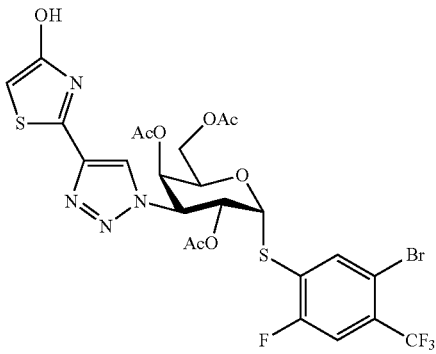

A solution of 4,5-dichloro-2-fluoro-phenyl 2,4,6-tri-O-acetyl-3-azido-3-deoxy-1-thio-α-D-galactopyranoside (100 mg, 0.196 mmol) in DMF (3 mL) was added 4-(2-trimethylsilylethynyl)thiazol-2-ol (77.3 mg, 0.392 mmol), Copper (I)Iodide (11.2 mg, 0.0588 mmol), CsF (59.5 mg, 0.392 mmol) and DIPEA (0.101 mL, 0.588 mmol). The reaction was stirred under a nitrogen atmosphere at room temperature overnight. The reaction mixture was poured into 8 mL of water followed by extraction with EtOAc (5 mL×3). The combined organic layers were washed with water (5 mL×3) and brine (5 mL×3). The EtOAc solution was dried over Na$_2$SO$_4$ and filtered. The filtrate was concentrated and the residue was purified by column chromatography (PE/EA=8/1~1/1, Silica-CS 12 g, 15 mL/min, silica gel, UV 254) to obtain the title compound (17.0 mg, 0.0268 mmol, yield: 13.7%). $^1$H NMR (400 MHz, CDCl$_3$) δ 10.65 (s, 1H), 7.97 (s, 1H), 7.64 (d, J=6.9 Hz, 1H), 7.27 (s, 1H), 6.60 (s, 1H), 6.14 (d, J=5.5 Hz, 1H), 6.02 (dd, J=11.6, 5.5 Hz, 1H), 5.60 (s, 1H), 5.28 (dd, J=11.7, 2.8 Hz, 1H), 4.85-4.71 (m, 1H), 4.05 (ddd, J=18.9, 11.7, 6.3 Hz, 2H), 2.02 (dd, J=27.5, 8.7 Hz, 9H). m/z calcd for [C$_{23}$H$_{21}$Cl$_2$FN$_4$O$_8$S$_2$] [M+1]$^+$: 635, found: 635.

Intermediate 32

5-Chloro-N,N'-dimethyl-benzamid-2-yl 3-azido-3-deoxy-1-thio-α-D-galactopyranoside 2,4,6-Tri-O-acetyl-3-azido-3-deoxy-β-D-galactopyranosyl Chloride

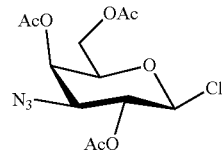

1,2,4,6-Tetra-O-acetyl-3-azido-3-deoxy-β-D-galactopyranoside (12.0 g, 32.1 mmol), PCl$_5$ (7.5 g, 36.0 mmol) and BF$_3$OEt$_2$ (50 μL, 8.16 mmol) were stirred in DCM (150 mL) for 1 h, then partitioned between NaHCO$_3$ (sat) and DCM. The organic phase was dried, concentrated and triturated in ether/petroleum ether to afford the title compound as a crystalline solid (10.2 g, 91%). ¹H NMR (400 MHz, Chloroform-d) δ 5.48 (d, J=3.2 Hz, 1H), 5.34 (t, J=9.2 Hz, 1H), 5.24 (d, J=8.7 Hz, 1H), 4.18 (dd, J=11.5, 6.1 Hz, 1H), 4.10 (dd, J=11.6, 6.7 Hz, 1H), 3.98 (t, J=6.4 Hz, 1H), 3.60 (dd, J=10.3, 3.3 Hz, 1H), 2.20 (s, 3H), 2.17 (s, 3H), 2.07 (s, 3H).

4-Chloro-2-sulfanylbenzonitrile

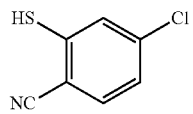

4-Chloro-2-fluoro-benzonitrile (8.0 g, 50.4 mmol), NaHS.H₂O (50.4 mmol, 4.006 g) and DMF (30 mL) were stirred on an ice bath for 1 h. The mixture was partitioned between diethyl ether and HCl (0.5 M), the organic phase was then extracted with NaOH (2 M, 50 ml) and the aqueous phase was concentrated a little, then acidified with HCl which gave a precipitate that was isolated and dried to afford the title compound (5.1 g, 59%). ¹H NMR (400 MHz, Chloroform-d) δ 7.53 (d, J=8.4 Hz, 1H), 7.43 (d, J=1.7 Hz, 1H), 7.22 (dd, J=8.4, 1.8 Hz, 1H), 4.15 (s, 1H).

4-Chloro-benzonitrile-2-yl 2,4,6-tri-O-acetyl-3-azido-3-deoxy-1-thio-α-D-galactopyranoside

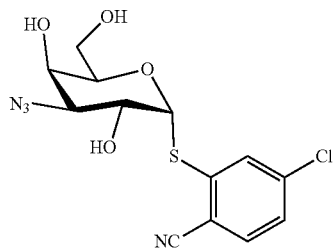

2,4,6-Tri-O-acetyl-3-azido-3-deoxy-β-D-galactopyranosyl Chloride (9.6 g, 27.3 mmol), 4-Chloro-2-sulfanylbenzonitrile (5.1 g, 30.06 mmol), Cs₂CO₃ (17.8 g, 54.7 mmol) and DMF (40 mL) were stirred at room temperature for 20 h, then partitioned between diethyl ether/EtOAc/aq. HCl/water, the organic phase was separated, concentrated, and the residue was subjected to chromatography (SiO2, petroleum ether/EtOAc) and gave the title compound (5.63 g, 42%). ¹H NMR (400 MHz, Chloroform-d) δ 7.69 (d, J=1.7 Hz, 1H), 7.61 (d, J=8.3 Hz, 1H), 7.39 (dd, J=8.3, 1.9 Hz, 1H), 6.07 (d, J=5.5 Hz, 1H), 5.51 (d, J=2.2 Hz, 1H), 5.31 (dd, J=11.0, 5.5 Hz, 1H), 4.68-4.60 (m, 1H), 4.14 (dd, J=11.7, 5.1 Hz, 1H), 4.05 (dd, J=11.6, 7.6 Hz, 1H), 3.99 (dd, J=11.0, 3.2 Hz, 1H), 2.23 (s, 3H), 2.17 (s, 3H), 2.02 (s, 3H).

5-Chloro-N,N'-dimethyl-benzamid-2-yl 3-azido-3-deoxy-1-thio-α-D-galactopyranoside

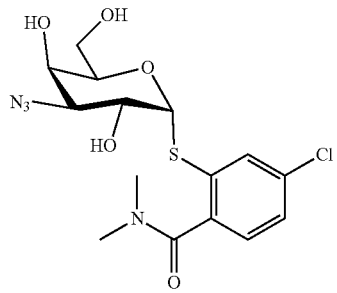

A solution of 4-chloro-benzonitrile-2-yl 2,4,6-tri-O-acetyl-3-azido-3-deoxy-1-thio-α-D-galactopyranoside (200 mg, 0.41 mmol) in EtOH (12 mL) and NaOH (aq. 2M, 6 mL) was stirred 8 h at 80° C. The solution was acidified with HCl (12 M), pH 2-3, concentrated and MeOH was added. The formed suspension was filtered and evaporated to give a dark brown residue that was partitioned between EtOAc and water. The organic phase was dried, evaporated and the obtained carboxylic acid was dissolved, along with 1-hydroxybenzotriazole hydrate (63 mg, 0.41 mmol) and N-(3-dimethylaminopropyl)-N'-ethylcarbodiimide hydrochloride (79 mg, 0.41 mmol), in DMF (2 mL). Dimethylamine (0.41 mL, 2M in THF, 0.83 mmol) was added to the mixture, which was stirred 5 h at 40° C. The mixture was concentrated and purification by HPLC (Cis, H₂O/MeCN/0.1% TFA) and freezedrying afforded the title compound as a white powder (53 mg, 32%). ¹H NMR (400 MHz, Methanol-d₄) δ 7.81 (s, 1H), 7.38 (d, J=8.2 Hz, 1H), 7.23 (d, J=8.2, 1H), 5.74 (d, J=5.4 Hz, 1H), 4.37 (dd, J=10.8, 5.4 Hz, 1H), 4.24 (t, J=6.1 Hz, 1H), 4.03 (d, J=2.8 Hz, 1H), 3.70 (dd, J=11.5, 5.4 Hz, 1H), 3.65 (dd, J=11.4, 6.8 Hz, 1H), 3.47 (dd, J=10.8, 2.8 Hz, 1H), 3.12 (s, 3H), 2.88 (s, 3H). ESI-MS m/z calcd for $[C_{15}H_{19}ClN_4O_5S]^+$ (M+H)⁺: 403.1; found: 403.1.

Intermediate 33

5-Chloro-2-(dimethylcarbamoyl)-3-pyridyl 2,4,6-tri-O-acetyl-3-azido-3-deoxy-1-thio-α-D-galactopyranoside 3-Bromo-5-chloro-N,N'-dimethyl-pyridine-2-carboxamide

Dimethylamine (1.16 mL, 2M in THF, 2.31 mmol) was added to a solution of 3-bromo-5-chloro-pyridine-2-carboxylic acid (455 mg, 1.92 mmol), 1-hydroxybenzotriazole hydrate (354 mg, 2.31 mmol) and N-(3-dimethylaminopropyl)-N'-ethylcarbodiimide hydrochloride (443 mg, 2.31 mmol), in DMF (6 mL) and Et₃N (0.32 mL, 2.31 mmol). After stirring 22 h at rt the mixture was diluted with EtOAc and washed with water. The aqueous phase was extracted with EtOAc and the combined organic phases were dried, evaporated and purified by chromatography (SiO$_2$, EtOAc/petroleum ether) to yield the title compound (346 mg, 68%). $^1$H NMR (400 MHz, Chloroform-d) δ 8.54-8.52 (m, 1H), 7.97-7.95 (m, 1H), 3.17 (s, 3H), 2.87 (s, 3H). ESI-MS m/z calcd for [C$_8$H$_8$BrClN$_2$O]$^+$ (M+H)$^+$: 263.0; found: 262.9.

5-Chloro-3-[(2,4-dimethoxyphenyl)methylsulfanyl]-N,N'-dimethyl-pyridine-2-carboxamide

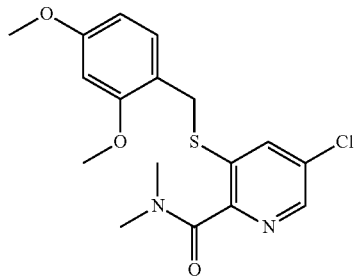 [SMILES: COc1ccc(CSc2cc(Cl)cnc2C(=O)N(C)C)c(OC)c1]

To a nitrogen purged solution of 3-bromo-5-chloro-N,N'-dimethyl-pyridine-2-carboxamide (346 mg, 1.31 mmol), Pd(dba)$_2$ (45 mg, 0.079 mmol) and 4,5-bis(diphenylphosphino)-9,9-dimethylxanthene (38 mg, 0.066 mmol) in 1,4-dioxane (2 mL), a solution of (2,4-dimethoxyphenyl)methanethiol (266 mg, 1.44 mmol) in 1,4-dioxane (3 mL) and DIPEA (0.45 mL, 2.63 mmol) was added and the resulting mixture was heated 4 h at 100° C. The mixture was concentrated and purified by chromatography (SiO$_2$, EtOAc/petroleum ether) to yield the title compound (332 mg, 69%). ESI-MS m/z calcd for [C$_{17}$H$_{19}$ClN$_2$O$_2$]$^+$ (M+H)$^+$: 367.1; found: 367.1.

5-Chloro-N,N'-dimethyl-3-sulfanyl-pyridine-2-carboxamide

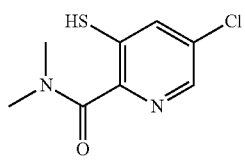

TFA (1.5 mL) was added to a solution of 5-chloro-3-[(2,4-dimethoxyphenyl)methylsulfanyl]-N,N'-dimethyl-pyridine-2-carboxamide (332 mg, 0.91 mmol) in DCM (3 mL) and Et$_3$SiH (1.5 mL) and the mixture was stirred 5 days at rt. The mixture was concentrated and purified by chromatography (SiO$_2$, EtOAc/petroleum ether) to yield the title compound (159 mg, 81%). $^1$H NMR (400 MHz, Chloroform-d) δ 8.31 (d, J=2.0 Hz, 1H), 7.69 (d, J=1.9 Hz, 1H), 4.34 (s, 1H), 3.15 (s, 3H), 2.93 (s, 3H). ESI-MS m/z calcd for [C$_8$H$_9$CN$_2$OS]$^+$ (M+H)$^+$: 217.0; found: 217.0.

5-Chloro-2-(dimethylcarbamoyl)-3-pyridyl 2,4,6-tri-O-acetyl-3-azido-3-deoxy-1-thio-α-D-galactopyranoside

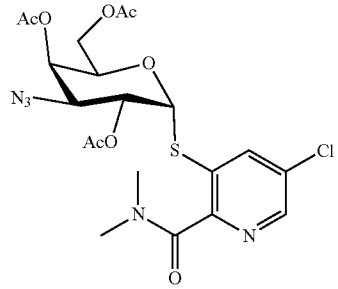

NaH (84 mg, 60% in oil, 2.20 mmol) was added to a solution of 5-chloro-N,N'-dimethyl-3-sulfanyl-pyridine-2-carboxamide (159 mg, 0.73 mmol) and 2,4,6-tri-O-acetyl-3-azido-3-deoxy-β-D-galactopyranosyl chloride (385 mg, 1.10 mmol) in DMF (5 mL) and the mixture was stirred 5 h at rt. The mixture was diluted with EtOAc and washed twice with water and once with brine, the organic phase was dried, evaporated and purified by chromatography (SiO$_2$, EtOAc/petroleum ether) to yield the title compound (202 mg, 52%). $^1$H NMR (400 MHz, Chloroform-d) δ 8.45 (d, J=2.1 Hz, 1H), 7.98 (d, J=2.1 Hz, 1H), 6.05 (d, J=5.5 Hz, 1H), 5.48 (d, J=3.1 Hz, 1H), 5.28 (dd, J=11.0, 5.5 Hz, 1H), 4.63 (dd, J=7.4, 4.6 Hz, 1H), 4.13-4.09 (m, 1H), 4.05 (dd, J=11.6, 7.7 Hz, 1H), 3.97 (dd, J=11.0, 3.3 Hz, 1H), 3.16 (s, 3H), 2.88 (s, 3H), 2.18 (s, 3H), 2.17 (s, 3H), 2.03 (s, 3H). ESI-MS m/z calcd for [C$_{20}$H$_{24}$ClN$_5$O$_8$S]$^+$ (M+H)$^+$: 530.1; found: 530.2.

I claim:
1. A D-galactopyranose compound of formula (1)

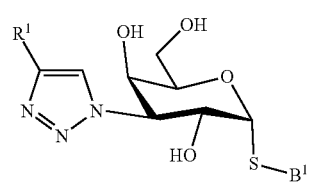

(1)

wherein the pyranose ring is a-D-galactopyranose,
R$^1$ is selected from the group consisting of

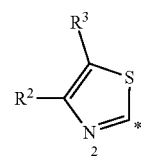

2 wherein the asterix * indicates the carbon atom of the heteroaromatic ring that is covalently attached to the triazole group of formula (1);
wherein R$^2$ is a halogen;
R$^3$ is selected from the group consisting of hydrogen, C$_{1-6}$ alkyl and halogen; and
B$^1$ is selected from a pyridinyl substituted with two groups selected from a halogen; —COOH;

—CONR$^{35}$R$^{36}$, wherein R$^{35}$ and R$^{36}$ are independently selected from H, C$_{1-3}$ alkyl, cyclopropyl, and isopropyl; isopropyl, optionally substituted with a F; CN; and a methyl optionally substituted with a F; or a pharmaceutically acceptable salt or solvate thereof.

2. The compound of claim 1, wherein R$^2$ is halogen, and R$^3$ is selected from the group consisting of hydrogen and halogen.

3. The compound of claim 1, wherein B$^1$ is selected from a pyridinyl substituted with two substituents selected from the group consisting of Cl, Br, isopropyl, COOH, CONH$_2$, CN, CON(CH$_3$)$_2$ and CF$_3$.

4. The compound of claim 1, wherein R$^2$ is Cl, and R$^3$ is hydrogen.

5. The compound of claim 1, selected from:
   5-Bromo-6-trifluoromethyl-pyridine-3-yl 3-[4-(4-chlorothiazol-2-yl)-1H-1,2,3-triazol-1-yl]-3-deoxy-1-thio-α-D-galactopyranoside,
   5-Bromo-6-trifluoromethyl-pyridine-3-yl 3-[4-(4-bromothiazol-2-yl)-1H-1,2,3-triazol-1-yl]-3-deoxy-1-thio-α-D-galactopyranoside,
   5-Chloro-6-cyano-pyridine-3-yl 3-[4-(4-chlorothiazol-2-yl)-1H-1,2,3-triazol-1-yl]-3-deoxy-1-thio-α-D-galactopyranoside,
   5-Bromo-2-cyano-pyridine-3-yl 3-[4-(4-chlorothiazol-2-yl) -1H-1,2,3-triazol-1-yl]-3-deoxy-1-thio-α-D-galactopyrano side,
   5-Chloro-2-cyano-pyridine-3-yl 3- [4-(4-chlorothiazol-2-yl)-1H-1,2,3-triazol-1-yl]-3-deoxy-1-thio-α-D-galactopyrano side,
   5-Bromo-6-cyano-3-pyridyl 3-[4-(4-chlorothiazol-2-yl)-1H-1,2,3-triazol-1-yl]-3-deoxy-1-thio-α-D-galactopyrano side,
   5-Chloro-picolinamide-3-yl 3-[4-(4-chlorothiazol-2-yl)-1H-1,2,3-triazol-1-yl]-3-deoxy-1-thio-α-D-galactopyrano side,
   5-Bromo-6-trifluoromethyl-pyridine-3-yl 3-deoxy-3-[4-(4,5-dichlorothiazol-2-yl)-1H-1,2,3-triazol-1-yl]-1-thio-α-D-galactopyrano side,
   5-Bromo-2-isopropyl-pyridine-3-yl 3-[4-(4-chlorothiazol-2-yl)-1H-1,2,3-triazol-1-yl]-3-deoxy-1-thio-α-D-galactopyrano side; or
   a pharmaceutically acceptable salt or solvate thereof.

6. A pharmaceutical composition comprising the compound of claim 1 and optionally a pharmaceutically acceptable additive.

7. A method for treatment of a disorder relating to the binding of a galectin-1 to a ligand in a mammal, wherein a therapeutically effective amount of at least one compound according to claim 1 is administered to a mammal in need of said treatment wherein said disorder is selected from the group consisting of inflammation; fibrosis, scarring; keloid formation; aberrant scar formation; scleroderma; sclerosis; surgical adhesions; septic shock;
   cancer, metastasising cancers; neovascularization related to cancer; autoimmune diseases, transplant rejection; metabolic disorders; heart disease; heart failure; pathological angiogenesis, disease or condition associated with ocular angiogenesis, and eye diseases, atherosclerosis;
   metabolic diseases obesity; asthma and other interstitial lung diseases, including Hermansky-Pudlak syndrome, mesothelioma; liver disorders.

* * * * *